US009051572B2

(12) United States Patent
Melino et al.

(10) Patent No.: US 9,051,572 B2
(45) Date of Patent: Jun. 9, 2015

(54) MODULATORS OF ITCH UBIQUITINASE ACTIVITY

(75) Inventors: Gennaro Melino, Leicester (GB); Mario Rossi, Leicester (GB); Paolo Salomoni, Leicester (GB)

(73) Assignee: RYBOQUIN COMPANY LIMITED, Selkirk (GB)

( * ) Notice: Subject to any disclaimer, the term of this patent is extended or adjusted under 35 U.S.C. 154(b) by 1429 days.

(21) Appl. No.: 11/813,585

(22) PCT Filed: Jan. 19, 2006

(86) PCT No.: PCT/GB2006/000181
§ 371 (c)(1),
(2), (4) Date: May 5, 2008

(87) PCT Pub. No.: WO2006/077407
PCT Pub. Date: Jul. 27, 2006

(65) Prior Publication Data
US 2009/0306187 A1 Dec. 10, 2009

Related U.S. Application Data

(60) Provisional application No. 60/646,425, filed on Jan. 24, 2005.

(30) Foreign Application Priority Data

Jan. 20, 2005 (GB) .................................. 0501202.6

(51) Int. Cl.
A61K 48/00 (2006.01)
C12N 15/113 (2010.01)
A61K 45/06 (2006.01)
C12N 9/00 (2006.01)

(52) U.S. Cl.
CPC ............ *C12N 15/1137* (2013.01); *A61K 45/06* (2013.01); *C12N 9/93* (2013.01); *C12N 2310/14* (2013.01); *C12Y 603/02019* (2013.01)

(58) Field of Classification Search
CPC ................................................. C12N 2310/14
See application file for complete search history.

(56) References Cited

U.S. PATENT DOCUMENTS

| 4,946,779 | A | 8/1990 | Kameda et al. |
| 5,545,807 | A | 8/1996 | Surani et al. |
| 5,582,981 | A | 12/1996 | Toole et al. |
| 5,595,877 | A | 1/1997 | Gold et al. |
| 5,637,459 | A | 6/1997 | Burke et al. |
| 5,976,849 | A | 11/1999 | Hustad et al. |
| 6,075,181 | A | 6/2000 | Kucherlapati et al. |
| 6,087,122 | A | 7/2000 | Hustad et al. |
| 6,100,090 | A | 8/2000 | Monia et al. |
| 2007/0274915 | A1* | 11/2007 | Rao et al. ........................ 424/9.2 |

FOREIGN PATENT DOCUMENTS

| EP | 1479398 | 11/2004 |
| WO | WO-84/03564 | 9/1984 |
| WO | WO-99/19357 | 4/1999 |
| WO | 99/40201 A1 | 8/1999 |
| WO | WO-01/75145 | 10/2001 |
| WO | WO-02/12325 | 2/2002 |
| WO | 02/061434 | 8/2002 |
| WO | WO-03/025010 | 3/2003 |
| WO | 2005/070044 | 8/2005 |
| WO | WO-2005/079458 | 9/2005 |

OTHER PUBLICATIONS

Heissmeyer et al., Nat. Immunol., 5:238-240 (2004).
Heissmeyer et al., Sci STKE, 241:29 (2004).
Agami et al., "Interaction of c-Abl and p73α and their collaboration to induce apoptosis," *Nature*, 399:809-813 (1999).
Bai et al., "Itch E3 ligase-mediated regulation of TGF-β signaling by modulating smad2 phosphorylation," *Mol. Cell*, 15:825-831 (2004).
Balint et al., "Mdm2 binds p73 α without targeting degradation," *Oncogene*, 18:3923-3929 (1999).
Bernassola et al., "Ubiquitin-dependent degradation of p73 is inhibited by PML," *J. Exp. Med.*, 199:1545-1557 (2004).
Blackwell et al., "Differences and similarities in DNA-binding preferences of MyoD and E2A protein complexes revealed by binding site selection," *Science*, 250:1104-1110 (1990).
Blackwell et al., "Sequence-specific DNA binding by the c-Myc protein," *Science*, 250:1149-1152 (1990).
Casciano et al., "Expression of ΔNp73 is a molecular marker for adverse outcome in neuroblastoma patients," *Cell Death Differ.*, 9:246-251 (2002).
Castagnoli et al., "Alternative bacteriophage display systems," *Comb. Chem. High Throughput Screen*, 4:121-133 (2001).
Catani et al., "Ascorbate up-regulates MLH1 (Mut L homologue-1) and p73: implications for the cellular response to DNA damage," *Biochem. J.*, 364:441-447 (2002).
Chen et al., "p73 is transcriptionally regulated by DNA damage, p53 and p73," *Oncogene*, 20:769-774 (2001).
Cote et al., "Generation of human monoclonal antibodies reactive with cellular antigens," *Proc. Natl. Acad. Sci. USA*, 80:2026-2030 (1983).
Crook et al., "High level expression of ΔN-p63: a mechanism for the inactivation of p53 in undifferentiated nasopharyngeal carcinoma (NPC)?", *Oncogene*, 19: 3439-3444 (2000).
De Laurenzi et al., "Additional complexityin p73: induction by mitogens in lymphoid cells and identification of two new splicing variants ε and ζ," *Cell Death Differ.*, 6:389-390 (1999).

(Continued)

*Primary Examiner* — Kimberly Chong
(74) *Attorney, Agent, or Firm* — McAndews Held & Malloy, Ltd.

(57) ABSTRACT

The present invention relates to the identification of new drug targets for therapy of disorders including cancer. In particular, the present invention relates to inhibition of the E3 ubiquitin ligase, Itch, as a means for treating disorders. Furthermore, the present invention relates to the regulation of p63 and p73 stability in cells. In particular, the invention relates to the modulation of the regulation of p63 and p73 stability in cells through modulation of the expression or activity of Itch. Moreover, the invention relates to the use of Itch as a target for the development of agents capable of modulating p63 or p73 stability and especially agents capable of modulating the interaction of Itch and pq63 or p73. Such agents may be useful in therapeutic applications including cancer treatment and modulation of skin differentiation.

14 Claims, 30 Drawing Sheets

(56) References Cited

OTHER PUBLICATIONS

De Laurenzi et al., "Induction of neuronal differentiation by p73, in a neuroblastoma cell line," *J. Biol. Chem.*, 275:15226-15231 (2000).
De Laurenzi et al., "Two new p73 splice variants, γ and Δ, with different transcriptional activity," *J. Exp. Med.*, 188:1763-1768 (1998).
Dobbelstein et al., "Inactivation of the p53-homologue p73 by the mdm2-oncoprotein," *Oncogene*, 18: 2101-2106 (1999).
Fang et al., "Dysregulation of T lymphocyte function in Itchy mice: a role for Itch in TH2 differentiation," *Nat. Immunol.*, 3:281-287 (2002).
Flores et al., "Tumor predisposition in mice mutant for p63 and p73: evidence for broader tumor suppressor functions for the p53 family," *Cancer Cell*, 7:363-373 (2005).
Gao et al., "Jun turnover is controlled through JNK-dependent phosphorylation of the E3 ligase Itch," *Science*, 306:271-275 (2004).
Gong et al., "The tyrosine kinase c-Abl regulates p73 in apoptotic response to cisplatin-induced DNA damage," *Nature*, 399:806-809 (1999).
Gottifredi et al., "Polyomavirus large T antigen induces alterations in cytoplasmic signalling pathways involving Shc activation," *J. Virol.*, 73:1427-1437 (1999).
Grob et al., "Human Δ Np73 regulates a dominant negative feedback loop for TAp73 and p53," *Cell Death Differ.*, 8:1213-1223 (2001).
Hamilton et al., "Nuclear import/export of hRPF1/Nedd4 regulates the ubiquitin-dependent degradation of its nuclear substrates," *J. Biol. Chem.*, 276:26324-26331 (2001).
Harvey et al., "Nedd4-like proteins: an emerging family of ubiquitin protein ligases implicated in diverse cellular functions," *Trends Cell Biol.*, 9:166-169 (1999).
Huse et al., "Generation of a large combinatorial library of the immunoglobulin repertoire in phage lambda," *Science*, 246:1275-1281 (1989).
Ikawa et al., "p53 family genes: structural comparison, expression and mutation," *Cell Death Differ.*, 6:1154-1161 (1999).
Irwin et al., "Chemosensitivity linked to p73 function," *Cancer Cell*, 3:403-410 (2003).
Kaghad et al., "Monoallelically expressed gene related to p53 at 1p36, a region frequently deleted in neuroblastoma and other human cancers," *Cell*, 90:809-819 (1997).
Kloetzel et al., "Antigen processing by the proteasome," *Nat. Rev. Mol. Cell Biol.*, 2:179-187 (2001).
Kozbor et al., "The production of monoclonal antibodies from human lymphocytes," *Immunology Today*, 4:72-79 (1983).
Kumar et al., "Physical interaction between specific E2 and Hect E3 enzymes determines functional cooperativity," *J. Biol. Chem.*, 272:13548-13554 (1997).
Lang et al., "Gain of function of a p53 hot spot mutation in a mouse model of Li Fraumeni syndrome," *Cell*, 119:861-872 (2004).
Lohrum et al., "Regulation and activation of p53 and its family members," *Cell Death Differ.*, 6:1162-1168 (1999).
Maisse et al., "DNA damage induces the rapid and selective degradation of the ΔNp73 isoform, allowing apoptosis to occur," *Cell Death Differ.*, 11:685-687 (2004).
Melino et al., "p73 induces apoptosis via PUMA transactivation and Bax mitochondrial translocation," *J. Biol. Chem.*, 279:8076-8083 (2004).
Mills et al., "p63 is a p53 homologue required for limb and epidermal morphogenesis," *Nature*, 398:708-713 (1999).
Miyazaki et al., "A novel HECT-type E3 ubiquitin ligase, NEDL2, stabilizes p73 and enhances its transcriptional activity," *Biochem. Biophys. Res. Comm.*, 308:106-113 (2003).
Morrison et al., "Chimeric human antibody molecules: mouse antigen-binding domains with human constant region domains," *Proc. Natl. Acad. Sci. USA*, 81:6851-6855 (1984).
Nakano et al., "A ribonucelotide reductase gene is a transcriptional target of p53 and p73," *Oncogene*, 19:4283-4289 (2000).
Neckers et al., "Antisense inhibition of oncogene expression," *Crit. Rev. Oncog.*, 3:175-231 (1992).

Neuberger et al., "Recombinant antibodies possessing novel effector functions," *Nature*, 312:604-608 (1984).
Oberst et al., "Regulation of the p73 protein stability and degradation," *Biochemical and Biophysical Research Communications*,331:707-712 (2005).
Olive et al., "Mutant p53 gain of function in two mouse models of Li Fraumeni syndrome," *Cell*, 119:847-860 (2004).
Ongkeko et al., "MDM2 and MDMX bind and stabilize the p53-related protein p73," *Curr. Biol.*, 9:829-832 (1999).
Orlandi et al., "Cloning immunoglobulin variable domains for expression by the polymerase chain reaction," *Proc. Natl. Acad. Sci. USA*, 86:3833-3837 (1989).
Owicki et al., "Continuous monitoring of receptor-mediated changes in the metabolic rates of living cells," *Proc. Natl. Acad. Sci. USA*, 87:4007-4011 (1990).
Parce et al., "Detection of cell-affecting agents with a silicon biosensor," *Science*, 246:243-247 (1989).
Park et al., "Frequent alteration of p63 expression in human primary bladder carcinomas," *Cancer Res.*, 60:3370-3374 (2000).
Putzer et al., "Increased ΔN-p73 expression in tumors by upregulation of the E2F1-regulated, TA-promoter-derived ΔN'-p73 transcript," *Cell Death Differ.*, 10:612-614 (2003).
Qiu et al., "Recognition and ubiquitination of Notch by Itch, a Hect-type E3 ubiquitin ligase," *J. Biol. Chem.*, 275:35734-35737 (2000).
Reynolds et al., "Rational siRNA design for RNA interference," *Nat. Biotechnol.*, 22:326-330 (2004).
Rossi et al., "The ubiquitin-protein ligase Itch regulates p73 stability," *The EMBO Journal*, 24:836-848 (2005).
Simon et al., "Peptoids: a modular approach to drug discovery," *Proc. Natl. Acad. Sci. USA*, 89:9367-9371 (1992).
Stiewe et al., "Role of p73 in malignancy: tumor suppressor or oncogene?" *Cell Death Differ.*, 9:237-245 (2002).
Strano et al., "Physical interaction with Yes-associated protein enhances p73 transcriptional activity," *J. Biol. Chem.*, 276:15164-15173 (2001).
Takeda et al., "Construction of chimaeric processed immunoglobulin genes containing Cmouse variable and human constant region sequences," *Nature*, 314:452-454 (1985).
Toh et al., "c-Jun regulates the stability and activity of the p53 homologue, p73," *J. Biol. Chem.*, 279:44713-44722 (2004).
Tuerk et al., "Systematic evolution of ligands by exponential enrichment: RNA ligands to bacteriophage T4 DNA polymerase," *Science*, 249:505-510 (1990).
Ueda et al., "New p73 variants with altered C-terminal structures have varied transcriptional activities," *Oncogene*, 18:4993-4998 (1999).
Urist et al., "Loss of p63 experssion is associated with tumor progression in bladder cancer," *Am. J. Pathol.*, 161:1199-1206 (2002).
Vossio et al., "DN-p73 is activated after DNA damage in a p53-dependent manner to regulate p53-induced cell cycle arrest," *Oncogene*, 21:3796-3803 (2002).
Weissman, "Themes and variations on ubiquitylation," *Nat. Rev. Mol. Cell Biol.*, 2:169-178 (2001).
Winberg et al., "Latent membrane protein 2A of Epstein-Barr virus binds WW domain E3 protein ubiquitin ligases that ubiquitinate B-cell tyrosine kinases," *Mol. Cell Biol.*, 20:8526-8535 (2000).
Yang et al., "Negative regulation of the E3 ubiquitin ligase itch via Fyn-mediated tyrosine phosphorylation," *Mol. Cell*, 21:135-141 (2006).
Yang et al., "p63 is essential for regenerative proliferation in limb, craniofacial and epithelial development," *Nature*, 398:714-718 (1999).
Yang et al., "p73-deficient mice have neurological, pheromonel and inflammatory defects but lack spontaneous tumours," *Nature*, 404:99-103 (2000).
Yuan et al., "p73 is regulated by tyrosine kinase c-Abl in the apoptotic response to DNA damage," *Nature*, 399:814-817 (1999).
Zaika et al., "ΔNp73, a dominant-negative inhibitor of wild-type p53 and TAp73, is up-regulated in human tumors," *J. Exp. Med.*, 196:765-780 (2002).
Zeng et al., "MDM2 suppresses p73 function without promoting p73 degradation," *Mol. Cell Biol.*, 19:3257-3266 (1999).

(56) References Cited

OTHER PUBLICATIONS

International Search Report and Written Opinion dated Jul. 27, 2006 for international application No. PCT/GB2006/000181.
GenBank accession No. NM_003722, *Homo sapiens* tumor protein p73-like (TP73L), mRNA, Jul. 1, 2007.
GenBank accession No. NM_005427, Homo sampiens tumor protein p73 (TP73), mRNA, Jun. 27, 2007.
GenBank accession No. NM_031483, *Homo sapiens* itchy homolog E3 ubiquitin protein ligase (mouse) (Itch), mRNA, Jun. 27, 2007.
GenBank accession No. NP_113671, Itchy homolog E3 ubiquitin protein ligase [*Homo sapiens*], Jun. 27, 1997.
Bernardi et al., "PML regulates p53 stability by sequestering Mdm2 to the nucleolus," *Nat. Cell Biol.*, 6:665-672 (2004).
Brunner et al., "p63 gene mutations and human developmental syndromes," *Am. J. Med. Genet.*, 112:284-290 (2002).
Cesareni et al., "Phage displayed peptide libraries," *Comb. Chem. High Throughput Screen.*, 2:1-17 (1999).
Davydov et al., "Assay for ubiquitin ligase activity: high-throughput screen for inhibitors of HDM2," *J. Biomolecular Screening*, 9:695-703 (2004).
Hicke, "Protein regulation by monoubiquitin," *Nat. Rev. Mol. Cell Biology*, 2:195-201 (2001).
Hong et al., "Development of a high throughput time-resolved fluorescence resonance energy transfer assay for TRAF6 ubiquitin polymerization," *Assay and Drug Development Technologies*, 1:175-180 (2003).
Horwell, "The peptoid approach to the design of non-peptide, small molecule agonists and antagonists of neuropeptides," *Trends Biotechnol.*, 13:132-134 (1995).
Joyce, "Amplification, mutation and selection of catalytic RNA," *Gene*, 82:83-87 (1989).
Kenten et al., "Assays for high-throughput screening of E2 and E3 ubiquitin ligases," *Methods Enzymol.*, 399:682-701 (2005).
Kohler et al., "Continuous cultures of fused cells secreting antibody of predefined specificity," *Nature*, 256:495-497 (1975).
Melino et al., "p73: friend or foe in tumorigenesis," *Nat. Rev. Cancer*, 2:605-615 (2002).
Melino et al., "Functional regulation of p73 and p63: development and cancer," *Trends Biochem. Sci.*, 28:663-670 (2003).
Nylander et al., "Differential expression of p63 isoforms in normal tissues and neoplastic cells," *J. Pathol.*, 198:417-427 (2002).
Perry et al., "The Itchy locus encodes a novel ubiquitin protein ligase that is disrupted in a18H mice," *Nat. Genet.*, 18:143-146 (1998).
Romani et al., "Biological and clinical role of p73 in neuroblastoma," *Cancer Lett.*, 197:111-117 (2003).
Sayan et al., "p73: in silico evidence for a putative third promoter region," *Biochem. Biophys. Res. Commun.*, 313:765-770 (2004).
Sudol, "Structure and function of the WW domain," *Prog. Biophys. Mol. Biol.*, 65:113-132 (1996).
Tschan et al., "Enhanced p73 expression during differentiation and complex p73 isoforms in myeloid leukemia," *Biochem. Biophys. Res. Comm.*, 277:62-65 (2000).
Treier et al., "Ubiquitin-dependent c-Jun degradation in vivo is mediated by the domain," *Cell*, 78:787-798 (1994).
Winter et al., "Man-made antibodies," *Nature*, 349: 293-299 (1991).
Yabuki et al., "Application of homogeneous time-resolved fluorescence (HTRFTM) to monitor poly-ubiquitination of wild-type p53," *Comb. Chem. High Throughput Screen.*, 5:279-287 (1999).
Zucconi et al., "Selection of ligands by panning of domain libraries displayed on phage lambda reveals new potential partners of synaptojanin 1," *J. Mol. Biol.*, 307:1329-1339 (2001).
International Preliminary Report on Patentability for Application No. PCT/GB2006/00181, Jul. 27, 2007.
Oberdoerffer et al., "Efficiency of RNA interference in the mouse hematopoietic system varies between cell types and developmental stages," Mol. Cell. Biol., 25(10):3896-3905 (2005).
Mueller, "E3 ubiquitin ligases as T cell anergy factors," Nat. Immunol., 5(9):883-890 (2004).
Pray et al., "Cell cycle regulatory E3 ubiquitin ligases as anticancer targets," Drug Resistance Updates, 5:249-258 (2002).
Sun, "Targeting E3 Ubiquitin Ligases for Cancer Therapy," Cancer Biol. Ther., 2(6):623-629 (2003).

\* cited by examiner

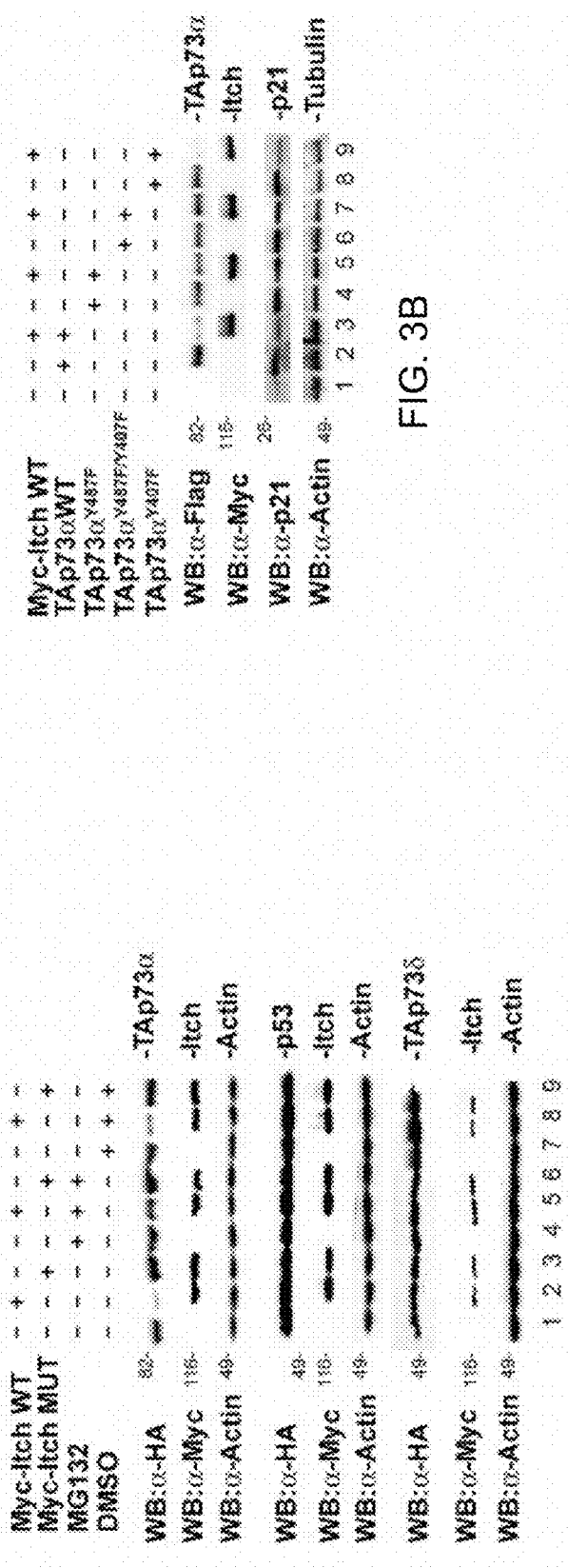

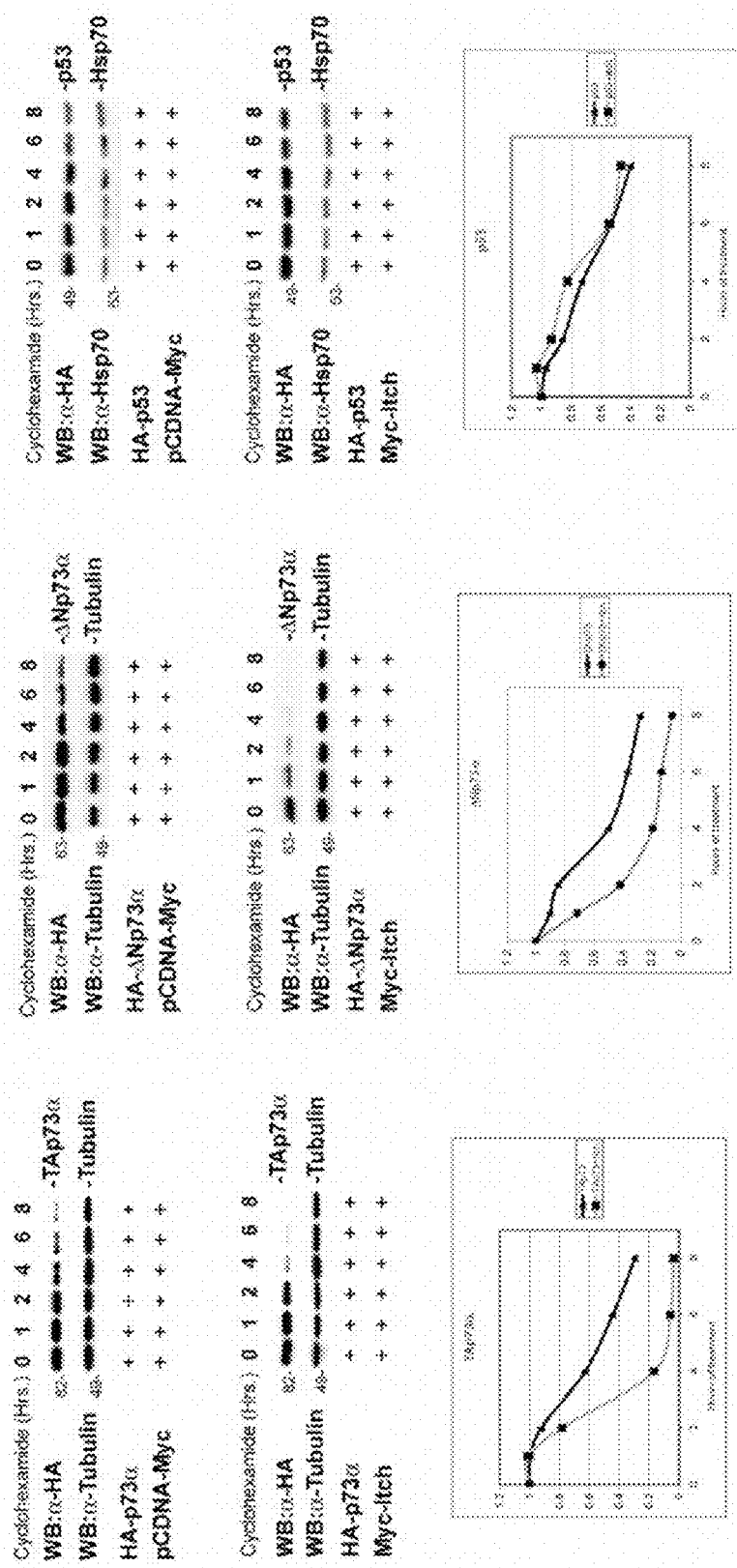

A

B

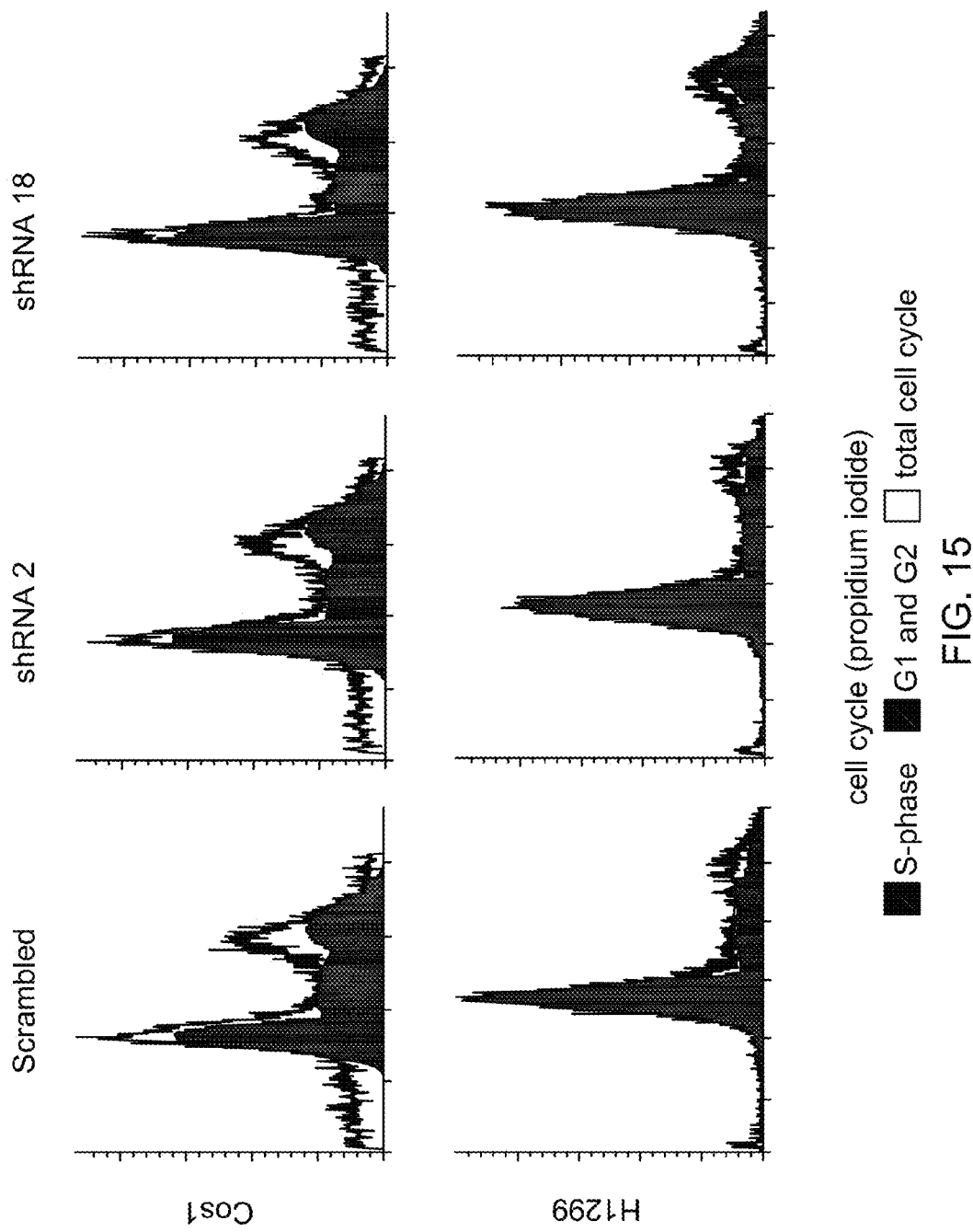

MODULATORS OF ITCH UBIQUITINASE ACTIVITY

This application is a U.S. National Phase Application pursuant to 35 U.S.C. 371 of International Application No. PCT/GB2006/000181, which was filed Jan. 19, 2006, claiming benefit of priority of Great Britain Patent Application No. 0501202.6, which was filed Jan. 20, 2005 and U.S. Provisional Patent Application No. 60/646,425, which was filed Jan. 24, 2005. The entire disclosure of each of the foregoing applications is incorporated herein by reference.

SUMMARY OF THE INVENTION

The present invention relates to the identification of new drug targets for therapy of disorders including cancer. In particular, the present invention relates to inhibition of the E3 ubiquitin ligase, Itch, as a means for treating disorders. Furthermore, the present invention relates to the regulation of p63 and p73 stability in cells. In particular, the invention relates to the modulation of the regulation of p63 and p73 stability in cells through modulation of the expression or activity of Itch. Moreover, the invention relates to the use of Itch as a target for the development of agents capable of modulating p63 or p73 stability and especially agents capable of modulating the interaction of Itch and p63 or p73. Such agents may be useful in therapeutic applications including cancer treatment and modulation of skin differentiation.

BACKGROUND OF THE INVENTION

Although our understanding of the mechanisms and possible treatment of cancer has increased over recent years, cancer remains a major cause of death throughout the developed world. Non-specific approaches to cancer management, such as surgery, radiotherapy and generalized chemotherapy, have been successful in the management of some circulating and slow-growing solid cancers. However, many types of cancer are generally highly resistant to standard treatments. Accordingly, there is a need for further, and more effective, cancer therapies.

The development of new therapies depends on the identification of suitable targets for drug activity.

The tumour suppressor gene p53 induces cell cycle arrest and promotes apoptosis thereby preventing transformation of cells. Inactivation of the tumour suppressor gene p53 is the most common genetic defect in cancer affecting more than half of all human tumours. The p53 protein is stabilized in response to genotoxic stress, metabolic changes and other potentially dangerous events which can result in transformation of cells.

p63 and p73 are members of the p53 family of transcription factors and have been shown to act in a pathway parallel to that of p53, being up-regulated in response to DNA damage and inducing growth arrest and apoptosis in a p53 independent pathway. Regulation and function of p63 and p73 is reviewed in Melino et al. 2003. They both induce cell cycle arrest and apoptosis and have been recently shown to act as tumour suppressors in vivo (Flores et al., 2005).

The importance of p63 and p73 in tumour suppression is demonstrated by the finding that disruption of p63 and p73 in p53−/− cells increases their transformation capacity. Recently it has been shown that the specific p53 mutations commonly found in cancers such as Li Fraumeni syndrome lead to functional inactivation of p73 and p63 and therefore inactivation of p63 and p73 is relevant to in vivo tumorigenesis (Lang et al, 2004; Olive et al, 2004).

Both p63 and p73, like p53, have a modular structure (FIG. 1A) (Kaghad, 1997). They share a high degree of sequence homology with p53 and can bind to p53-responsive elements activating the transcription of p53 target genes, such as those inducing cell cycle arrest and promoting apoptosis (Catani, 2002; De Laurenzi, 1998; De Laurenzi, 2000).

Unlike p53, however, p73 and p63 are expressed as different isoforms (Kaghad, 1997; Ueda, 1999) some of which lack the transactivation domain and are believed to act as dominant negative proteins (Melino, G et al.). Most of the variation generated by alternative splicing occurs at the 3' end, in a part of the sequence that does not have a counterpart in p53. The existence of these variant isoforms has made it difficult to determine the importance of p63 and p73 in tumour suppression. However, recent work using p63/p73 mutant mice has clearly demonstrated that both these proteins have tumour suppressor functions independent of p53. In addition, p63 and p73 mutant mice are predisposed to aggressive epithelial tumours common in humans (e.g. lung and mammary adenocarcinomas), unlike p53 mutant mice, which primarily develop thymic lymphomas and sarcomas (Flores et al, 2005).

At least six different p73 proteins ($\alpha$ to $\eta$) are generated (De Laurenzi, 1999; De Laurenzi, 1998; Ueda, 1999) while at least three different p63 proteins are generated as alternatively spliced C-terminal isomeric forms. In addition, both p63 and p73 genes exploit an alternative promoter and an extra exon (exon 3') to generate N-terminally truncated isoforms ($\Delta$Np63 and $\Delta$Np73). These variants lack the transactivation domain and act as "dominant negatives", blocking the function of either p53, p63 or p73 full-length proteins (Grob, 2001; Sayan et al., 2004; Yang, 2000). The relative levels of TA and $\Delta$N isoforms determine cell fate, resulting in either growth arrest and death or uncontrolled proliferation.

TAp73 steady state protein levels are up-regulated in response to DNA damage in a fashion distinct from p53 (Agami, 1999; Gong, 1999; Yuan, 1999) while $\Delta$Np73 is rapidly degraded (Maisse et al., 2004). $\Delta$Np63 expression is transcriptionally reduced by p53 suggesting that it does not inhibit the tumour suppression activity of p53 and TAp73 in the same way. These observations suggest an important differential role for these isomers in carcinogenesis (Melino, 2002; Melino et al., 2003; Stiewe, 2002; Zaika, 2002).

The role of p63 and p73 in cell cycle and apoptosis suggests that their modification can contribute to enhanced cell death in tumours. In addition, several mutations in p63 are associated with genetic epidermal syndromes while p73 overexpression is sufficient to trigger neuronal differentiation. Accordingly, modification of p63 or p73 stability may be a therapeutic strategy in the treatment of cancer and/or developmental disorders.

While ubiquitination and proteasomal-dependent degradation of p53 is regulated by its transcriptional target MDM2, the regulation of p73 and p63 protein degradation is controlled by distinct E3 ligases. To date very little is known of the molecular mechanisms underlying the regulation of p63 and p73 protein steady state levels and their modulation as a possible therapeutic strategy has not been fully explored. While some approaches have sought to use proteosome inhibitors to inhibit the degradation of p53-family proteins and thus induce apoptosis, in clinical trials these inhibitors have been found to have very little specificity and lead to up-regulation of a large number of proteins. Moreover, while a number of cancer therapeutic strategies have targeted p53, more than 50% of tumours are p53 deficient. Accordingly, there is a need for therapeutics that can target p53 independent pathways.

SUMMARY OF THE INVENTION

The present invention identifies that a modulation of Itch activity can provide an important cellular response for therapy of various disorders. In particular, the present invention demonstrates that an inhibition of Itch activity regulates apoptosis in a cell.

Accordingly, in a first aspect of the invention, there is provided a method of modulating apoptosis in a cell comprising the step of decreasing or otherwise altering the functional activity of Itch polypeptide or the nucleic acid encoding it. The changes in Itch activity results in an altered stability of p63 and p73 proteins, as well as their activity, such as for example their ability to regulate apoptosis. Suitably, said modulation of apoptosis confers death in a cell.

Suitably, the invention provides a method of inducing apoptosis in a cell by inhibiting Itch.

Preferably, Itch inhibition is through inhibition of Itch activity. In another embodiment, Itch inhibition is through inhibition of Itch mRNA expression through techniques such as RNAi.

In addition, the present invention identifies that the inhibition of Itch activity sensitises cells to cell death induced by cytotoxic agents such as DNA damaging agents. A large number of DNA damaging agents will be familiar to those skilled in the art. In particular, treatment with DNA damaging compounds (such as, for example, cisplatin, etoposide, doxorubicin, gamma radiation, campodacin, taxol) as well as treatment with UV results in rapid downregulation of Itch. Accordingly, the present invention provides a method for sensitising cells to DNA damaging agents through inhibition of Itch activity. Such methods can be useful in the treatment of cancer.

Accordingly, in a further aspect of the invention there is provided a method of treating cancer comprising administering an agent which inhibits Itch activity simultaneously or sequentially with a DNA damaging agent. Suitable DNA damaging agents include cisplatin, etoposide, doxorubicin, gamma radiation, campodacin, taxol as well as treatment with UV.

Suitably said method comprises the steps of treating a cell with an RNAi molecule capable of interfering with Itch mRNA such that Itch expression is decreased and treating the cells with a DNA damaging agent. Suitable RNAi molecules are disclosed herein.

The present invention further identifies an interaction between Itch, a Hect ubiquitin-protein ligase, and the proteins p63 and p73. In particular, the description herein demonstrates that Itch ubiquitinates p73 targetting it for proteosomal destruction. Moreover, it has been determined that Itch selectively binds and ubiquitinates p73 but not p53. Prior to the present description, very little was known about the molecular mechanisms underlying the regulation of p73 protein steady state levels. MDM2, the E3 ubiquitin ligase that regulates the degradation of the cognate protein p53 via a proteasomal dependent pathway, binds to p73 but does not promote its degradation (Balint, 1999; Dobbelstein, 1999; Lohrum, 1999; Ongkeko, 1999; Zeng, 1999).

Itch ubiquitinates upon binding. In particular, Itch binds and ubiquitinates proteins including the TA and ΔN isoforms of p73. Ubiquitination determines proteasome-dependent degradation of proteins. Where TA and ΔN isoforms are ubiquitinated by Itch, they are targeted for destruction leading to reduced levels of the proteins in the cell and therefore decreasing cell cycle arrest and apoptosis. Conversely, where ubiquitination of these proteins is reduced by inhibiting Itch activity, the level of protein in the cell increases therefore enhancing cell cycle arrest and apoptosis. Itch is therefore a drug target for the regulation of this pathway and the treatment of, inter alia, conditions such as cancer where enhanced apoptosis is desirable.

Accordingly, the present invention identifies that downregulation of Itch activity leads to an increased level of regulated proteins, including p73, which results in increased cell cycle arrest and apoptosis. In addition, it is shown that, upon DNA damage, Itch itself is down-regulated, allowing p73 protein levels to rise and thus interfere with p73 function.

In another aspect of the present invention, therefore, there is provided a method of modulating p63 or p73 stability in a cell comprising modulating Itch activity or expression.

As shown herein, Itch binds to ΔNp63, TAp73, ΔNp73 and to a lesser extent TAp63. Accordingly, one suitable method of modulating Itch activity is to modify the binding of Itch to ΔNp63, TAp73 and ΔNp73. Moreover, it is demonstrated herein that Itch binding to p63 and p73 occurs between the PY motif of p63 and p73 and the WW domain of Itch. Accordingly, one suitable method for modulating Itch activity is to disrupt binding between PY and WW.

In one embodiment, the method of modulating p63 or p73 stability may be through modulating Itch expression. Suitable methods of modulating gene expression will be familiar to those skilled in the art. Such methods include, for example, RNAi. Suitable RNAi molecules and methods for modulating expression of Itch are described herein. RNAi methods result in decreased levels of expression of the target protein. RNAi inhibition of Itch expression has been demonstrated herein to downregulate Itch expression and result in stabilisation of its substrates including TA and ΔN p73 which, in turn, leads to increased levels of p73.

Conversely, Itch over-expression can be used to promote decreased stability of its substrates, including TA and ΔN p73, leading to their rapid degradation.

Accordingly in another aspect of the invention there is provided RNAi molecules for use in a method of modulating p63 or p73 stability.

DNA damage through agents such as cisplatin, etoposide, doxorubicin, gamma radiation, campodacin, taxol, as well as treatment with UV results in rapid downregulation of Itch which correlates with increases in p73 levels. This increase in p73 levels is thought to be through protein stabilisation. The invention further provides an assay method for identifying one or more agents that modulate the activity and/or expression of Itch.

Suitably such assay methods enable agents which modify the functional activity of Itch by modifying its ubiquitinase activity to be identified. Suitable assays for measuring ubiquitination of a substrate are described herein.

Accordingly, there is provided a method for identifying an agent which modulates Itch activity comprising:

incubating an agent or agents to be tested with an Itch molecule in the presence of a reconstituted in vitro ubiquitination system, determining the amount of ubiquitin ligated to Itch in the presence of the agent or agents to be tested; and selecting those agents which modulate the amount of ubiquitin ligated to Itch compared to the amount of ubiquitin ligated to Itch in the absence of the agent or agents to be tested.

Suitably, an agent identified as a modulator of Itch activity can be further assayed to determine its interaction with p63/p73. In particular, such assays may identify those agents which modulate the levels or activity of p63 or p73. Suitable assays for determining said interaction include cell based assays in which the candidate agent is incubated in cells and the expression levels of p63/p73 is determined by Western Blot analysis, for example.

There is also provided a method for identifying an agent which modulates Itch activity on its substrates, comprising: incubating an agent or agents to be tested with an Itch molecule and a ΔNp63, TAp73 or a ΔNp73 molecule in the presence of a reconstituted in vitro ubiquitination system, determining the presence of ubiquitinated forms of ΔNp63, TAp73 or a ΔNp73 in the presence of the agent or agents to be tested; and selecting those agents which modulate the amount of ubiquitinated forms of ΔNp63, TAp73 or a ΔNp73 compared to the amount of said ubiquitinated forms obtained in the absence of the agent or agents to be tested.

By a reconstituted in vitro ubiquitination system, is meant a selection of reagents which enable a ubiquitination reaction to occur. Such reagents include, for example ubiquitin, an ATP source, E2, E1 and so forth. Examples of suitable systems are described herein.

Ubiquitinated forms of a protein may be detectable by measuring the presence of higher molecular weight forms of ΔNp63, TAp73 or ΔNp73 proteins. Alternative methods for detecting the ubiquitination of proteins are familiar to those skilled in the art. Suitable methods are described, for example, in WO 01/75145.

In another aspect, the invention provides a method for identifying one or more agents capable of modulating the stability of p63 or p73, comprising the steps of:

(a) incubating an Itch molecule with the agent or agents to be assessed; and (b) identifying those agents which influence the binding of Itch to p63 or p73.

Preferably, the agent or agents bind to the Itch molecule and/or the p63 or p73 molecule and, in particular, a ΔNp63, TAp73 or a ΔNp73 molecule.

Accordingly, there is also provided a method for identifying a lead agent for a pharmaceutical useful in the treatment of disease, comprising: incubating an agent or agents to be tested with an Itch molecule and a ΔNp63, TAp73 or a ΔNp73 molecule, under conditions in which, but for the presence of the agent or agents to be tested, Itch and ΔNp63, TAp73 or a ΔNp73 form a complex with a reference binding affinity;

determining the binding affinity of the complex of Itch and ΔNp63, TAp73 or a ΔNp73 in the presence of the agent or agents to be tested; and selecting those agents which modulate the binding affinity of the complex with respect to the reference binding affinity.

In one embodiment of the methods described herein, whole molecules may be used. In another embodiment, the binding parts of the molecules may be used. As set out herein, the WW domains of Itch are involved in binding ΔNp63, TAp73 or ΔNp73. Similarly the PPxY motif is the region within ΔNp63, TAp73 or ΔNp73 that interacts with the WW domain. Accordingly, the method of the invention may utilise fragments of the molecules comprising the appropriate binding domains.

In another aspect, the method for identifying agents which modulate the functional activity of Itch by modulating its ubiquitinase activity can be performed in vivo in a cell. In cell based assays, interactions may be measured in a relevant environment. Such a method suitably comprises: transfecting cells with expression systems to ensure expression of Itch and ΔNp63, TAp73 or ΔNp73 and ubiquitin and subsequently determining the presence of ubiquitin-ΔNp63, TAp73 or ΔNp73 conjugates. Suitable methods are disclosed herein. Molecular interactions are detectable, for example, by two-hybrid screens, in which a gene expressing a detectable marker is placed under the control of a promoter which is responsive to a transcription factor assembled by the interaction of the two molecules under test. Other assays may be used to detect molecular interactions, for example co-immunoprecipitation from transfected Hek293 cell lysates.

In a further aspect, the invention relates to an agent identifiable by the method of any aspect of the invention, capable of modulating the binding of Itch to ΔNp63, TAp73 or ΔNp73, modulating the ubiquitinase activity of Itch or modulating the stability of ΔNp63, TAp73 or ΔNp73. For example, such an agent may be small molecule inhibitor, an antibody, which is preferably specific for Itch, a polypeptide, such as a polypeptide aptamer, or an Itch molecule such as a dominant negative mutant of Itch. Other suitable agents are described herein.

In addition, mutants of both binding the PY motif of p73 and the WW domain of Itch have been generated and result in loss of binding and ubiquitination of p73. Accordingly, other suitable agents include these mutant molecules.

In addition, the invention provides research tools comprising modified cell lines which enable substances to be tested for their ability to modulate the activity of Itch on p73.

The invention moreover provides a method for modulating the activity of Itch in a cell, comprising administering to the cell an agent as set forth above, as well as a pharmaceutical composition comprising, as active ingredient, a therapeutically effective amount of such and to a method for treating a condition associated with cell proliferation, comprising administering to a subject a therapeutically effective amount of said agent.

Preferably, the disease is a disease involving uncontrolled cell proliferation.

In a further aspect, the present invention provides a method of treating a cancer in a patient, said method comprising the step of administering to said patient a therapeutically effective amount of an agent that is capable of modulating the p73 ubiquitination activity of Itch.

p73 is a critical regulator of the response to chemotherapy in several tumour cell lines (Irwin et al., 2003). This implies that treatment of chemotherapy-resistant tumours with Itch inhibitors would result in augmented p73 expression levels and consequent sensitization to chemotherapy. Accordingly, in one embodiment, said cancer is a chemotherapy resistant tumour.

Itch is activated by JNKs to induce the degradation of c-Jun. Both JNK and c-Jun are involved in the regulation of the cellular response to DNA damage. Therefore, inhibition of Itch would have an impact on how cells respond to DNA damage. In particular, it could result in c-Jun (and p73) dependent sensitization to the cytotoxic effects of chemotherapeutic agents.

In particular, it is shown herein that Itch selectively binds and ubiquitinates p73 but not p53. Accordingly, the method of the present invention is particularly suitable for treating cells in a p53 independent manner. This is particularly relevant in the context of enhancing the response to chemotherapy in resistant tumours containing mutant p53. As p53 is inactivated in >50% tumours, activation of p73 in tumour cells is proposed as a good mechanism of targeting tumour cells.

Up-regulation of TAp73 by down-regulation of Itch results in increased in vivo sensitivity to drugs. We therefore propose that pharmacological inhibition of Itch can be used to sensitize tumour cells to treatment. The effect of Itch on other targets such as c-Jun might contribute to the final effect on DNA damage-dependent apoptosis. In addition a specific Itch inhibitor can be an extremely valuable tool for scientist in the field.

p63 is expressed in the staminal cell compartment of the epidermis, and its mouse knockout results in the total absence of epidermis. In addition, altered expression of p63 proteins have been identified in skin cancers and a deregulation of p63 in skin diseases (psoriasis, ichthyosis) has been shown.

Mutations in p63 are associated with a number of developmental abnormalities including a combination of hand and foot anomalies and mammary gland aplasia or hypoplasia which characterize the following syndromes: ectrodactyl), ectodermal dysplasia, clefting (EEC) syndrome, ulnar-mammary syndrome, limb-mammary syndrome (LMS), ankyloblepharon, ectodermal dysplasia, clefting (AEC) syndrome, nonsyndromic split hand/foot malformation (SHFM) and acro-dermato-ungual-lacrimal-tooth (ADULT) syndrome.

In particular, mutations in the p63 gene in 3q27 have been detected in patients with EEC syndrome, in nonsyndromic split hand/foot malformation (SHFM) and subsequently in ankyloblepharon, ectodermal dysplasia, clefting (AEC) syndrome, in ADULT syndrome, and in LMS. These are described, for example, in Han G. Brunner, Ben C. J. Hamel, Hans van Bokhoven. American Journal of Medical Genetics. Volume 112, Issue 3, Pages 284-290)

More recently, additional mutations were found in another syndrome characterized by similar clinical characteristics, the Rapp Hodgkin syndrome. Other syndromes, such as the lacrimo-anriculo-dento-digital (LADD) syndrome, the ectrodactyly cleft palate (ECP) syndrome, the recessive Bowen-Armstrong and the curly hair ankyloblepharon nail dysplasia syndrome (CHANDS) syndromes may also be associated with p63 mutations.

Other skin diseases include acute or chronic skin diseases such as psoriasis, icthyosis, seborrheic keratoses and Bowens lesions. Increased expression of p63 has been identified for seborrheic keratoses and Bowens lesions. While this was mostly restricted to the basal layer, significant diffuse staining was also noted. Moreover, p63 expression is increased in squamous cell carcinomas.

Accordingly, in another aspect, the present invention provides a method of treating epidermal development disorders or skin diseases in a patient, said method comprising the step of administering to said patient a therapeutically effective amount of an agent that is capable of modulating the p63 ubiquitination activity of Itch.

In one embodiment, there is provided a method of treating a patient so as to regenerate the skin where it is severely burnt.

Molecules able to regulate the enzymatic activity of Itch might have a potential use in epidermis. This is based on two findings: (i) Itch is highly expressed in epidermis, (ii) Itch regulates the ubiquitinin-dependent degradation of TAp63 and ΔNp63, two proteins that are crucial for skin development and skin homeostasis, as described herein.

Consequently, molecules that regulate (inhibition or induction) of Itch activity, will have a profound effect on the skin and may affect epidermal homeostasis by increasing/reducing the proliferation status. This will predict a potential use both in psoriasis and ichthyosis and allow better in vitro growth and terminal differentiation of keratinocytes and artificial skin.

Accordingly, in a further aspect there is provided a method of increasing sensitivity of a tumour cell to a chemotherapeutic agent comprising reducing Itch activity, expression levels or function. Suitably, reduction of Itch is by RNAi. In another embodiment, Itch activity on p73 is through disrupting the association through the WW domains.

Specific antibodies for Itch could be used to predict tumours with different chemosensitivity, according to the ability of Itch to regulate p63/p73 mediated DNA damage and chemosensitivity. Specific methods to identify mRNA of Itch, such as PCR procedures, could be used for the same purpose. The relative expression of Itch and its substrates (TAp73, ΔNp73, ΔNp63) could be used as a chemosensitivity predictor to tailor individual cancer chemotherapy.

Figure 1A:
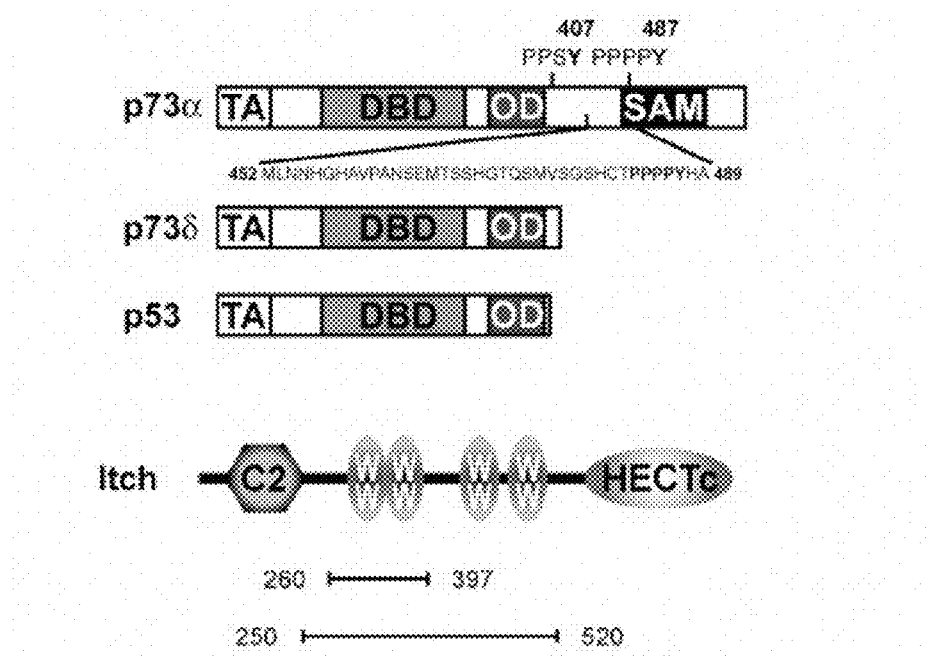
FIG. 1 p73 binds to Itch.

(A) Schematic representation of the modular structure of the p73α, p73δ, p53 and Itch proteins. The main structural domains are indicated: transactivation domain (TA), DNA binding domain (DBD), oligomerization domain (OD), sterile alpha motif (SAM), amino-terminal C2 domain (C2), WW domains (WW), carboxyl-terminal Hect domain (HECTc). The p73 region from Met452 to Ala489, containing the PPxY motif, used as bait in the phage library panning experiment, is also shown. Bars indicate the regions of Itch expressed by the clones selected in the screening.

(B) T7 plaques from the unselected library and from the enriched phage pool, transferred to a cellulose membrane and probed with GST-PY are shown. PCR demonstrating the enrichment of clones containing the Itch WW domains is shown in the lower panel.

(C) GST pull down. Hek293 cells were transfected with HA TAp73α (TAp73α) or empty vector (pCDNA) and lysates were incubated with GST alone, or a GST fusion protein containing the four WW domains of Itch (GST-WW). The retained proteins were detected with anti-p73 antibody (upper panel). The same blot was reprobed with anti-GST polyclonal serum (lower panel). Coimmunoprecipitation of overexpressed proteins: HA-TAp73α or HA TAp53 (D) or HA-ΔNp73α (E) or TAp73αY487F, TAp73αY407F and TAp73αY407F/Y487F (F) were transiently transfected in Hek293 cells with either Myc-Itch or Myc-Itch MUT expression vectors. Cells were treated with or without MG132 before lysis. Cell extracts were IP with anti-Myc antibody. The immune complexes were subjected to Western-blot analysis with anti-HA antibody (upper panels). The same blots were re-probed with anti-Myc antibody (middle panels). Aliquots of total cell extracts from unprocessed cells (25 µg/lane) were directly subjected to immuno-blot analysis with anti HA antibody (lower panels).

(G) Co-IP of endogenous p73 and Itch proteins. Cells were IP with antibodies against either p73 (mix of clones C17 and C20, Santa Cruz) or p53 (mix of clones D01 and 1801 Santa Cruz) and Western blot was performed with antibody against: Itch, p73, p53 and Actin. As a control, IP was performed also with an anti-Actin antibody.

FIG. 2 Itch ubiquitinates p73. (A) TAp73α and TAp73δ and p53 proteins were in vitro translated in the presence of [$^{35}$S] methionine and incubated with purified Itch (GST-Itch) or its catalytically inactive mutant (GST-Itch MUT) in the presence of ATP, ubiquitin, and bacterially expressed E1 and E2 (UbcH7). Lanes 10 to 12 show in vitro translation with the empty vector (pCDNA). Lanes 13 to 16 show an aliquot (1/10) of the in vitro translated proteins used in the ubiquitination reaction. To demonstrate that p73 ubiquitination could also occur in a more physiological system, Hek293 cells were transiently co-transfected with expression plasmids for HA tagged ubiquitin (Ub-HA), Flag-TAp73α or Flag-p53 (B) Flag-ΔNp73α (C) or Flag-TAp73αY487F, Flag-TAp73αY407F and Flag-TAp73αY407F/Y487F (D) and Myc-Itch or Myc-Itch MUT. 48 hours after transfection cells were treated with MG132 and then collected. Lysates were subjected to IP using an anti-Flag antibody. Immune complexes were revealed with anti-HA antibody (upper panels). No Ub-HA-conjugates are present when Ub-HA is omitted from the reaction (B-lanes 10-18). The p73 and p53 protein expression levels are demonstrated by probing the same membranes with anti-Flag antibodies (middle panels) and those of Itch by probing the same membrane with anti-Myc antibodies (lower panels).

FIG. 3 Effect of Itch expression on the steady-state levels of p73. (A) Hek293 cells were transfected with either HA-TAp73α and p53 or HA-TAp73α (A) or Flag-TAp73αY487F, Flag-TAp73αY407F and Flag-TAp73αY407F/Y487F (B) together with either Myc-Itch or Myc-Itch MUT. 48 hours after transfection, cells were treated or not with MG132. Equal amounts of total protein cell lysates were subjected to Western blotting analysis using anti-HA antibody or anti Flag antibody (upper rows) to detect the steady state levels of p73s and p53 proteins. The same blots were re-probed with anti-Myc antibody in order to detect the expression levels of Itch (middle rows) and with anti-Actin antibody to show equal loading (lower rows). $^{35}S$ pulse-chase. H1299 cells were transfected with HA-TAp73α (C) or HA-ΔNp73α (D) together with Myc-Itch or pCDNA-Myc. 48 hours post-transfection cells were labelled with 250 μCi/ml of Redivue PRO-MIX (L-[$^{35}$S] in vitro cell labelling mix). Unlabeled Met and Cys (1 mg/ml) were added and cells were collected at the indicated time points. Immunoprecipitation were performed with anti-HA (Y-11) polyclonal antibody. Immunoprecipitates were washed and run on a SDS-PAGE and detected by autoradiography. For cycloheximide blocking experiments Hek293 cells were transfected with either HATAp73α (E), HA-ΔNp73α (F), or HA-p53 (G) together with either Myc-Itch or pCDNAMyc. 24 hours after transfection cells were treated with cycloheximide and collected at different time points. Equal amounts of total protein cell lysates were subjected to Western blotting analysis using anti-HA antibody. To demonstrate equal loading the same blots were stripped and re-probed with anti-β-Tubulin or anti-Hsp-70 antibodies for p73s and p53 blots respectively. (C) Western blots were subjected to densitometric analysis and results were normalized based on β-Tubulin or Hsp-70 expression levels respectively and reported in graphical form (lower panels).

FIG. 4 Effects of Itch downregulation on p73 protein levels.

(A) Saos-2-TAp73α inducible cells were transfected with siRNA oligonucleotides targetting the Itch sequence or with a scrambled oligonucleotide. 48 hours later cells were induced to express TAp73α for the indicated time points with doxycycline (inducer). p73 levels increase more rapidly and reach higher levels when Itch is down regulated. The lower panel shows endogenous Itch levels. Graphs show densitometric analysis of the p73 western blots normalized for β-Tubulin.

(B) Saos-2-TAp73α inducible cells were transfected with oligos targetting the Itch sequence or with a scrambled oligo. Cells were induced to express TAp73α for 14 hours with doxycycline, the inducer was removed and cells collected at the indicated time points. p73 levels decay more rapidly in cells transfected with the scrambled oligo compared to those in which Itch is down regulated. The lower panel shows endogenous Itch levels. Graphs show densitometric analysis of the p73 Western blots normalized for β-Tubulin.

(C) Saos-2 cells transfected with oligos targeting the Itch sequence or with a scrambled oligo and collected 48 hours later. Itch down-regulation (lower panel) results in an increase of TA and ΔN p73a levels (upper panels).

(D) Western blot for endogenous p73 of wild type MEFs (MEF+/+), non-agouti-lethal 18H Itch deficient MEFs (MEF Itch-/-) and a spontaneously immortalized clone of these MEFs (MEF Itch-/- Immortalized). ΔNp73 levels (the only form detectable in these cells) are higher in MEFs Itch-/-. (E) Immortalized MEFs Itch-/- were transfected with Myc-Itch WT and collected 48 hours later. Re-introduction of Itch results in ΔNp73 downregulation.

Figure 5A:
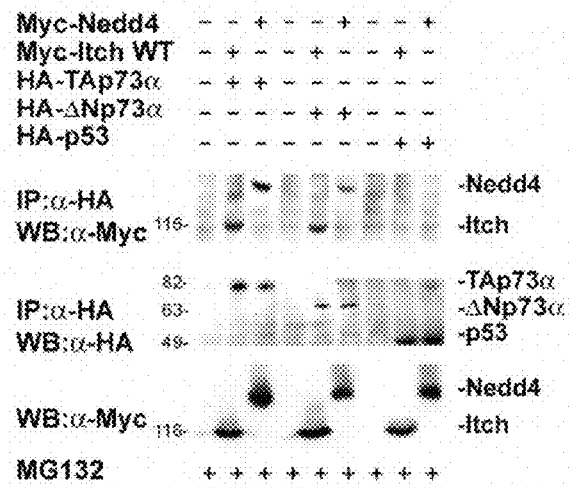

FIG. 5 Nedd4 binds p73 but fails to ubiquitinate it.

(A) Hek293 cells were transfected with HATAp73α, HA-ΔNp73α, HA-p53 or an empty vector together with Myc-Itch or Myc-Nedd4 in the presence of MG132. Cells were subjected to IP using anti-HA antibody and analysed by western blot using an antibody against Myc. Itch and Nedd4 co-IP with p73.

(B) Hek293 cells were transfected with HA-TAp73α, HA-ΔNp73α, or HA-p53 together with Myc-Itch or Myc-Nedd4. Cell extracts were analysed by western blot using an antibody against HA. Expression of Itch but not of Nedd4 results in TA and ΔN p73 down-regulation. (C) Cells transfected with the indicated plasmids together with a plasmid expressing HA tagged ubiquitin (Ub-HA) were analysed by western blot using an antibody against HA. Higher molecular bands characteristic of ubiquitination appear when Itch but not Nedd4 is overexpressed.

FIG. 6 Itch expression reduces the transcriptional activity of p73. H1299 cells were transfected with the indicated combinations of plasmids (at the different indicated ratios) encoding TAp73α, together with Myc-Itch WT (Itch wt) or Myc-Itch MUT (Itch Mut), or empty control vector (pCDNA) together with a Bax-(A-B) or MDM2-(C-D) or p21-(E-F) luciferase reporter plasmid and Renilla luciferase reporter plasmid. Cell extracts were prepared 36 hrs later and luciferase activity was determined. Results are represented as fold induction of luciferase activity as compared with the control cells. Histograms show the mean of three independent experiments; bars indicate standard deviation. (G) H1299 cells were transfected with HA-TAp73α together with Myc-Itch at the indicated ratios. Equal amounts of cell extracts were subjected to western blot with anti p21 antibody (upper panel), anti-HA (middle panel) and anti-Myc (lower panel).

FIG. 7 Itch is down regulated by DNA damaging agents. Saos-2 cells were treated with 2 μM doxorubicin (Doxo) for 24 or 48 hours then collected by trypsinization. Cells were lysed for western blotting (A) and half of the cells were ethanol fixed for apoptosis analysis (B). Western blots were performed with either anti-Itch (upper panel) or anti-p73 (lower panel) antibodies. Blots were stripped and re-probed with anti Lamin B antibody to show equal loading. Apoptosis was evaluated by flow cytometric analysis of PI stained cells. Non-treated controls (N.T.) are shown. H1299 cells transfected with HA-TAp73α (Con) are loaded as a control for p73 western blot.

(C) Western blot using anti-Itch antibody on Hela, H1299, Hek293 and Saos-2 cells treated for 24 hours with 2 μM doxorubicin. Blots were stripped and re-probed with anti-β-Tubulin antibody to show equal loading.

(D) Western blot using anti-Itch antibody on Saos-2 cells treated for 24 and 48 hours with either 15 μM etoposide (Etopo) or 5 μM cisplatin (Cisp). Non-treated control cells are also shown (N.T.). Blots were stripped and re-probed with anti p73 antibody and Lamin B antibody to show equal loading.

(E) Saos-2-TAp73α (upper panel) or Saos-2-ΔNp73α (lower panel) were induced with doxycycline for 14 hours. Doxycycline was then removed and cells were treated with the indicated drugs and analysed at the indicated time points by western blot using anti-HA antibody. Blots were re-probed with anti-β-Tubulin to show equal loading.

(F) Saos-2-ΔNp73α were transfected with oligos for siRNA against the Itch sequence or with a scrambled sequence and then induced with doxycycline for 14 hours. Doxycycline was then removed and cells were treated with doxorubicin and analysed at the indicated time points by western blot using anti-HA antibody. Blots were re-probed with anti-β-Tubulin to show equal loading.

Figure 8:
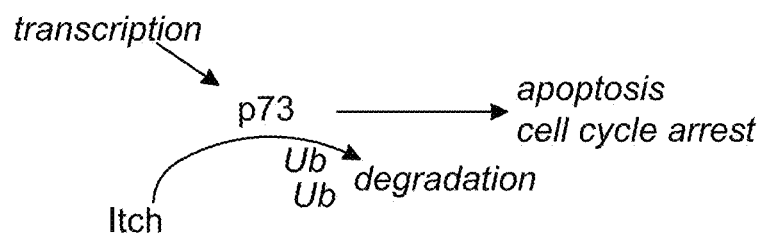
Figure 8:
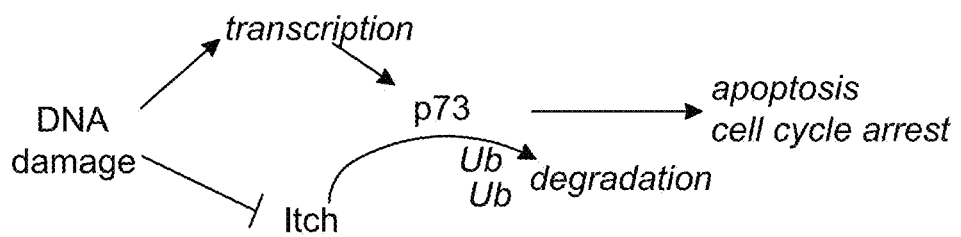

FIG. 8 Itch controls p73 levels in resting conditions and in response to DNA damage.

(A) Schematic representation of the functional interaction between p73 and Itch. Under nonstressed conditions basal levels of both TAp73 and ΔNp73 are kept low; in this situation Itch binds to p73 and promotes its ubiquitination and proteasome dependent degradation.

(B) In response to DNA damage Itch is rapidly degraded, reducing p73 turn over. TAp73 levels increase while ΔNp73 remain low due to the activation of a DNA damage dependent ΔN specific degradation pathway. The final outcome is the induction of cell cycle arrest and apoptosis by p73.

Figure 9:
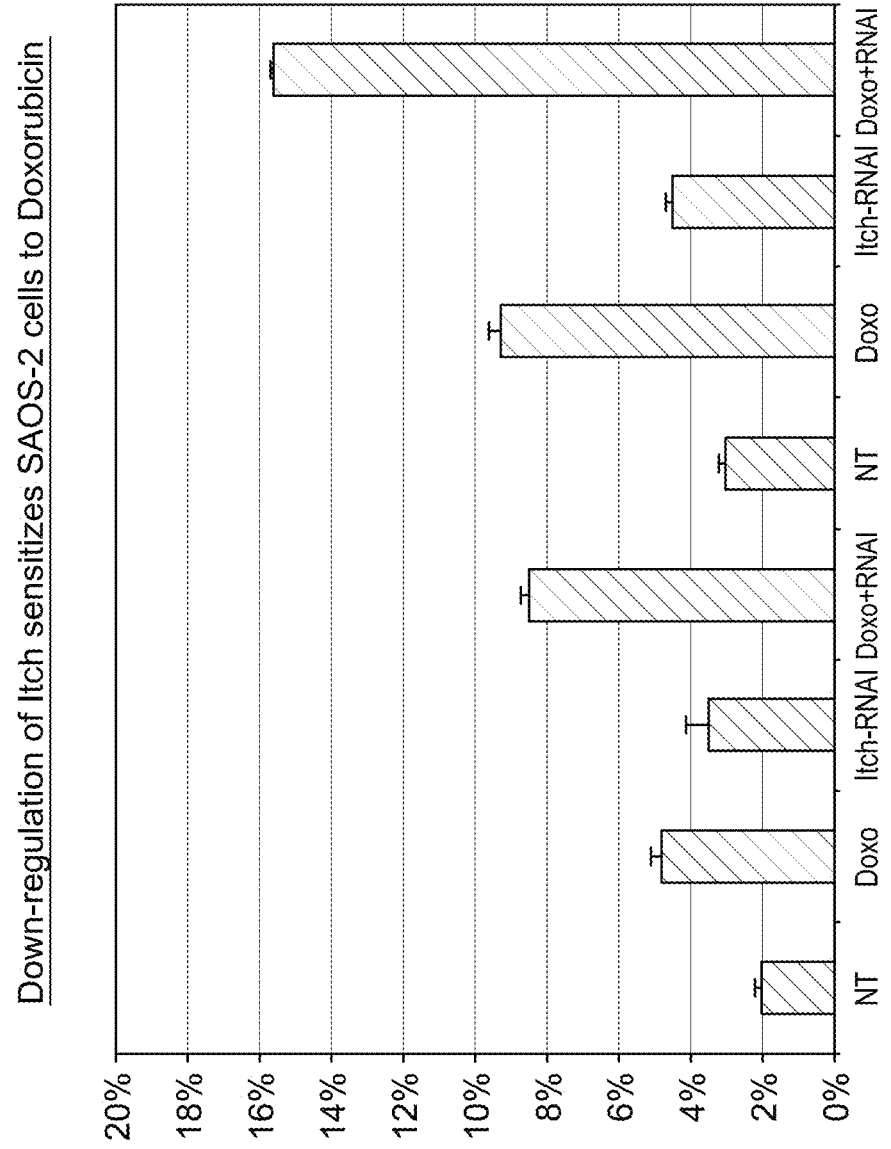

FIG. 9 shows Saos-2 cells were transfected or not with Itch-specific siRNA oligos and then either treated or not with doxorubicin (2 μM). After 24 hours (bars 1-4) and 48 hours (bars 5-8) cells were trypsinized and incubated with propidium iodide to quantize cell death. The histograms represent the mean results of three independent experiments.

Figure 10:
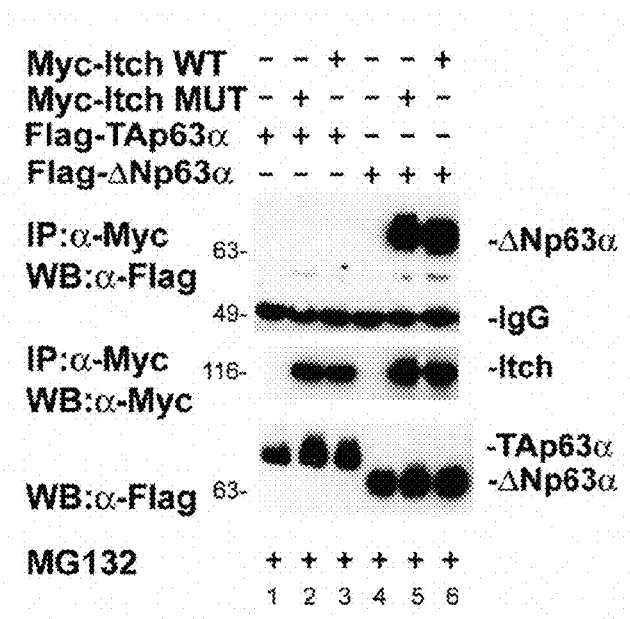

FIG. 10 shows ITCH interacts with p63. 293T cells were transfected with different combinations of expression vectors for Myc-tagged WT ITCH (Myc-ITCH WT), enzymatically inactive ITCH (Myc-ITCH MUT), Flag-tagged TAp63α (Flag-TAp63α) and ΔNp63α (Flag-ΔNp63α). Anti-Myc immunoprecipitates were probed with anti-Flag antibodies. Top panel shows co-immunoprecipitated proteins. Middle panel shows ITCH levels in the immunoprecipitates. Lower panel shows p63 levels in the input lysates. Experiments were carried out in the presence of the proteasome inhibitor MG132

Figure 11:
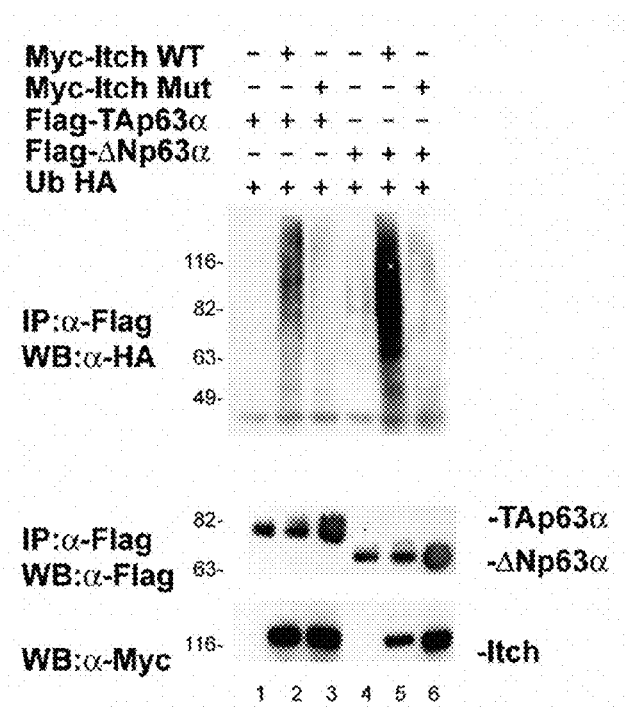

FIG. 11 shows ITCH induces the ubiquitination of ΔNp63α. 293T cells were transfected with vectors expressing Myc-tagged WT ITCH (Myc-ITCH WT), enzymatically inactive ITCH (Myc-ITCH MUT), Flag-tagged TAp63α (Flag-TAp63α), ΔNp63α (Flag-ΔNp63α) and HA-tagged ubiquitin (Ub HA). Lysates were immunoprecipitated with anti-Flag antibody and probed with anti-HA antibody. Top panel shows ubiquitin-conjugated p63 proteins. Middle panel shows p63 levels in the immunoprecipitates. Lower panel shows ITCH levels in the input lysates. Experiments were carried out in the presence of the proteasome inhibitor MG132.

Figure 12:
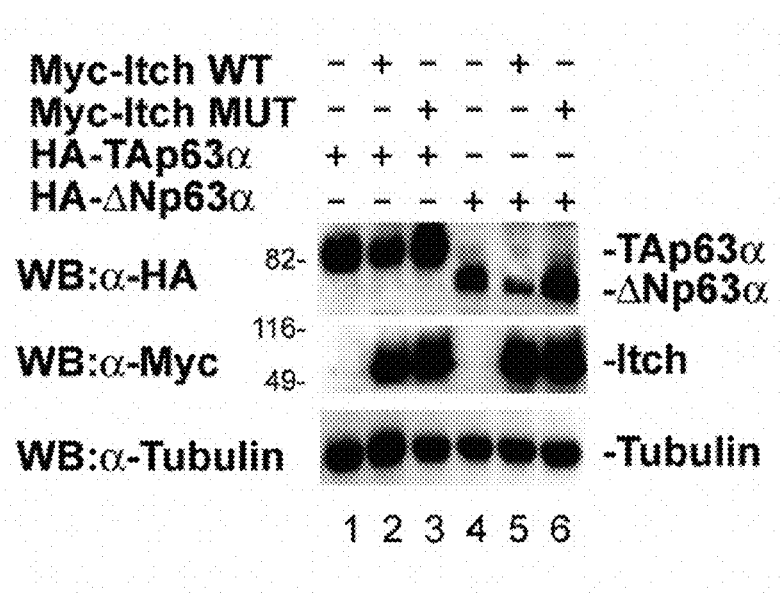

FIG. 12 shows ITCH over-expression causes ΔNp63α downregulation. 293T cells were transfected with vectors expressing Myc-tagged WT ITCH (Myc-ITCH WT), enzymatically inactive ITCH (Myc-ITCH MUT), Flag-tagged TAp63α (Flag-TAp63α) and ΔNp63α (Flag-ΔNp63α) and analyzed for p63 steady state levels using anti-Flag antibody (upper panel). Middle panel shows ITCH levels, while lower panel shows tubulin levels as loading control.

Figure 13:
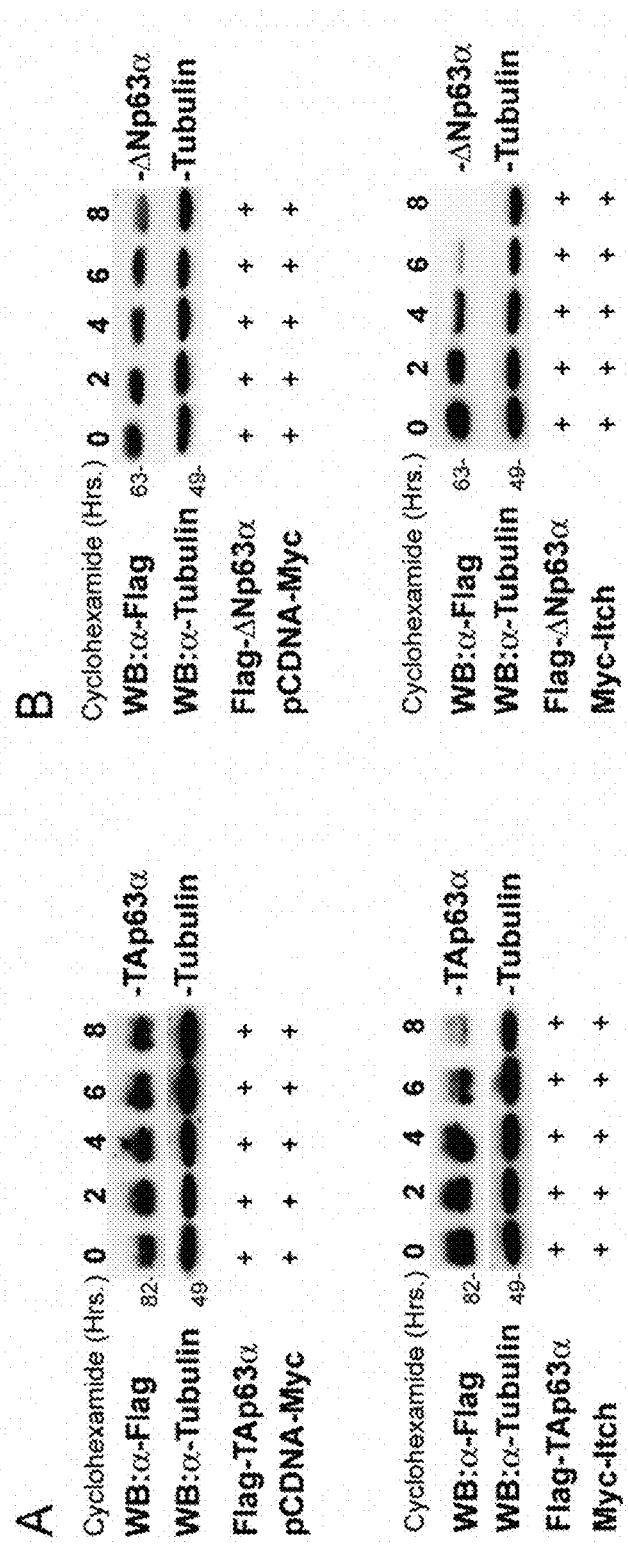

FIG. 13 shows ITCH selectively regulates the half-life of ΔNp63α. (A) 293T cells were transfected with Flag-tagged TAp63α expression vector in the presence of either control vector (top panel) or Myc-tagged WT ITCH (Myc-ITCH WT, lower panel) expression vector. 24 hours after transfection cells were incubated with cycloheximide and at the indicated different time points were harvested, lysed and analyzed for p63 levels using an anti-Flag antibody. (B) 293T cells were transfected with Flag-tagged ΔN p63α expression vector in the presence of either control vector (top panel) or Myc-tagged WT ITCH (Myc-ITCH WT, lower panel) expression vector. 24 hours after transfection cells were incubated with cycloheximide (20 μg/ml) and at the indicated different time points were harvested, lysed and analyzed for p63 levels using an anti-Flag antibody. In all cases, Tubulin levels were measured as loading control.

Figure 14:
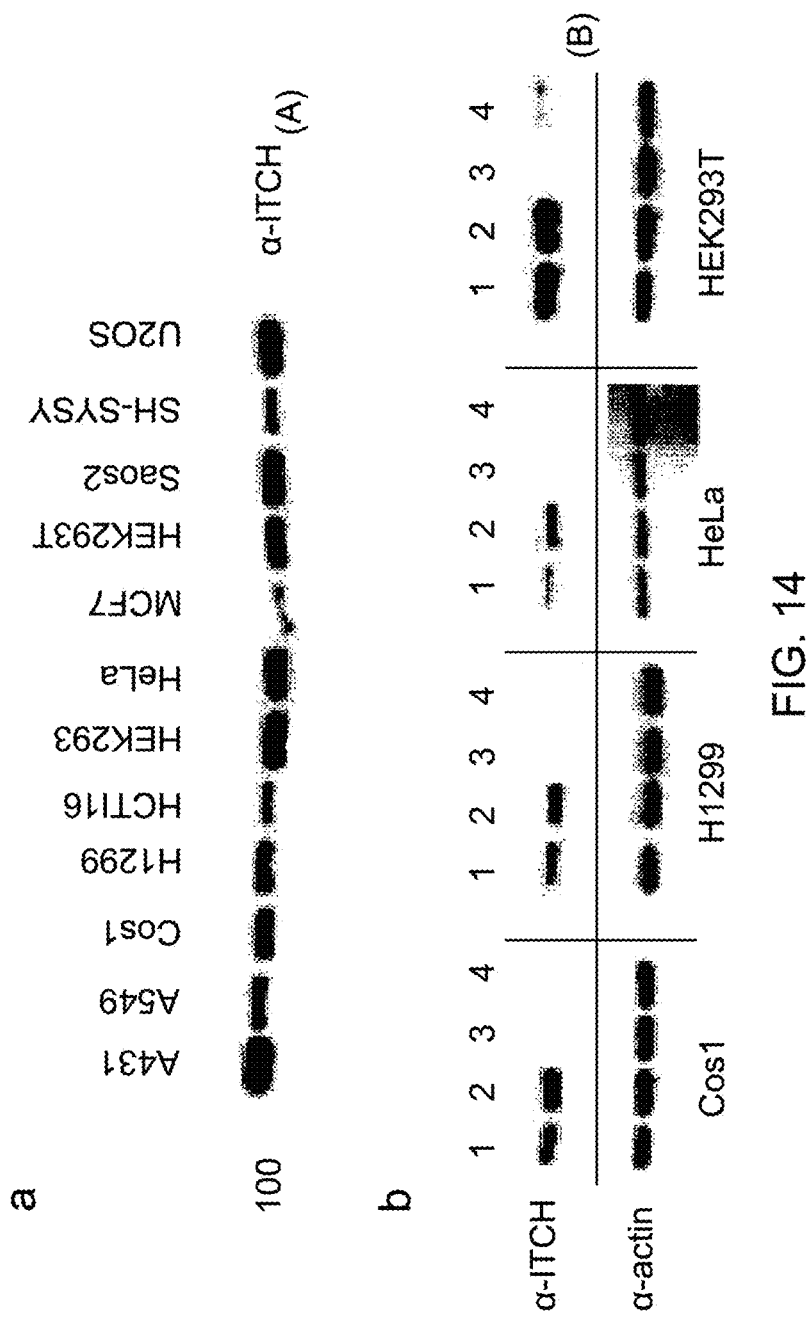

FIG. 14 (A) Western blot of 12 cell lines showing Itch expression (B) effect of shRNA (oligonucleotides no. 2 and 18) on Itch levels in (i) cos1, (ii) h1299, (iii) HeLa, and (iv) HEK293T 1=untransfected cells; 2=cells transfected with scrambled RNA; 3=cells transfected with shRNA clone 2; 4=cells transfected with shRNA clone 18.

Figure 15:
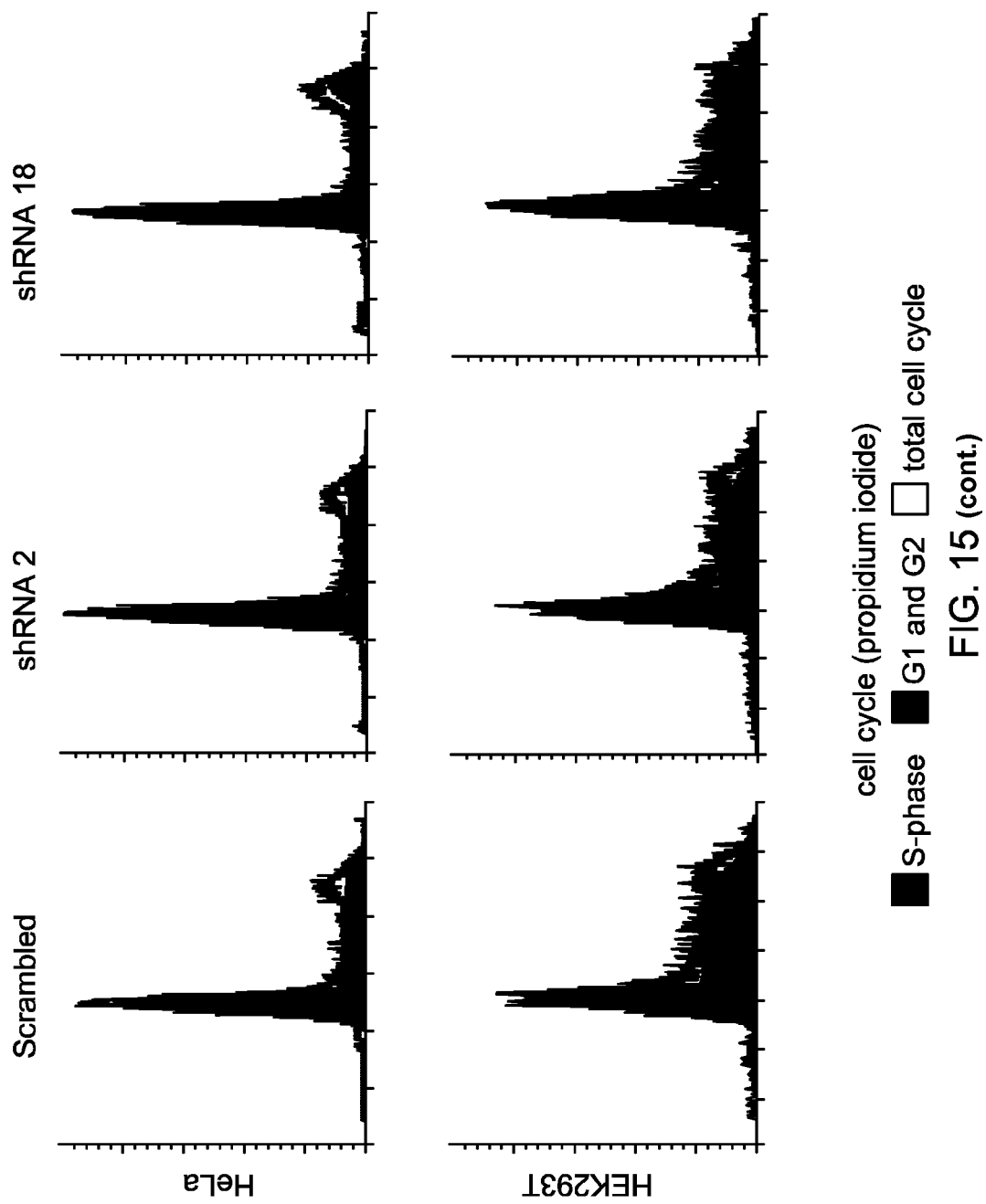
Figure 16:
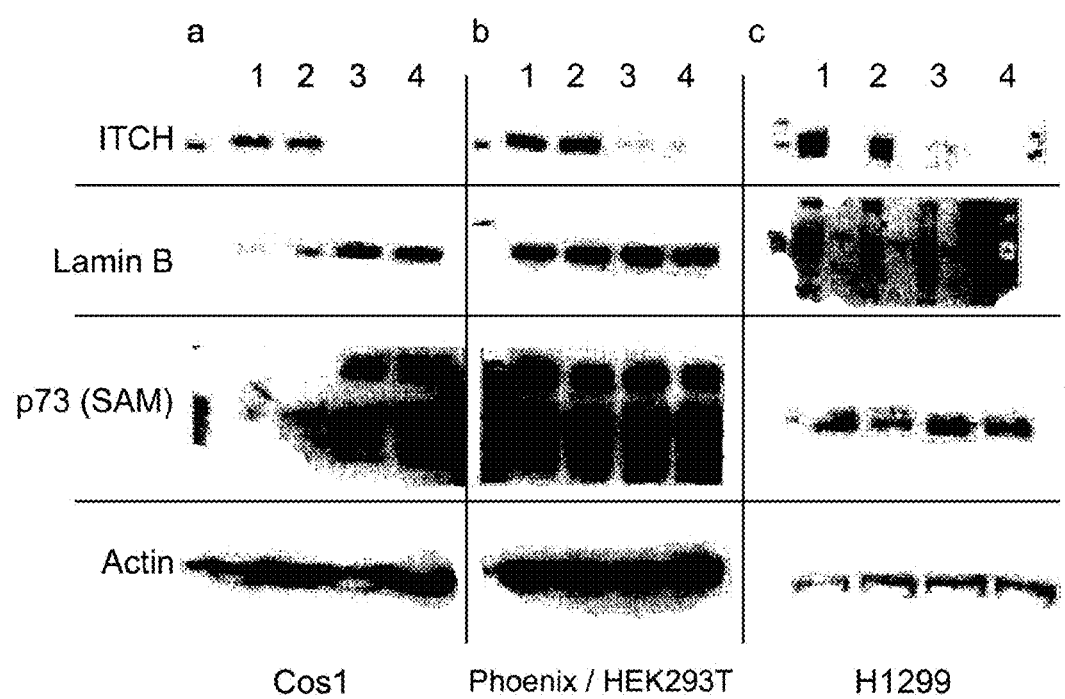

FIG. 15 Histograms showing cell cycle of cells transfected with scrambled, or shRNA against Itch 48 hours after transfection, (a) Cos1, (b) H1299, (c) HEK293T FIG. 16 Cells showing downregulation of Itch in response to transfection with shRNA targeted to Itch, and increased p73 levels, (a) Cos1, (b) HEK293T, (c) H1299

Figure 17:
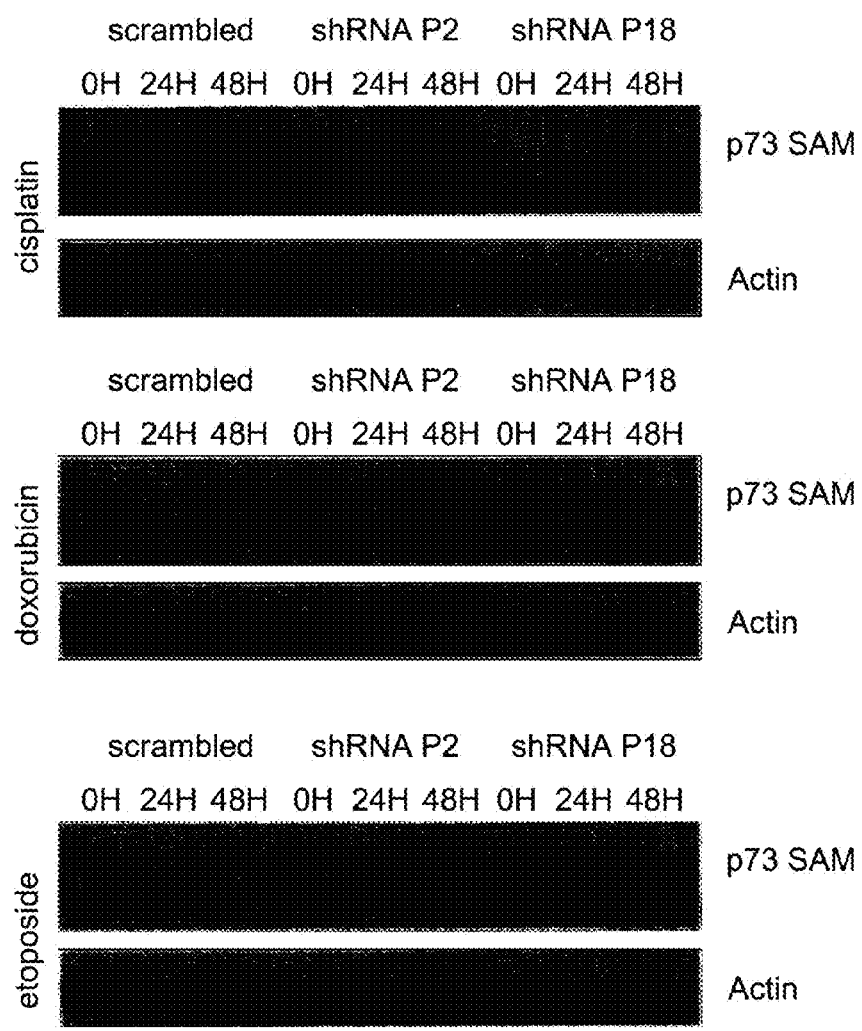

FIG. 17—Western blots of samples from H1299 cells, which were either transfected with scrambled or shRNA against Itch and then treated for 24 and 48 hours with DNA damaging agents. p73 levels in control and treated cells are shown.

Figure 18:
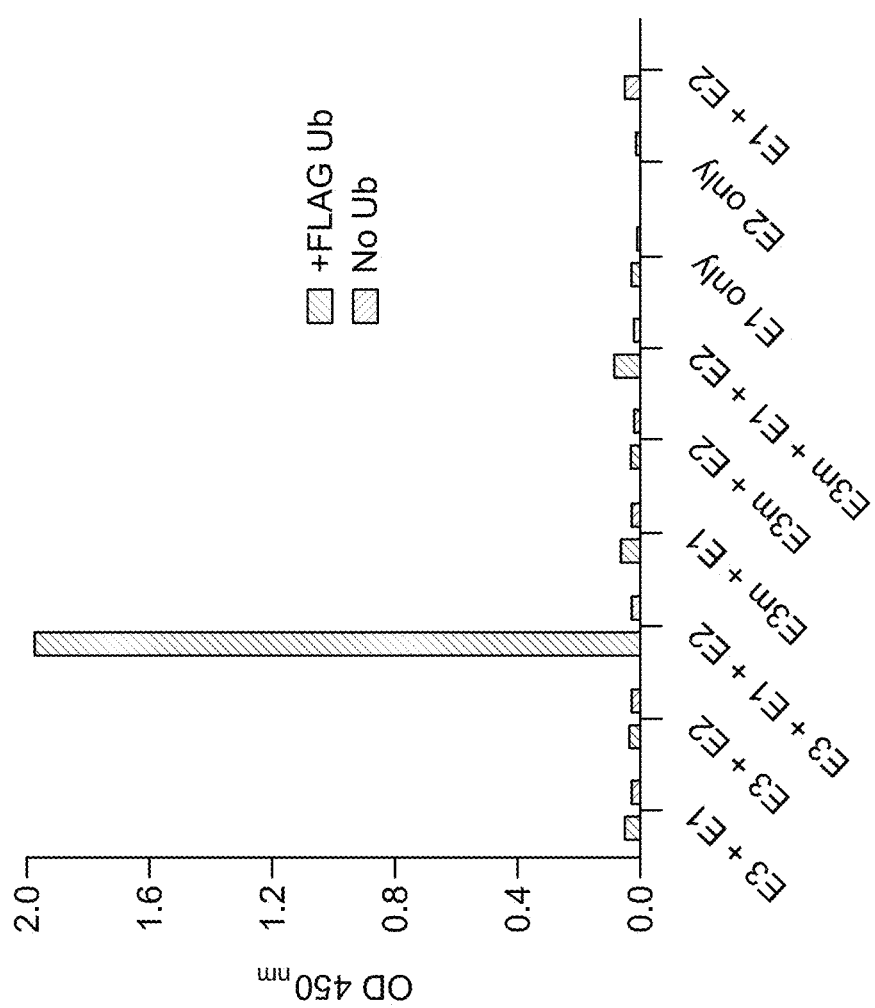

FIG. 18. ELISA assay for self-ubiquitination of Itch. Wild type Itch (E3) or catalytically inactivated Itch containing the point mutation C830A (E3m), were immobilised onto a glutathione-coated microtiter plate wells. Uncoated wells received coating buffer alone. Ubiquitination reactions were performed in the presence or absence of E1, E2, E3(m) or FLAG-ubiquitin as indicated.

Figure 19:
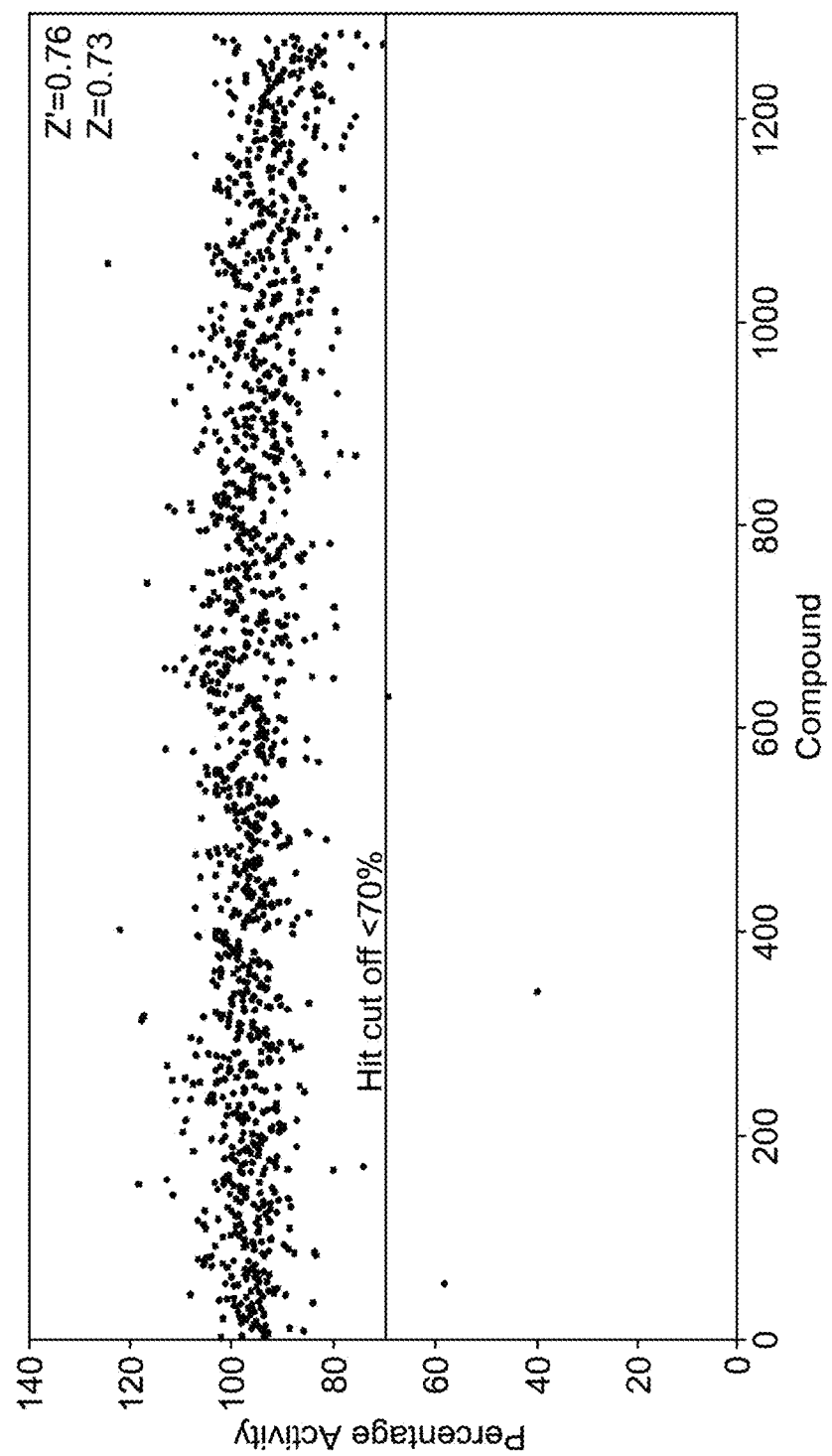

FIG. 19. Graphical representation of the data obtained from a pilot screen of 1,280 small molecules from the LOPAC[1280]™ library in the high throughput ELISA. Hits were identified from wells showing activity of 70% or less of the mean of the positive controls.

DETAILED DESCRIPTION OF THE INVENTION

Advantages

Ubiqutin ligases are tractable drug targets that offer great potential for drug design. Firstly, they are enzymes and therefore represent easy molecules to target for design of small molecule inhibitors. In addition, small molecules that target enzymes which, in turn, regulate degradation can be used to increase the activity of a target where otherwise design of molecules to act directly on that target may not be possible.

DEFINITIONS

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-

128, ed. E. J. Murray, The Humana Press Inc., Clifton, N.J.). These documents are incorporated herein by reference.

Itch

Ubiquitin is a protein that can become covalently attached to lysine residues on target proteins. This reaction requires the sequential action of 3 enzymes, the E1, E2 and E3 enzymes. After modification with a number of ubiquitin moieties linked through Lys 48 of ubiquitin, the ubiquitinated protein is targeted for ATP-dependent degradation by the 26S proteasome. In this process, the E3 ubiquitin ligases catalyze the final transfer of ubiquitin to a specific substrate, thus governing the specificity of substrate recognition (Hicke, 2001; Kloetzel, 2001; Weissman, 2001). Therefore, therapeutic targetting of particular E3 ligases will produce selective alterations in the degradation rates of small groups of proteins, rather than inhibiting ubiquitination and degradation of all proteins in the proteasome. E3 enzymes contain two separate activities: a ubiquitin ligase activity to conjugate ubiquitin to substrates and form polyubiquitin chains via isopeptide bonds, and a targetting or binding activity to physically bring the ligase and substrate together.

In addition to its role in ubiquitination and degradation, ubiquitin can also confer a subcellular address label on proteins, resulting in changes to their intracellular localisation, and therefore, function.

Itch is an example of an E3-ubiquitin ligase that belongs to the Nedd4-like E3 family, and is characterized by a modular organization that includes: an N-terminal protein kinase C-related C2 domain; multiple WW domains; and a C-terminal HECT (homologous to the E6-associated protein carboxyl terminus) Ubiquitin (Ub)-protein ligase domain (Harvey, 1999) (FIG. 1A). The Itch mouse homologue gene is absent in the non-agouti-lethal 18H (Itchy) mice which display profound immune defects (Fang, 2002; Perry, 1998).

Itch ubiquitinates Jun-B targetting it for degradation (Fang et al Nat. Immunol. 2002). Itch has been shown to be phosphorylated by JNK-1 and JNK-2 in response to T-cell stimulation (Gao et al Science 2004) and phosphorylation of Itch results in increased catalytic activity (Gao et al Science 2004). In addition, Itch ubiquitinates cJun and Jun-B targetting them for degradation and modulating cytokine production (Gao et al Science 2004). Itch also regulates TGF-Beta response by promoting SMAD phosphorylation (Bai et al Mol. Cell. 2004) and regulates Notch (Qui et al J. Biol. Chem. 2000). Itch also undergoes self-ubiquitination (Gao et al Science 2004).

Human Itch is described by Perry W L, Hustad C M, Swing D A, O'Sullivan T N, Jenkins N A, Copeland N G. Nat. Genet. 1998 18:143-6 and the sequences deposited under GenBank Accession numbers NM_031483 (nucleotide) (gi27477108) and NP_113671 (protein) (gi:27477109).

Reference to Itch herein includes Itch and its variants, homologues, fragments or derivatives.

p63 and p73

Reference to p63 and p73, as used herein, includes p63, p73 and any of their variants, homologues, fragments or derivatives including truncated and alternatively spliced forms or isoforms as described herein. In particular, reference to p63 and p73 includes reference to TAp73, ΔNp73 and ΔNp63. These isoforms are described, for example, by Melino et al., Trends in Biochemical Sciences, Vol. 28, No. 12, December 2003, Melino et al. Nature Reviews, Vol. 2, p. 1-11, August 2002. The mRNA sequence encoding p63 protein can be found in GenBank NM_003722, while the mRNA encoding p73 protein can be found in GenBank NM_005427.

Variants, Homologues, Fragments or Derivatives

The term "variant" is used to mean a naturally occurring polypeptide or nucleotide sequence which differs from the naturally occurring sequence.

The term "fragment" indicates that a polypeptide or nucleotide sequence comprises a fraction of a sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, most preferably at least 90% of a sequence described herein.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 70, 75, 80, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 70, 75, 80, 85 or 90% identical, preferably at least 95 or 98% identical to the subject sequence. Typically, the homologues will comprise the same sequences that encode for the active sites etc. as the subject sequence. Although homology can also be considered in terms of similarity, in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system.

High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid$^\#$, 7-amino heptanoic acid*, L-methionine sulfone$^{\#*}$, L-norleucine*, L-norvaline*, p-nitro-L-phenylalanine*, L-hydroxyproline$^\#$, L-thioproline*, methyl derivatives of phenylalanine (Phe)—such as 4-methyl-Phe*, pentamethyl-Phe*, L-Phe (4-amino)$^\#$, L-Tyr (methyl)*, L-Phe (4-isopropyl)*, L-Tic (1,2,3,4-tetrahydroisoquinoline-3-carboxyl acid)*, L-diaminopropionic acid$^\#$ and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

Alleles of sequences—such as Itch, p63 or p73—are also included. As used herein, an "allele" or "allelic sequence" is an alternative form of the receptor. Alleles result from a mutation, ie., a change in the nucleic acid sequence, and generally produce altered mRNAs or polypeptides whose structure or function may or may not be altered. Preferably, function is not altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The term "allele" also includes genetic polymorphisms—such as SNPs (single nucleotide polymorphisms).

The terms "variant", "homologue", "derivative" or "fragment" include any substitution of, variation of, modification of, replacement of, deletion of or addition of one (or more) nucleic acids from or to the sequence providing the resultant nucleotide sequence is capable of coding for a protein having the desired activity—such as Itch ubiquitin ligase activity, preferably being at least as biologically active as the protein encoded by any one of the sequences shown herein.

Apoptosis

"Apoptosis" or cell death is a controlled intracellular process characterised by the condensation and subsequent fragmentation of the cell nucleus during which the plasma membrane remains intact. A cascade of enzymes including caspases that cleave at aspartic acid residues is activated in the process.

By "modulating apoptosis" is meant that for a given cell, under certain environmental conditions, its normal tendency to undergo apoptosis is changed compared to an untreated cell. A decreased tendency to apoptose may also be a measurable increase in cell survival and may be the result of an inhibition of apoptosis by inhibiting one or more components of the apoptotic pathway. An increase in the tendency to undergo apoptosis is measurable by increased cell death, for instance as described below.

Methods for inducing apoptosis are well known in the art and include, without limitation, exposure to chemotherapy or radiotherapy agents and withdrawal of obligate survival factors (e.g. GM-CSF, NGF) if applicable. Differences between treated and untreated cells indicates effects attributable to the test agent.

Methods for measuring apoptosis are familiar to those skilled in the art and are described herein.

Functional Activity

The "functional activity" of a protein in the context of the present invention describes the function the protein performs in its native environment. Altering or modulating the functional activity of a protein includes within its scope increasing, decreasing or otherwise altering the native activity of the protein itself. In addition, it also includes within its scope increasing or decreasing the level of expression and/or altering the intracellular distribution of the nucleic acid encoding the protein, and/or altering the intracellular distribution of the protein itself.

Expression

The term "expression" refers to the transcription of a genes DNA template to produce the corresponding mRNA and translation of this mRNA to produce the corresponding gene product (i.e., a peptide, polypeptide, or protein). The term "activates gene expression" refers to inducing or increasing the transcription of a gene in response to a treatment where such induction or increase is compared to the amount of gene expression in the absence of said treatment. Similarly, the terms "decreases gene expression" or "down-regulates gene expression" refers to inhibiting or blocking the transcription of a gene in response to a treatment and where such decrease or down-regulation is compared to the amount of gene expression in the absence of said treatment.

Modulating

The term "modulating" may refer to preventing, suppressing, alleviating, restoring, increasing, elevating or otherwise affecting the activity and/or expression of Itch. In particular, the term "modulating" refers to modulating the ubiquitin ligase activity of Itch.

By modulating p63 or p73 stability is meant effecting a change in steady state protein level of the proteins in the presence of a candidate compound as compared to those levels in the absence of a candidate compound. Levels of proteins can be assessed, for example, by Western blot analysis.

The activity and/or expression of Itch may be modulated by affecting the degree of binding or interaction between Itch and its substrates such as p63 and p73. By way of example, the degree of binding or interaction may be increased using an agent that binds to or interacts with amino acid residues of Itch that increase the activity and/or expression of Itch. By way of further example, the degree of binding or interaction may be decreased using an agent that binds to or interacts with amino acid residues of Itch that decrease the activity and/or expression of said receptor.

Agents that are able to modulate the activity and/or expression of Itch may be agonists or antagonists.

Agonists and Antagonists

Agents capable of increasing or elevating the activity and/or expression of Itch are referred to as agonists.

Agents capable of reducing, inhibiting or blocking the activity and/or expression of Itch are referred to as antagonists.

Advantageously, the assay methods of the present invention may be used to identify agents—such as agonists or antagonists—that modulate the activity and/or expression of Itch.

The term "agonist", as used in the art, is generally taken to refer to a compound or agent which binds to a protein and increases its activity. The term as used here, however, is intended to refer broadly to any agent, which increases the activity and/or expression of Itch, not necessarily by binding to it. Accordingly, it includes agents, which increase the expression of one or more proteins, or the biosynthesis of a molecule, or the expression of modulators of the activity of Itch. The specific activity which is increased may be any activity which is characteristic of Itch.

The agonist may bind to and compete for one or more sites on Itch. However, the agonist need not necessarily bind directly to the binding or active site of Itch, and may bind for example to an adjacent site, another protein (for example, a protein which is complexed with Itch) or other entity on or in the cell, so long as its binding increases the expression and/or activity of Itch.

Increasing the activity of a ubiquitin ligase may also be achieved by increasing the level of expression of Itch in the cell.

In some embodiments, the present invention relies on blocking or decreasing the activity of Itch. Agents which are capable of such activity are referred to as "Itch antagonists".

The term "antagonist" is intended to refer broadly to any agent which inhibits, blocks or decreases the activity or activation of Itch, not necessarily by binding to it.

Accordingly, it includes agents which affect the expression of Itch, or the expression of modulators of the activity of Itch. The activity which is inhibited may be any activity which is characteristic of Itch—such as ubiquitin ligase activity. Preferably, the activity, which is inhibited, blocked or decreased, is the ubiquitination of p73 or p63. More preferably, the activity, which is inhibited, blocked or decreased is the ubiquitination and hence proteasomal-dependent degradation of its substrates including p73 and p63. Most preferably, the inhibition, blocking or decreasing of Itch ubiquitin ligase activity, mediates induction of apoptosis in cells through increased levels of Itch substrates such as p73 and p63.

The antagonist may bind to and compete for one or more binding or active sites on Itch. Such binding may block, inhibit or decrease interactions with Itch substrates. Such binding may block, inhibit or decrease the interaction between Itch and p73 or p63. However, the antagonist need not necessarily bind directly to Itch, and may bind for example to an adjacent site, another protein (for example, a protein which is complexed with Itch) or any other entity on or in the cell, so long as its binding blocks, inhibits or decreases the activity of Itch.

An antagonist of Itch may include a ligand of Itch, or a fragment of this, which is capable of binding to Itch. In addition, whole or fragments of a ligand generated natively or by peptide synthesis may be used to compete with the ligand for binding sites on Itch. Alternatively, or in addition, an immunoglobulin (for example, a monoclonal or polyclonal antibody) capable of binding to Itch may be used. The antagonist may also include a peptide or other small molecule, which is capable of interfering with the binding interaction. The antagonist may also include an aptamer. Other examples of antagonists are set forth in greater detail below, and will also be apparent to the skilled person.

Blocking, inhibiting or decreasing the activity of Itch may also be achieved by reducing the level of expression of Itch in the cell. For example, the cell may be treated with antisense compounds, siRNA or ribozymes for example, having sequences specific to Itch.

In a highly preferred embodiment, the Itch antagonist is a selective Itch antagonist. As used herein, the term "selective Itch antagonist" means an antagonist having at least 100-fold selectivity over related ubiquitin ligases including, for example, mdm2, NEDD4 and cCb1.

Advantageously, the Itch antagonist can be used in the treatment of cancer or epidermal abnormalities. Other disorders include immune system regulatory disorders.

By way of example only, Itch antagonists may be identified using methods for detecting ubiquitin ligase activity such as those described in WO 01/75145, for example. Briefly, a candidate antagonist, Itch, preferably, recombinant Itch (or a variant, homologue, fragment or derivative thereof) and an Itch substrate, suitably selected from p73 and p63, are configured to permit detection of Itch antagonists by measuring incorporation of ubiquitin onto the substrates in the presence or absence of the candidate antagonist.

Suitably incorporation of ubiquitin is monitored using a system that produces a signal which varies with the extent of ubiquitination, such as the incorporation of $^{35}S$ methionine in the presence of ATP and ubiquitin, as described herein. Other monitoring methods include a fluorescence resonance energy transfer system (FRET) as described, for example, in WO 01/75145.

Another method of screening a library of compounds or agents for Itch antagonists utilises eukaryotic or prokaryotic host cells, which are stably transformed with recombinant DNA molecules expressing a library of compounds. Such cells, either in viable or fixed form, can be used for standard binding-partner assays. See also Parce et al. (1989) Science 246:243-247; and Owicki et al. (1990) Proc. Nat'l Acad. Sci. USA 87; 4007-4011, which describe sensitive methods to detect cellular responses. Competitive assays are particularly useful, where the cells expressing the library of compounds are contacted or incubated with a labelled antibody known to bind to Itch—such as $^{125}I$-antibody, and a test sample such as a candidate compound whose binding affinity to the binding composition is being measured. The bound and free-labelled binding partners for the polypeptide are then separated to assess the degree of binding. The amount of test sample bound is inversely proportional to the amount of labelled antibody binding to the polypeptide.

Another technique for screening involves an approach, which provides high throughput screening for new compounds having suitable binding affinity, e.g., to an Itch polypeptide, and is described in detail in WO 84/03564. First, large numbers of different small peptide test compounds are synthesized on a solid substrate, e.g., plastic pins or some other appropriate surface; see Fodor et al. (1991). Then all the pins are reacted with solubilized polypeptide and washed. The next step involves detecting bound polypeptide. Compounds which interact specifically with the polypeptide will thus be identified.

Preferably, the methods used to identify Itch antagonists include the additional step of determining if the Itch antagonist is a selective Itch antagonist. This optional step comprises measuring the activity of the Itch antagonist for activity against another ubiquitin ligase. A Itch antagonist with a 100-fold selectivity over another ubiquitin ligase is indicative that the Itch antagonist is a selective Itch antagonist.

Specific examples of potential Itch agonists and antagonists include antibodies or, in some cases, nucleotides and their analogues, including purines and purine analogues, oligonucleotides or proteins which are closely related to the substrates or binding partners of Itch, eg., a fragment of the substrate or binding partner.

Subject

The term "subject" includes all animals including humans. Examples of subjects include humans, cows, dogs, cats, goats, sheep, horses, and pigs. The mammals to be treated according to this invention are subjects who have developed proliferative disorders including cancer, immune regulatory disorders or epidermal abnormalities and/or are suffering from the symptoms associated with disease, or who are at risk for developing the disease, for example having a family history of any of these disorders. Those skilled in the art are readily able to identify individual patients who are afflicted with such disorders, as well as those who are susceptible to developing the diseases.

Assays/Methods

Suitable assays for identifying compounds that interact with and/or modify Itch activity and/or interactions can be formulated.

Such suitable assays include, for example, flourimetric assays for ligase activity although other assay readout methods can be used.

One such suitable assay can be a two-step reaction in which HA-tagged p73 or p63 cDNA is cloned into a bacterial expression vector and fused in frame with GST (C-terminally). A cleavage site for a protease is present immediately downstream the cloning site to allow the removal of the GST sequence following the last purification step (see Figure A). The p63 (or p73)-GST expression vector may be grown in the BL21 strain and purified using a commercial kit. Preferably, the GST portion of the fusion p63 (or p73)-GST may be removed by incubation with the specific protease (see Figure A) in order to avoid the GST sequence interfering with the ubiquitination reaction. Purified HA-E1-coated plates may be incubated with GST-Ubc7-E2 and EGFP-Ubiquitin in the presence of ATP (see Figure A). Subsequently, supernatants from the E1/E2 reactions will be aliquoted on p63-(or p73-) GST-coated plates in the presence or absence of Itch (see Figure A). Reactions will be carried out in the presence or absence of the library. After extensive and stringent washing, plates will be analyzed by immunofluorescence suitably using an automated procedure.

Suitable negative controls may be included as follows:
- E1/E2 reactions in the absence of E2
- E1/E2 reactions in the absence of ATP.
- E1/E2 reactions in the presence of an EGFP-ubiquitin mutant that cannot be transferred to E3s.
- Reactions in the presence of GST only coated plates.

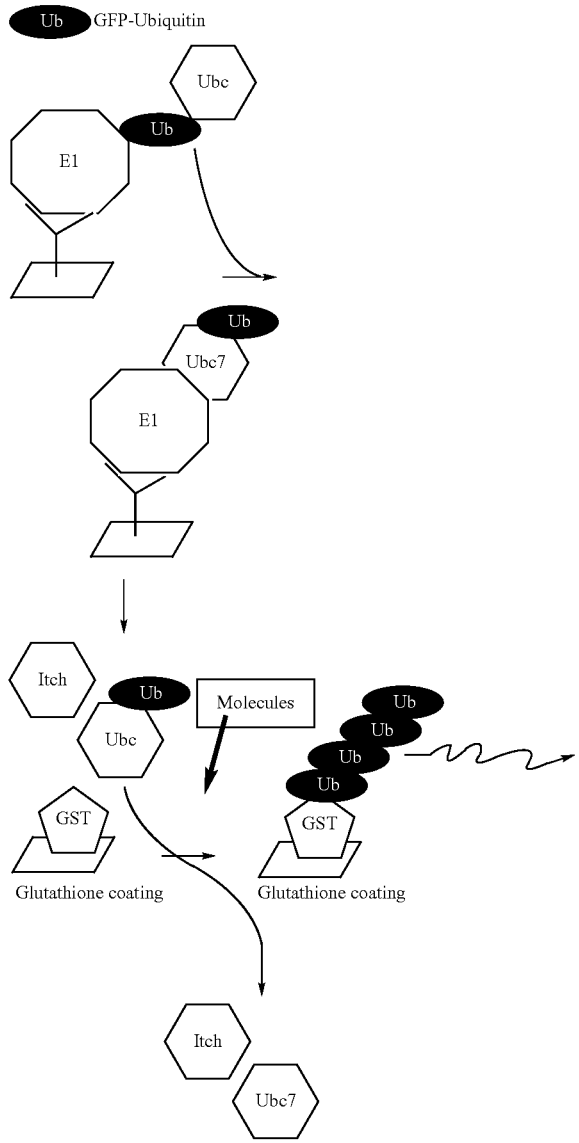

Figure A

In a further aspect, there is provided a cell-based screening method to identify agents that modulate Itch activity and/or expression.

Thus, a cell line that expresses Itch may be used to screen for agents that modulate Itch activity and/or the expression thereof. For example, screening of peptide libraries or organic libraries made by combinatorial chemistry with the cell line may be useful for identification of therapeutic agents that function by modulating Itch activity and/or expression. Synthetic compounds, natural products, and other sources of potentially biologically active materials can also be screened using the cell lines in a number of ways deemed to be routine to those of skill in the art.

The agent(s) to be tested, may be administered to the cell in several ways. For example, it may be added directly to the cell culture medium or injected into the cell. Alternatively, in the case of polypeptide agents, the cell may be transfected with a nucleic acid construct, which directs expression of the polypeptide in the cell. Preferably, the expression of the polypeptide is under the control of a inducible promoter.

Thus, in a further aspect, there is provided an assay method for identifying one or more agents that modulate the activity and/or expression of Itch, the assay method comprising the steps of: (i) providing a cell that expresses or is capable of expressing Itch or a variant, derivative or homologue thereof; (ii) contacting the cell with an agent; and (iii) measuring the levels of ubiquitination of a substrate such as p63 or p73; wherein a difference between a) levels of ubiquitination in the absence of the agent and b) levels of ubiquitination in the presence of the agent is indicative that the agent can affect Itch activity and/or expression.

By way of example only, the cell-based screening method to identify agents that modulate Itch activity and/or expression may be performed as follows. Cells—such as Hek293 cells—are plated out and grown to confluence and then washed with, for example, DMEM. DMEM is removed from the cells and the agent to be tested or DMEM alone are added (as a control). The cells are then incubated with one or more agents. The cells may additionally be transfected with expression vectors encoding the Itch substrates p73 or p63. The cells are then incubated and the levels of substrate ubiquitination determined using Western blotting, as described herein, for example.

Other Potential Assays to Screen for Inhibitors of Itch

Screens for Itch modulators may also be performed by monitoring changes in Itch self-ubiquitination. Suitable assays are described, for example, in the Examples section herein.

A high throughput screen to identify inhibitors of a ubiquitin ligase such as Itch, may be configured in a number of ways as understood by the skilled artisan. For example, polyubiquitin chain formation may be assayed using TR-FRET (Hong C A, Swearingen E, Mallari R, Gao X, Cao Z, North A, Young S W, Huang S G. 2003. Development of a high throughput time-resolved fluorescence resonance energy transfer assay for TRAF6 ubiquitin polymerization. *Assay Drug Dev Technol.* 1:175-80). In this mode, ubiquitin mixtures are optimised to consist of a proportion of two different fluorophore-labelled ubiquitins, which act as a donor and acceptor pair to give a FRET signal when brought together in a polymer. Ubiquitin may be labelled with a FRET partner directly, or indirectly using a fluorescently labelled antibody or by labelling the ubiquitin with biotin in order to combine with avidin or streptavidin bearing a FRET donor or acceptor label. In another variation, the ubiquitination target itself may be labelled with biotin and combined with a streptavidin-labelled fluorophore for use in combination with an appropriate fluorescently-labelled ubiquitin as the FRET partner (Yabuki N, Watanabe S, Kudoh T, Nihira S, Miyamato C. 1999. Application of homogeneous time-resolved fluorescence, HTRFTM, to monitor poly-ubiquitination of wild-type p53. *Comb Chem High Throughput Screen.* 2:279-87). This type of assay can be configured without the need for wash stages, however the signal to background ratio for this type of assay tends to be poorer, and unlike ELISA assays, homogeneous FRET assays are prone to interference from fluorescent library compounds. The authors also compare the FRET assay with a scintillation proximity assay (SPA) using $I^{125}$ labelled ubiquitin ($I^{125}$Ub). During the ubiquitination reaction, $I^{125}$Ub is transferred to the biotinylated p53 substrate, which in turn is detected by binding to streptavidin-coated PVT SPA beads followed by scintillation counting.

In a modification to the ELISA format, electrochemiluminescence assays may be configured to screen for inhibitors of ubiquitin ligases (Davydov I V, Woods D, Safuran Y J, Oberoi P, Fearnhead H O, Fang S, Jensen J P, Weissman A M, Kenten J H, Vousden K H. 2004. Assay for ubiquitin ligase activity: high-throughput screen for inhibitors of HDM2. *J Biomol Screen.* 9:695-703; Kenten J H, Davydov I V, Safuran Y J, Stewart D H, Oberoi P, Biebuyck H A. 2005. Assays for high-throughput screening of e2 and e3 ubiquitin ligases. *Methods Enzymol.* 399:682-701). In this format the detection reagent, for example an antibody to polyubiquitin chains, is conjugated to an electroluminescent label such as ruthenium tris-bypyridine or its derivatives. Such a label will emit light under oxidation at an electrode under suitable chemical conditions. For this type of assay electrodes are incorporated into the base of specially constructed microtiter plates and since the emission only occurs when the label is in close proximity to the electrode surface, it is possible to eliminate or minimise the number of wash steps in the assay procedure. Such assays also tend to have good sensitivity and dynamic range.

Agent

As used herein, the term "agent" may be a single entity or it may be a combination of entities.

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule. The agent may even be an antibody.

The agent may be designed or obtained from a library of compounds, which may comprise peptides, as well as other compounds, such as small organic molecules.

By way of example, the agent may be an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex.

The term "agent" is also intended to include, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, a signalling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA, siRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. Small molecules, including inorganic and organic chemicals, which bind to Itch are also included. Examples of small molecules include but are not limited to small peptides or peptide-like molecules.

Typically, the agent will be an organic compound. Typically the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the agent comprises at least one cyclic group. The cyclic group may be a polycyclic group, such as a non-fused polycyclic group. For some applications, the agent comprises at least the one of said cyclic groups linked to another hydrocarbyl group.

The agent may contain halo groups. Here, "halo" includes fluoro, chloro, bromo or iodo.

The agent may contain one or more of alkyl, alkoxy, alkenyl, alkylene and alkenylene groups—which may be unbranched—or branched-chain.

The agent may be capable of displaying other therapeutic properties.

The agent may be used in combination with one or more other pharmaceutically active agents—such as one or more other pharmaceutically active agents that can be used to treat proliferative disorders such as cancer.

If combinations of active agents are administered, then they may be administered simultaneously, separately or sequentially.

If the agent is an antibody then it may include but is not limited to, polyclonal, monoclonal, chimeric, single chain, Fab fragments and fragments produced by a Fab expression libraries. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used. Neutralizing antibodies.

Antibodies may be produced by standard techniques, such as by immunisation or by using a phage display library An Itch polypeptide or peptide may be used to develop an antibody by known techniques. Such an antibody may be capable of binding specifically to the Itch protein or a homologue, variant, fragment or derivative thereof.

If polyclonal antibodies are desired, a selected mammal (e.g., mouse, rabbit, goat, horse, etc.) may be immunised with an immunogenic composition comprising an Itch polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed if purified the substance amino acid sequence is administered to immunologically compromised individuals for the purpose of stimulating systemic defence.

Serum from the immunised animal is collected and treated according to known procedures. If serum containing polyclonal antibodies to an epitope obtainable from an Itch polypeptide contains antibodies to other antigens, the polyclonal antibodies can be purified by immunoaffinity chromatography. Techniques for producing and processing polyclonal antisera are known in the art. In order that such antibodies may be made, the invention also provides amino acid sequences of the invention or fragments thereof haptenised to another amino acid sequence for use as immunogens in animals or humans.

Monoclonal antibodies directed against epitopes obtainable from an Itch polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce the substance specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for the Itch polypeptide or peptide may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275-1281).

Techniques for the production of single chain antibodies (U.S. Pat. No. 4,946,778) can also be adapted to produce single chain antibodies to Itch polypeptides. Also, transgenic mice, or other organisms including other mammals, may be used to express humanized antibodies.

The agent may be an aptamer ie. an oligonucleotide that is capable of forming a complex with an intended target—such as Itch. Aptamers may be prepared by any known method, including synthetic, recombinant, and purification methods, and may be used alone or in combination with other aptamers specific for the same target. The oligonucleotides may be single-stranded, double-stranded, or even triple- or quadruple-stranded structures. In general, a minimum of approximately 3 nucleotides, preferably at least 5 nucleotides, are necessary to effect specific binding. Oligonucleotides of sequences shorter than 10 bases may be feasible if the appropriate interaction can be obtained in the context of the environment in which the target is placed, although aptamers of about 10, 15, 20, 25, 30, 35, 40, 45, 50, 55, 60, 65, 70, 75, 80, 85, 90, 95 or 100 nucleotides or more in length are contemplated. Methods of constructing and determining the binding characteristics of aptamers are well known in the art. For example, such techniques are described in U.S. Pat. Nos. 5,582,981, 5,595,877 and 5,637,459. General teachings on aptamers can be found in Blackwell et al., Science (1990) 250:1104-1110; Blackwell et al., Science (1990) 250:1149-1152; Tuerk & Gold, Science (1990) 249:505-510; and Joyce, Gene (1989) 82:83-87.

Cell

The cell (eg. tissue) that is used in accordance with the present invention is a cell that expresses Itch. The cell may be any prokaryotic or eukaryotic cell. Cells that are particularly useful in the context of the present invention include mammalian cells and, in particular, human cells of a variety of cell types.

Preferably, the cell is selected from the group consisting of human embryonic kidney cells such as Hek293, HeLa, MEF, human lung carcinoma cells such as H1299 and human osteosarcoma cells such as Saos-2.

A person skilled in the art will appreciate that other cells may also be used in accordance with the present invention—such as host cells expressing Itch and/or its substrates including p63 and p73. These cells may be particularly useful when using assays or screens to identify antagonists of Itch. Host cells include any cell that could comprise an Itch nucleotide sequence and/or a p63 or p73 nucleotide sequence (or a variant, homologue, fragment or derivative thereof) coding for recombinant Itch or its substrates, wherein a promoter can allow expression of the nucleotide sequence when present in the host cell. The host cells will be chosen to be compatible with the vector carrying the nucleotide sequences and may for example be prokaryotic or eukaryotic.

Depending on the nature of the polynucleotide encoding the polypeptide, and/or the desirability for further processing of the expressed protein, prokaryotic hosts or eukaryotic hosts—such as yeasts or other fungi—may be used.

The use of suitable host cells—such as mammalian, yeast, fungal and plant host cells—may provide for post-translational modifications (e.g. myristoylation, glycosylation, proteolytic processing, lipidation and tyrosine, serine or threonine phosphorylation) as may be needed to confer optimal biological activity on the recombinant expression products.

siRNA

A nucleic acid may be delivered into a cell that modulates the activity and/or expression of Itch, for example, at the level of transcription, transcript stability, translation or post-translational stability. For example, the nucleic acid may be an antisense sequence or an siRNA.

The inhibition of gene expression using antisense technology is well known. For example, antisense constructs are described in detail in U.S. Pat. No. 6,100,090 (Monia et al), and Neckers et al., 1992, *Crit. Rev Oncog* 3(1-2):175-231.

The siRNA may comprise partially purified RNA, substantially pure RNA, synthetic RNA, or recombinantly produced RNA, as well as altered RNA that differs from naturally-occurring RNA by the addition, deletion, substitution and/or modification of one or more nucleotides.

Such alterations can include the addition of non-nucleotide material—such as modified nucleotides—to, for example, the end(s) of the siRNA or to one or more internal nucleotides of the siRNA, including modifications that make the siRNA resistant or even more resistant to nuclease digestion.

Typically, the siRNA will be in the form of isolated siRNA comprising short double-stranded RNA from about 17 nucleotides to about 29 nucleotides in length—such as approximately 19-25 contiguous nucleotides in length—that are targeted to a target mRNA. The siRNA comprise a sense RNA strand and a complementary antisense RNA strand annealed together by standard Watson-Crick base-pairing interactions. The sense strand comprises a nucleic acid sequence which is identical to a target sequence contained within the target mRNA.

A target sequence on the target mRNA encoding Itch may be selected from a given sequence—such as a cDNA sequence—corresponding to the target mRNA, using various methods in the art. For example, the rational design of siRNAs is described in Nat Biotechnol. (2004) 22(3):326-30. Suitable siRNA molecules are described herein.

Although siRNA silencing is highly effective by selecting a single target in the mRNA, it may be desirable to design and employ two independent siRNA duplexes to control the specificity of the silencing effect.

siRNA may be obtained using a number of techniques known to those of skill in the art. For example, the siRNA may be chemically synthesized using appropriately protected ribonucleoside phosphoramidites and a conventional DNA/RNA synthesiser. The siRNA may be synthesized as two separate, complementary RNA molecules, or as a single RNA molecule with two complementary regions.

siRNA may be recombinantly produced using methods known in the art. For example, siRNA may be expressed from recombinant circular or linear DNA plasmids using any suitable promoter. The recombinant plasmids of the invention can also comprise inducible or regulatable promoters for expression of the siRNA in a particular tissue or in a particular intracellular environment.

Treatment

As used herein, the term "treatment" includes curing or treating proliferative disorders including cancer, causing the symptoms of such disorders to diminish, and ablating or otherwise alleviating the disease.

Pharmaceuticals

The agents—such as the Itch antagonists—that modulate (eg. decrease) the activity and/or expression of Itch will typically be formulated into a pharmaceutical composition. In this regard, and in particular for human therapy, even though the agents described herein can be administered alone, they will generally be administered in admixture with a pharmaceutical carrier, excipient or diluent selected with regard to the intended route of administration and standard pharmaceutical practice.

By way of example, in the pharmaceutical compositions, the agents may be admixed with any suitable binder(s), lubricant(s), suspending agent(s), coating agent(s), or solubilising agent(s).

Tablets or capsules of the agents may be administered singly or two or more at a time, as appropriate. It is also possible to administer the agents in sustained release formulations.

Thus, the present invention also provides a method of treating proliferative disorders in a subject comprising administering to said subject an effective amount of an Itch antagonist.

Typically, the pharmaceutical compositions—which may be for human or animal usage—will comprise any one or more of a pharmaceutically acceptable diluent, carrier, excipient or adjuvant. The choice of pharmaceutical carrier, excipient or diluent can be selected with regard to the intended route of administration and standard pharmaceutical practice. As indicated above, the pharmaceutical compositions may comprise as—or in addition to—the carrier, excipient or diluent any suitable binder(s), lubricant(s), suspending agent(s), coating agent(s), solubilising agent(s).

For some embodiments of the present invention, the pharmaceutical compositions will comprise an agent that has been screened by the assay method(s) described herein.

Such molecules may provide the basis for treatment of proliferative disorders such as cancer. For example, such molecules may be used to increase apoptosis.

Expression vectors derived from retroviruses, adenovirus, herpes or vaccinia viruses, or from various bacterial plasmids, may be used for delivery of recombinant sense or antisense molecules to the targeted cell population. Methods, which are well known to those skilled in the art, can be used to construct recombinant vectors containing the receptor. Alternatively, the recombinant receptor can be delivered to target cells in liposomes.

The pharmaceutical composition could be for veterinary (i.e. animal) usage or for human usage.

The pharmaceutical compositions obtained may be useful for preventing and/or treating proliferative disorders such as cancer.

It will be appreciated by those skilled in the art that the agent may be derived from a prodrug. Examples of prodrugs include certain protected group(s) which may not possess pharmacological activity as such, but may, in certain instances, be administered (such as orally or parenterally) and thereafter metabolised in the body to form an agent that is pharmacologically active.

It will be further appreciated that certain moieties known as "pro-moieties", for example as described in "Design of Prodrugs" by H. Bundgaard, Elsevier, 1985, may be placed on appropriate functionalitis of the agents. Such prodrugs are also included within the scope of the invention.

The agent may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

The agent may be prepared by chemical synthesis techniques.

It will be apparent to those skilled in the art that sensitive functional groups may need to be protected and deprotected during synthesis of a compound of the invention. This may be achieved by conventional techniques, for example, as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be racemised, for example, if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The agent or variants, homologues, derivatives, fragments or mimetics thereof may be produced using chemical methods to synthesise the agent in whole or in part. For example, if the agent comprises a peptide, then the peptide can be synthesised by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure; Creighton, supra).

Synthesis of peptide agents (or variants, homologues, derivatives, fragments or mimetics thereof) can be performed using various solid-phase techniques (Roberge J Y et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the agent, may be altered during direct synthesis and/or combined using chemical methods with a sequence from other subunits, or any part thereof, to produce a variant agent.

The agent may be a modified agent—such as, but not limited to, a chemically modified agent.

The chemical modification of an agent may either enhance or reduce hydrogen bonding interaction, charge interaction, hydrophobic interaction, Van Der Waals interaction or dipole interaction.

In one aspect, the agent may act as a model (for example, a template) for the development of other compounds.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components may be administered alone but will generally be administered as a pharmaceutical composition—e.g. when the components are in admixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Conveniently, administration may be by inhalation. Commercially available nebulisers for liquid formulations, including jet nebulisers and ultrasonic nebulisers are useful for such administration. Liquid formulations can be directly nebulised and lyophilised powder can be nebulised after reconstitution.

For administration by inhalation, the agents are conveniently delivered in the form of an aerosol spray presentation from pressurised packs or nebulisers. The agents may also be delivered as powders which may be formulated and the powder composition may be inhaled with the aid of an insufflation powder inhaler device.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Formulation

The component(s) may be formulated into a pharmaceutical composition, such as by mixing with one or more of a suitable carrier, diluent or excipient, by using techniques that are known in the art.

Kits

The materials for use in the present invention are ideally suited for the preparation of kits.

Such a kit may comprise containers, each with one or more of the various reagents (optionally in concentrated form)

utilised in the methods, including, a cell that expresses or is capable of expressing Itch; and one of its substrates including p63 or p73.

The kit optionally further comprises one or more controls—such as a cell that cannot express Itch.

A set of instructions will also typically be included.

Suitably, the kit is a diagnostic kit for measuring Itch expression in tumours. Use of such a kit, for example, will allow treatment diagnosis as Itch expression correlates with therapy insensitivity or inversely correlates with survival.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The invention will now be further described by way of Examples, which are meant to serve to assist one of ordinary skill in the art in carrying out the invention and are not intended in any way to limit the scope of the invention.

EXAMPLES

Example 1

The Ubiquitin-Protein Ligase Itch Regulates p73 Stability

Materials and Methods

Plasmids

Myc-Itch and Myc-Itch MUT plasmids (C830A) were provided by Dr. T. Pawson (Winberg, 2000). Itch GST fusion proteins, were generated by subcloning PCR fragments into the BamHI and SalI sites of pGEX-6P1 (Amersham Pharmacia Biotech). The following fragments were cloned: GST-Itch, from Thr 277 to Glu 903 (lacking the N-terminal C2 domain) and GST-WW, from Pro 317 to Pro 520 (spanning only the four WW domains). HA-p73 α, and HA-p73 α were described previously (De Laurenzi, 1998). GST-p73 fusion protein encompassing only the PY motif (GST-PY, from Met 452 to Ala 489) was obtained by subcloning into BainHI and NotI sites of the pGEX-6P1. The poly-HA-ubiquitin construct (HA-Ub) was kindly provided by Dr. D. Bohmann (Treier, 1994). pET23a-Ubch7 (E2) bacterial expression vectors directing the synthesis of the E2 enzyme (Ubch7) and the E1 ubiquitin-activating enzyme Uba1 were a gift of Dr. P. M. Howley (Kumar, 1997). The reporter plasmid containing the luciferase cDNA under control of the Bax and p21 promoter were provided by Dr. Levrero (Vossio, 2002); that under the control of the MDM2 promoter was provided by Dr. Blandino (Strano, 2001). Nedd4-myc construct was a gift from Dr. D. Rotin. All p73 mutants were generated by site directed mutagenesis using the Quickchange kit (Stratagene) according to the manufacturer's instructions.

Cell Culture and Transfection

Human embryonal kidney cells (Hek293), HeLa cells and MEFs were grown in Dulbecco's modified Eagle medium (DMEM) (GibcoBRL); the human lung carcinoma cells H1299 and the human osteosarcoma cells Saos-2 were cultured in RPMI (GibcoBRL). MEF Itch−/− cells were prepared from Itch−/− mice (Y—C-Liu) or they were generous gift from Neil Copeland, Lynda Matesic, Nancy Jenkins. All media were supplemented with 10% (v/v) fetal bovine serum (FBS) (GibcoBRL). Saos-2-TAp73 α, were a kind gift of K. Vousden (Nakano, 2000). Saos-2-ΔNp73 α, were generated as described before (Maisse et al., 2004). For the TET-On cell lines media was supplemented with 10% (v/v) tetracycline free FBS (Clonetech). Genes were induced by adding 0.5 μg/ml doxycycline. All cell lines were grown at 37° C. in a humidified atmosphere of 5% (v/v) $CO_2$ in air. Transient transfection was performed with lipofectamine 2000 reagent according to the manufacturer's instructions. Apoptosis was analysed by flow cytometric evaluation of DNA fragmentation.

Western Blot and Antibodies

Proteins were separated on SDS-PAGE and blotted onto nitrocellulose membranes. Filters were blocked with TBST 5% non-fat dry milk and incubated with primary antibodies for 2 hrs at room temperature (RT). Filters were incubated for 1 hour at RT using the appropriate horseradish peroxidase-conjugated secondary antibody (rabbit and mouse BioRad; goat Santa Cruz). Detection was performed with the enhanced chemiluminescence Supersignal West Pico (Pierce). Anti-p73 is a monoclonal antibody (ER15) (Neomarkers). Endogenous Itch was detected with a mouse monoclonal antibody (BD Bioscience), Actin (sc-1615) polyclonal goat antibody (Santa Cruz), Lamin B (sc-6217) goat polyclonal antibody (Santa Cruz), Hsp70 (sc-1060) polyclonal goat antibody (Santa Cruz), β-Tubulin (sc-9104) polyclonal rabbit antibody (Santa Cruz), p21 (sc-756) polyclonal rabbit antibody (Santa Cruz), p53 DO-1 and Pab1801 monoclonal mouse antibodies (Santa Cruz). c-Myc-tagged constructs were detected or immuno-precipitated with the sc-40 monoclonal mouse antibody (Santa Cruz), HA-tagged with the sc-805 polyclonal rabbit antibody (Santa Cruz), and the Flag-tagged constructs with the M2 monoclonal mouse antibody (Sigma).

Affinity Selection

An aliquot of a T7 phage display library of human brain cDNA (Novagen) was incubated overnight at 4° C., with 50 μg of GST-PY p73α fusion protein immobilized on glutathionesepharose beads (Amersham Biosciences), in the presence of 1% bovine serum albumin. Unbound phage were removed by washing five times with 1 ml of 0.1% Tween 20 in PBS, and then once in 1 ml PBS and resuspended in 50 μl of PBS. The bound phages were recovered by incubating at 37° C. with 2 ml of *E. Coli* BLT5615 (Novagen) induced with 1 mM IPTG for 30 min before phage addition. After cell lysis, the phage lysate was clarified by centrifugation, and used in a new selection round. After three selection cycles the resulting phages were analyzed by a plaque assay (Zucconi, 2001), using soluble purified GST-PY at a concentration of 5 μg/ml. Positive plaques were isolated from plates. 1 μl of the suspension was amplified by PCR using primers to the regions flanking the insert, and fragments were sequenced. To estimate the enrichment of Itch, 1 μl of clarified phage lysate corresponding to each of the different selection rounds, was amplified by PCR (20 amplification cycles).

GST-Fusion Proteins and Pull-Down Assays

GST fusion proteins were expressed in *E. Coli* BL21 (DE3) and purified on glutathionesepharose beads (Amersham Biosciences) following standard procedures. For the pull-down assay, Hek293 cells transfected with HA-TAp73α or empty vector, were lysed in 50 mM Tris HCl, pH 8, 150 mM NaCl, 1 mM MgCl$_2$, 1 mM EGTA, 10% glycerol, 100 mM NaF and 1% Triton X-100 containing protease cocktails (Sigma) and centrifuged to precipitate cellular debris. 1.5 mg of total cellular proteins were first precleared with glutathione-sepharose beads and then incubated for 2 hrs. at 4° C. with immobilized GST fusion proteins (25 µg). Unbound proteins were removed by washing four times with 0.1% Tween20 in PBS, and the precipitates were resolved by SDS-PAGE. The immunoblots were probed with the indicated antibodies.

Immunoprecipitation

Following a previously published procedure (Gottifredi, 1999) Hek293 cells were transiently transfected with 8 µg of total DNA of the indicated mammalian expression plasmids and harvested 48 hours after transfection. Cells were then lysed as described above. Following preclearing for 1 h at 4° C., we performed immunoprecipitation by incubating 1.5 mg of whole-cell extracts with the indicated antibodies, rocking at 4° C. for 1 hour. The immunocomplexes were collected by incubating with protein G Agarose (KPL), washed with Net-gel buffer (50 mM Tris pH 7.5, 150 mM NaCl, 1 mM EDTA, 0.25% gelatin, 0.1% NP40). The beads were then resuspended in 5× Laemmli buffer, and subjected to western blot with the indicated primary antibodies.

Ubiquitination Assays

In vitro assays were performed as described previously (Hamilton, 2001), using in vitro translated radiolabeled p73 and p53 proteins. In vitro transcription/translation of proteins was performed using the rabbit reticulocyte lysate system TNT kit (Promega), in the presence of [$^{35}$S]Met (Amersham Biosciences) according to the manufacturer's protocol. Ubiquitination reactions mixture contained: 2 µl of *E. Coli* BL21 bacterial extracts over-expressing wheat E1 and 2 µl of a human E2 (UbcH7), 5 µg of purified E3 enzyme (either GST-Itch or GSTItch MUT), 25 mM Tris-HCl (pH 8.0), 100 mM NaCl, 1 mM dithiothreitol, 2.5 mM ATP, 4 nM MgCl$_2$, 10 µg of bovine ubiquitin. After incubation for 90 min at 37° C., the reactions were terminated by adding 5× Laemmli buffer, resolved by SDS-PAGE followed by autoradiography.

For in vivo experiments Hek293 cells were transiently transfected with mammalian expression plasmids for HA-tagged ubiquitin (HA-Ub), with the indicated combination of plasmids. 48 hrs after transfection, cells were harvested, the insoluble fraction was removed by a high-speed spin, and 1 mg of total cellular proteins of the clarified supernatant was subjected to immuno-precipitation using anti Flag antibodies (Sigma). Ubiquitin-conjugates were detected by Western immuno-blot analysis using an anti-HA-antibodies (Santa Cruz).

Measurement of p73 Half Life

Decay of p73 protein levels in the presence of cycloheximide. Cycloheximide (20 µg/ml) was added to Hek293 cells 24 hours after transfection with a total of 3 µg of the indicated plasmids in a 1:5 ratio p73/Itch and p53/Itch. Protein levels were determined by collecting cells at the indicated time points and performing immunoblotting as described above. The relative amount of p73 protein was evaluated by densitometry and normalized on β-Tubulin. $^{35}$S pulse chase. H1299 cells were transfected with a total of 3 µg of the indicated plasmids in a 1:2 ratio p73/Itch. 48 hours post-transfection cells were starved for 30 minutes in DMEM with dialysed serum and then labelled with 250 µCi/ml of Redivue PRO-MIX (L-[$^{35}$S] in vitro cell labelling mix) for 60 minutes. Unlabeled Met and Cys were added and cells were collected in RIPA buffer (200 mM Tris pH8, 150 mM NaCl, 0.5% Sodium Deoxycholate, 0.1% SDS, 1% NP40 and 0.2 mM EDTA) at the indicated times. Immunoprecipitations were performed with 150 µg of total protein lysate and 4 µl of anti-HA (Y-11) polyclonal antibody Santa Cruz. Immunoprecipitates were washed six times in RIPA buffer and six times in NETgel and run on a SDS-PAGE and detected by autoradiography.

Steady State Protein Levels Analysis

The concentration of TAp73α, TAp73 α and p53 was monitored by Western blotting. 48 hrs after co-transfection with HA-TAp73, HA-TAp736 and HA-p53 and either Myc-Itch or Myc-Itch MUT, Hek293 cells were treated for 40 min with or without proteasome inhibitor MG132 at a final concentration of 50 µM in DMSO. 25 µg of cell lysates were subjected to Western blotting. p73 proteins were detected by an anti-HA antibody. The same blots were re-probed with anti Myc antibody to detect Itch and with anti-Actin antibody to show equal loading.

Promoter Reporter

H1299 cells were transfected with the indicated combinations of plasmids encoding p73α (10 ng/well of 96-well plate), Myc-Itch or Myc-Itch MUT, or empty control vectors together with the indicated luciferase reporter plasmid (60 ng/well) and *Renilla* luciferase reporter (1.2 ng/well). The total amount of transfected DNA in each well was kept constant by the addition of different amounts of empty vector. The luciferase activity was quantified using a commercially available kit (Dual-Glo, Promega) according to the manufacture's instructions.

Itch siRNA

Saos-2 cells were electroporated with 20 ml of a 20 mM solution of twenty-one-nucleotide RNA (Qiagen) using a BIO-RAD electroporation apparatus. A mix of two different oligoes was used to downregulate Itch. The Itch target sequences were AAGTGCTTCTCAGAATGATGA and AACCACAACACACGAATTACA and the scrambled sequence was AATTCTCCGAACGTGTCACGT. Cells were collected after 48 hours and cell lysates were subjected to western blot for Itch detection as described above.

Results

MDM2, the E3 ubiquitin ligase that regulates the degradation of the cognate protein p53 via a proteasomal dependent pathway, binds to p73 but does not promote its degradation (Balint, 1999; Dobbelstein, 1999; Lohrum, 1999; Ongkeko, 1999; Zeng, 1999).

In order to define the degradation pathway of p73 we searched a human cDNA library displayed on bacteriophage capsids for p73 specific binding partners. In order to identify mechanisms distinct from those of p53, as a bait we used a p73 C terminal fragment since this region is not present in p53 and contains a PpxY (PY) sequence that has been characterized as a binding motif for a class of WW domains (FIG. 1A) (Sudol, 1996).

Identification of Itch as a Novel p73 Interacting Partner

Figure 1B:
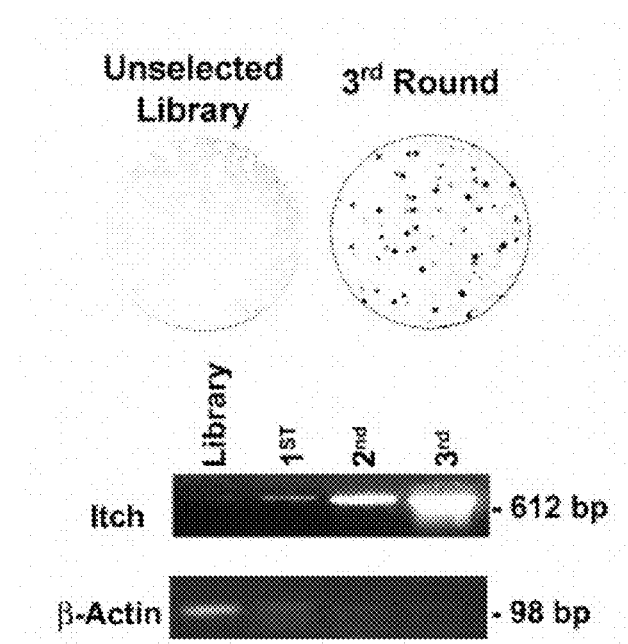

To identify new p73 binding proteins, not shared by p53, we fused a fragment of TAp73α (Met 452-Ala 489) to GST protein (FIG. 1A) and used it as bait in "phage display" screening (Castagnoli, 2001; Cesareni, 1999). This fragment contains a region that is not homologous to p53 and contains a protein-protein binding motif, known as a PY motif (Strano, 2001) (FIG. 1A) characterized by the consensus sequence PPxY. This motif binds to a 40 amino-acid long structural domain known as WW domain, organized to form a threestranded, antiparallel Psheet, containing two tryptophan (W) residues, spaced 20-22 amino acids apart (Sudol, 1996). After three rounds of affinity-selection, performed on a human brain cDNA library displayed by a T7 phage vector, we analyzed the resulting phage population by a plaque assay. The affinity selected phage pool contained a high percentage (25%) of positive clones that bound the bait (FIG. 1B). By comparing the frequency of positive plaques before and after selection, we estimated an enrichment of at least 60 fold (FIG. 1B). Several clones contained overlapping protein fragments (all containing the WW domains) encoded by the Itch gene (FIG. 1A). The enrichment of clones displaying Itch WW domains was further confirmed by performing PCR reactions with specific oligonucleotides flanking the WW domains (from Pro 317 to Pro 520) (FIG. 1B). In contrast, clones containing the β-Actin gene were rapidly lost during the selection process (FIG. 1B).

p73 but not p53 Associates with Itch

Figure 1C:
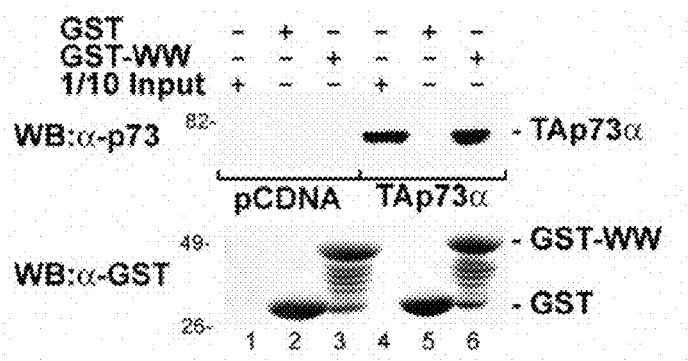
Figure 1D:
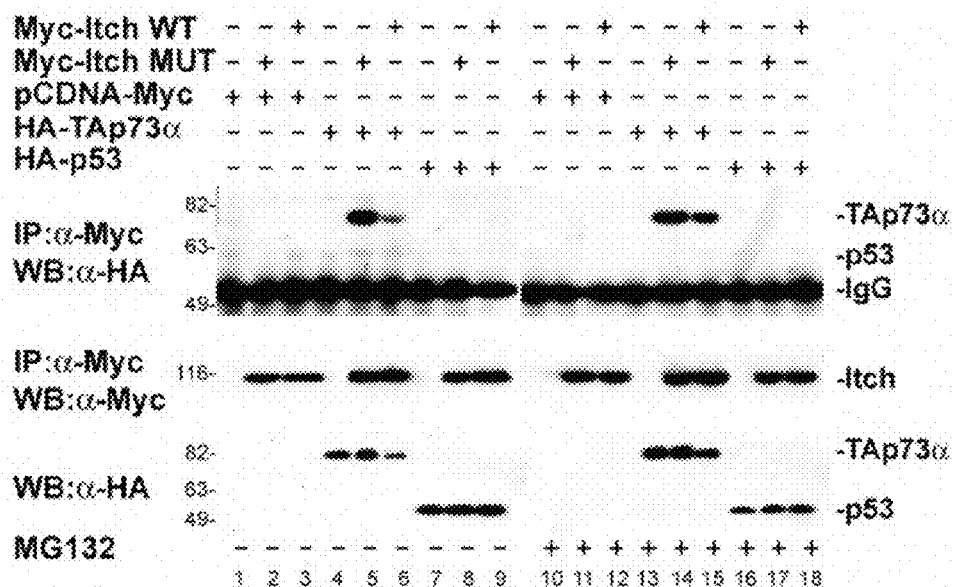
Figure 1E:
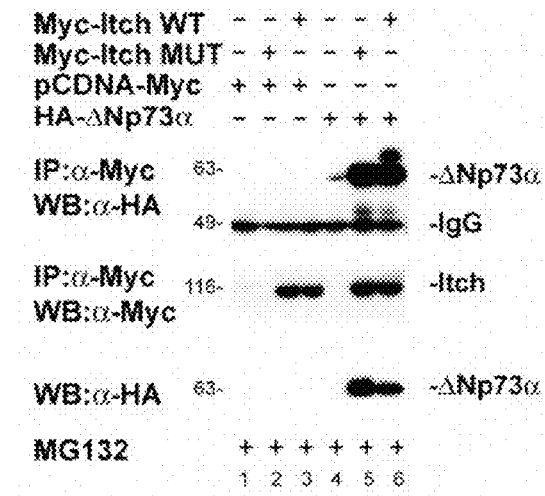
Figure 1F:
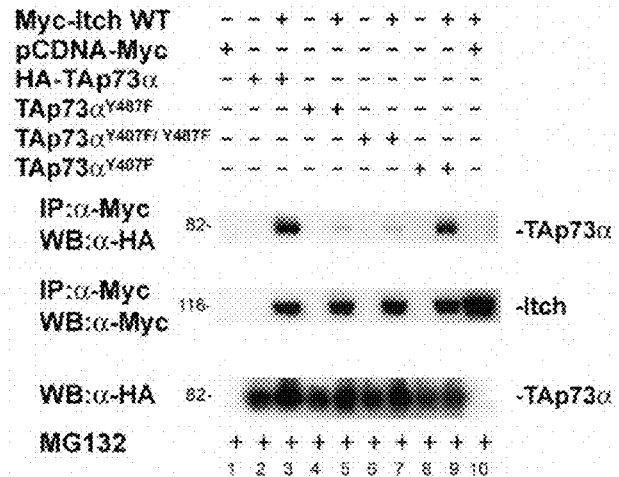
Figure 1G:
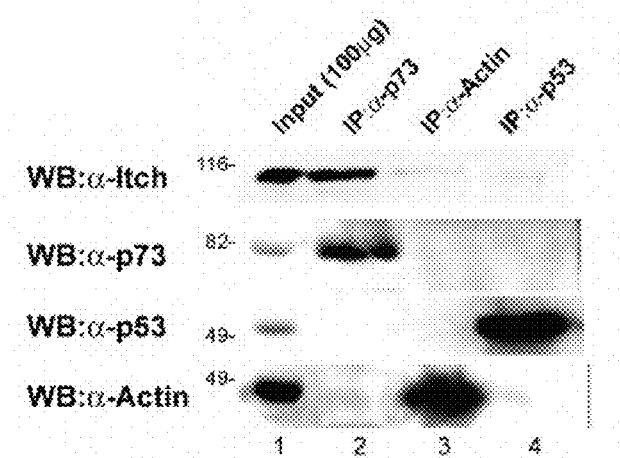

In order to verify that Itch associates with p73, we performed an in vitro pull down assay. Hek293 cells were transfected with either an empty vector or with a vector encoding HA tagged TAp73α. Cell lysates were mixed separately with a sepharose resin containing either GST or the WW region of Itch fused to GST (GST-WW). TAp73α was efficiently retained by GST-WW, while no significant binding to GST alone was detected (FIG. 1C). The interaction was also confirmed by co-immuno-precipitation (co-IP) of overexpressed TAp73α and Itch. As shown in FIG. 1D immuno-precipitation (IP) of Myc tagged Itch resulted in co-IP of TAp73α. Addition of proteasome inhibitor MG132 resulted in stronger interaction. As expected, since p53 does not contain the PY motif (FIG. 1A), it did not bind to Itch and could not be precipitated with Itch regardless of the presence of the proteasome inhibitor (FIG. 1D). Similarly, TAp73δ, that also lacks the PY motif (FIG. 1A) could not be co-IP with Itch (data not shown). The N-terminally truncated form ΔNp73 α also bound Itch (FIG. 1E). To confirm that the interaction requires the PY motif of p73 we generated mutants of both the PY motifs found in p73 (FIG. 1A). FIG. 1F shows that mutants containing the Y487F substitution lost the ability to bind Itch while the single mutant $TAp73\alpha_{Y407F}$ did not. In order to confirm that this interaction also occurs in cells at physiological concentrations, we performed co-IP of endogenous proteins (FIG. 1G). Again IP of endogenous p73 co precipitated Itch, while IP of p53 did not.

These data clearly demonstrate that endogenous p73 α isoforms can bind to the WW domains of Itch through their PY motif and that the interaction is selective for p73 and not shared by p53.

p73 is Ubiquitinated by Itch

Figure 2A:
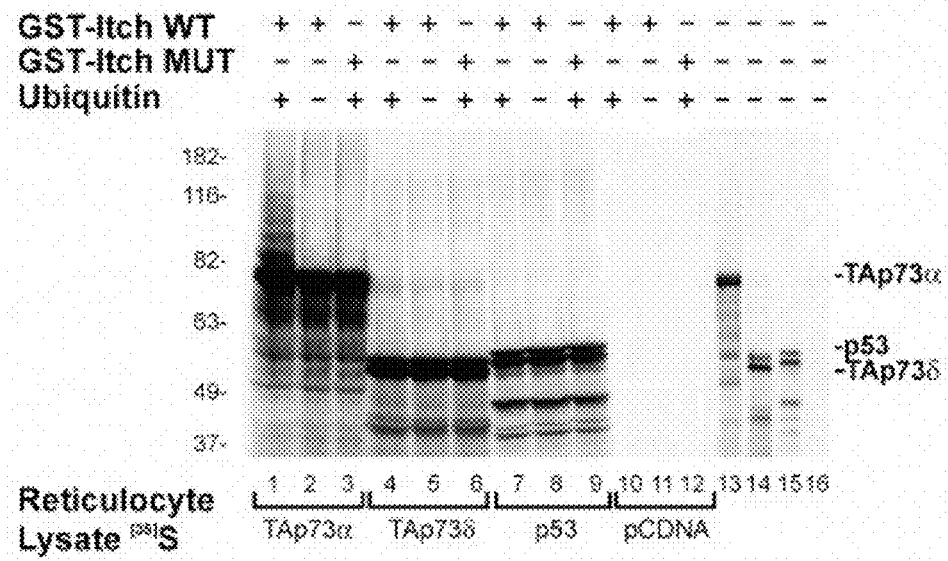

We next investigated whether p73 can serve as a substrate for the ubiquitin-protein ligase activity of Itch. We used a recombinant Itch (GST-Itch) (Qiu, 2000), in a reconstituted in vitro ubiquitination system containing Ub, wheat E1, human E2 (UbCH7), ATP, and in vitro synthesized radio labeled [$^{35}$S] TAp73α protein as substrate. In the presence of purified GSTItch, the TAp73α protein was ubiquitinated, as shown by the appearance of discrete higher molecular weight TAp73α species (FIG. 2A, lane 1). To demonstrate that the appearance of ubiquitinated forms of TAp73α requires an intact Itch Hect domain, we used a previously described inactive mutant of Itch (GST-Itch MUT) (C830A) (Winberg, 2000). As shown in FIG. 2A, this mutant, that retains the ability to bind TAp73α (FIG. 1D), lost the ability to promote TAp73α ubiquitination. The inability of Itch to ubiquitinate p73δ and p53 suggests that the PY motifs are required, since these two proteins lack these motifs (FIG. 1A and FIG. 2A lanes 4 and 7). These in vitro data also show that no other factor was required for this reaction to occur.

Figure 2B:
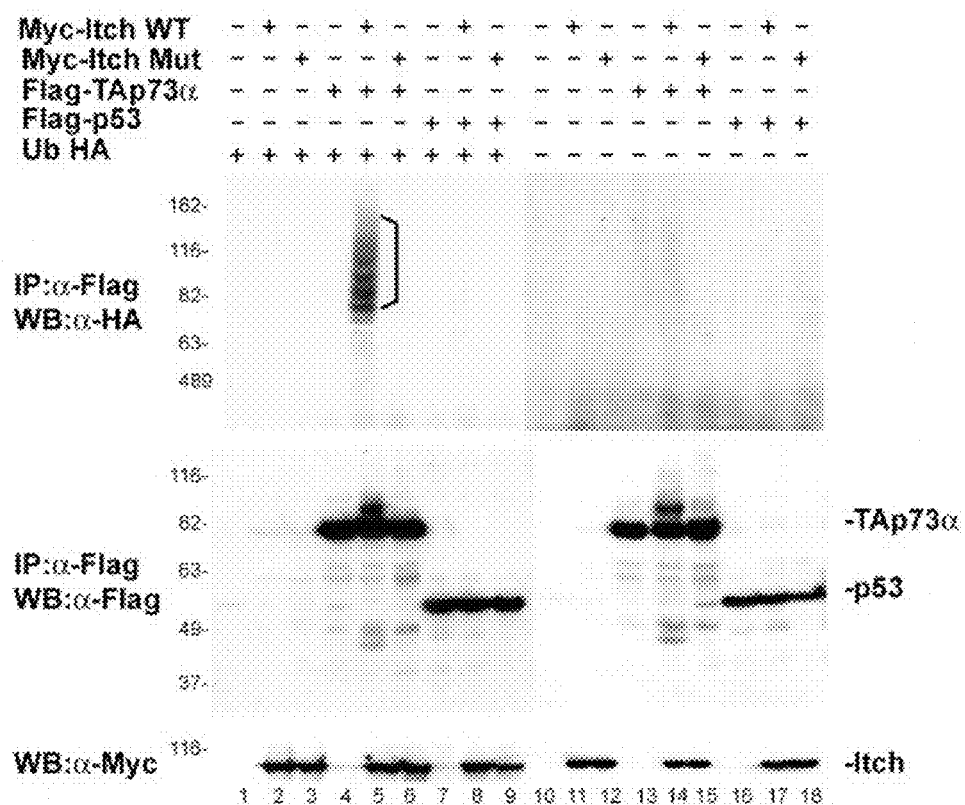
Figure 2C:
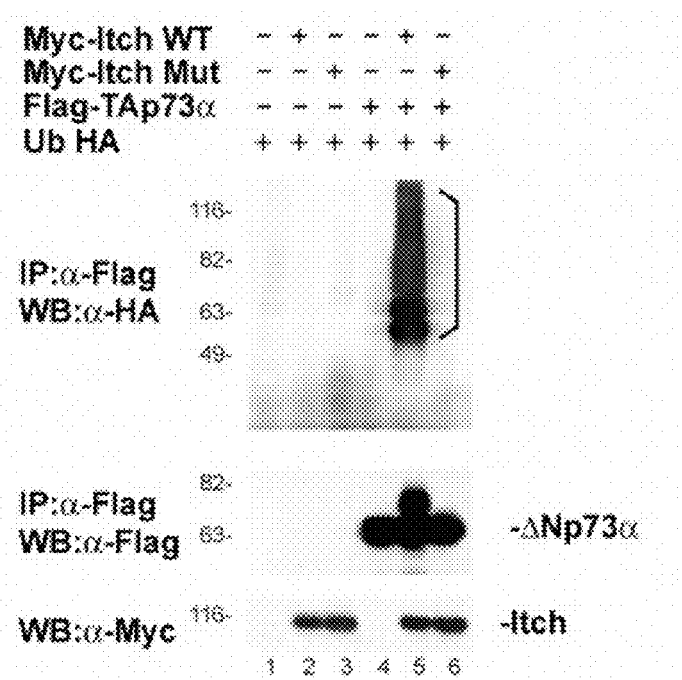
Figure 2D:
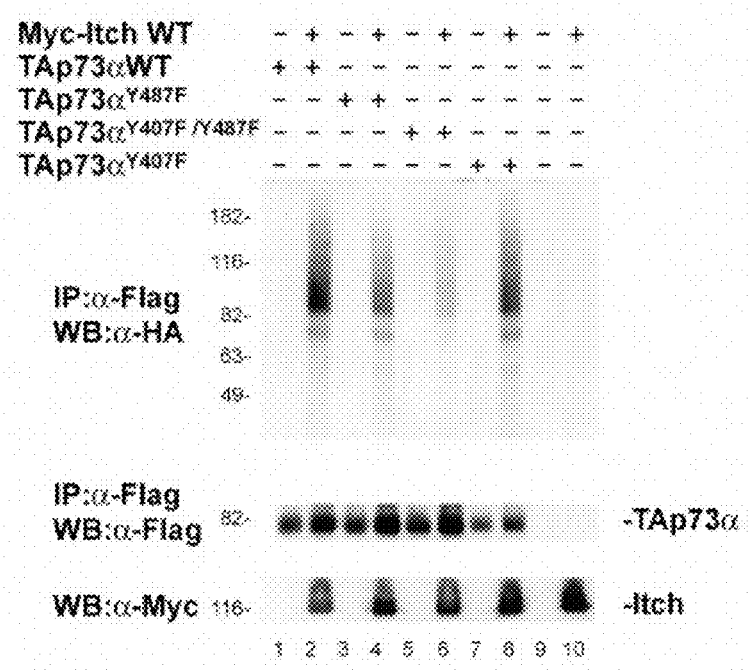

We next examined if Itch can catalyze p73 ubiquitination in cells. Extracts of Hek293 cells transfected with plasmids expressing: HA-tagged ubiquitin (Ub-HA), Myc-tagged Itch (Myc-Itch) and Flag-tagged TAp73α or p53 (Flag-TAp73 α and Flag-p53), were subjected to IP with anti-Flag antibodies and detected with anti-HA and anti-Flag western blots. As shown in FIG. 2B (lane 5), Ub-HA TAp73α conjugates were detected upon co-transfection only with wild type Itch (Myc-Itch WT), and not with the catalytically inactive mutant of Itch (Myc-Itch MUT) (FIG. 2B, lane 6). Similarly ΔNp73 α was ubiquitinated by Itch (FIG. 2C), showing that the N-terminal part of the protein is not required for the ubiquitination. In contrast, p53 was not ubiquitinated by Itch (FIG. 2B 7-9). Although ubiquitination of $TAp73\alpha_{Y487F}$ mutant was reduced, a greater reduction was seen with the double mutant $TAp73\alpha_{Y407F/Y487F}$ (FIG. 2D). Ubiquitination of the $TAp73\alpha_{Y407F}$ mutant was similar to that of wild type p73. The right panel (lanes 10-18) in FIG. 2B demonstrates the specificity of the reaction since no higher molecular weight bands were observed in the absence of Ub-HA. These data clearly show that p73 but not p53 is ubiquitinated by Itch, suggesting that this protein plays an important role in the regulation of p73 steady state protein levels.

Itch Regulates the Stability of p73 in Cells

Since ubiquitination of proteins is usually associated with their turnover (Weissman, 2001), we investigated if Itch can regulate p73 protein abundance. We measured TAp73α levels in whole cell extracts in the presence or absence of Itch. Representative data from several independent experiments demonstrate that co-expression of Myc-Itch and TAp73 cc in cells results in a striking decrease of TAp73α levels (FIG. 3A), indicating that the Itch-dependent ubiquitination targets p73 for degradation. Consistently, the catalytic mutant of Itch was not able to alter the concentration of p73 (FIG. 3A, lane 3) and the $TAp73\alpha_{Y487F}$ (FIG. 3B) mutant levels were not affected by Itch over-expression.

Because poly-ubiquitination generally targets proteins for proteasomal degradation (Weissman, 2001), we determined the effect of MG132 on the steady state levels of TAp73 cc. As shown in FIG. 3A (lanes 4-6), addition of MG132 to cells blocks the Itch-mediated TAp73α degradation and resulted in the accumulation of the ubiquitinated forms of TAp73 α (data not shown). This is consistent with previous reports showing that proteasome inhibition leads to the stabilization of endogenous p73 protein (Balint, 1999). Again TAp736 and p53 levels were not affected by Itch (FIG. 3A).

Figures 3C, 3D:
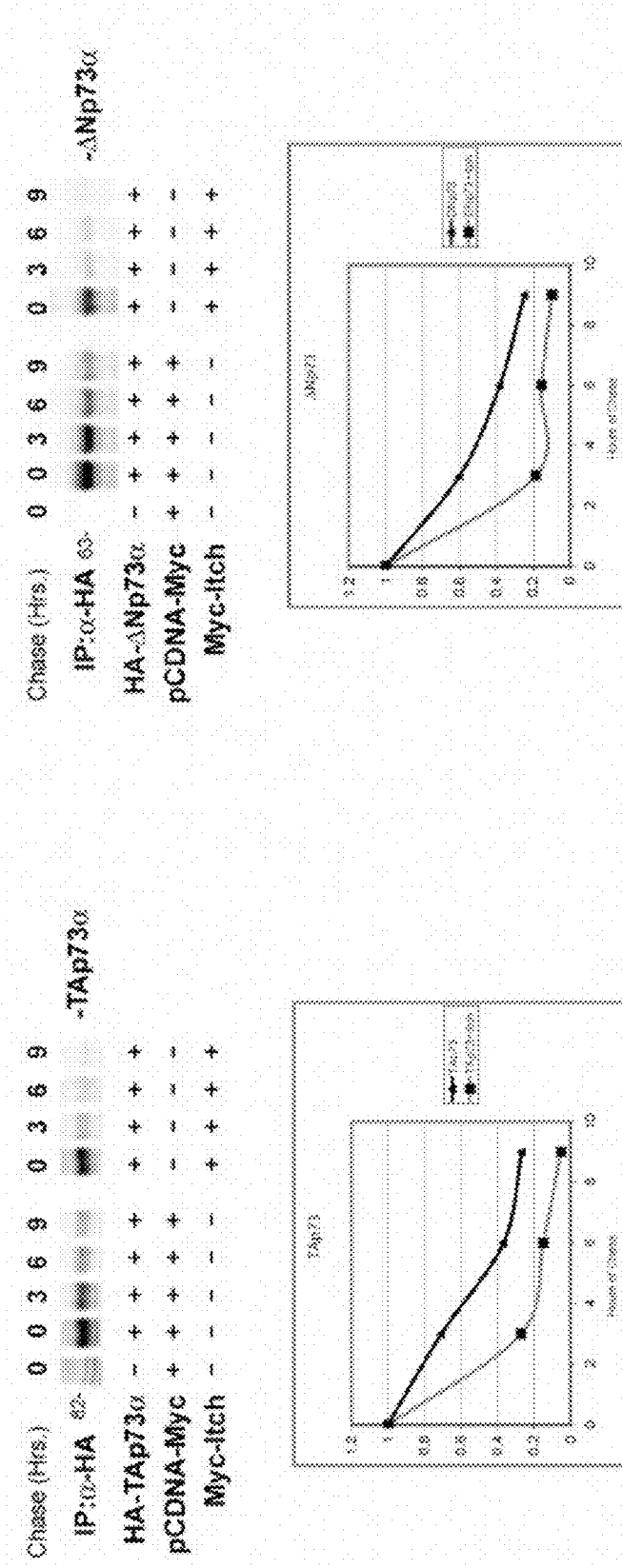
Figures 4A, 4B:
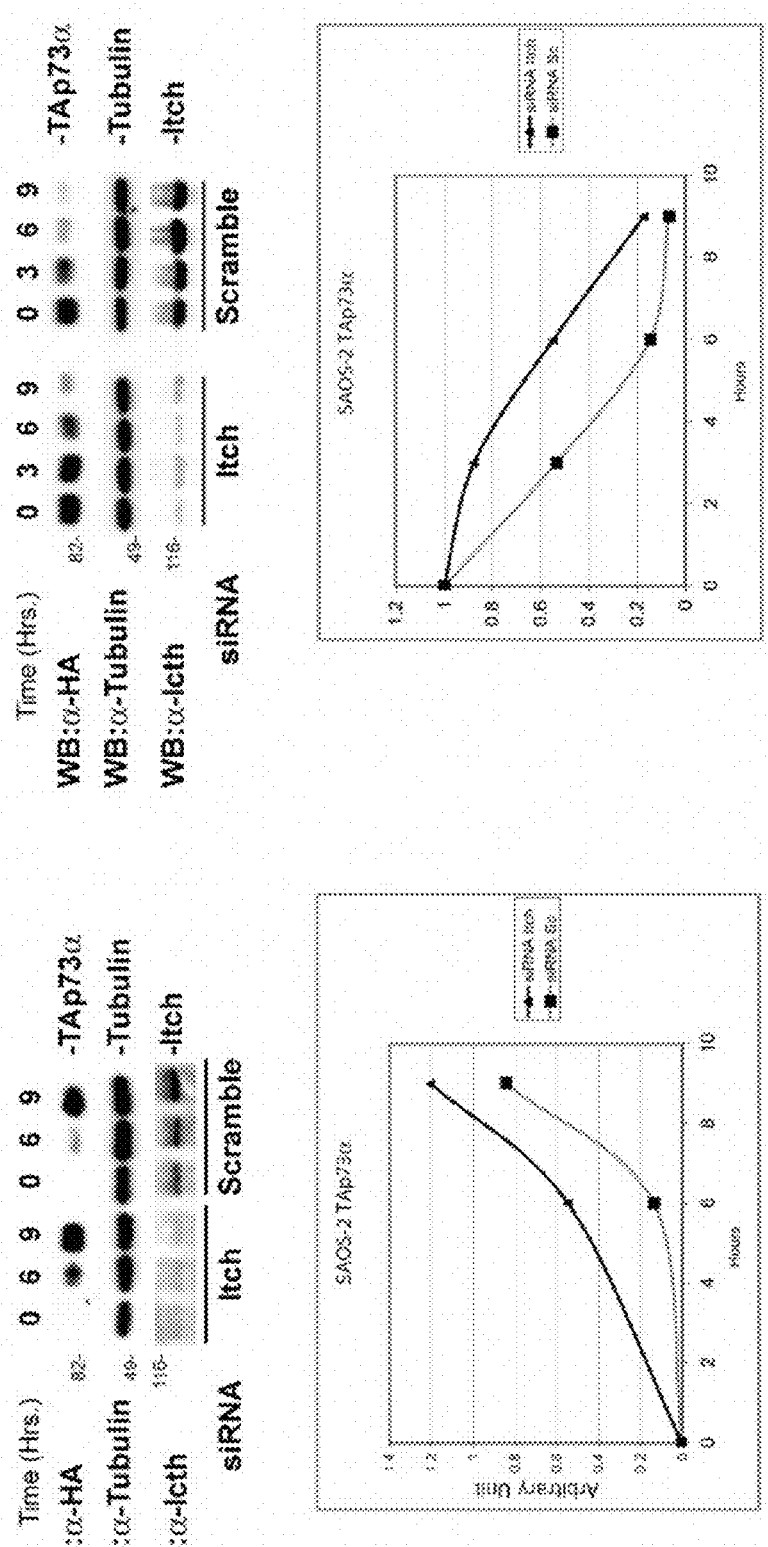

We further confirmed these results by measuring p73 half-life in the presence or absence of Itch using two different methods. Both pulse chase using $^{35}$S labeled Met and Cys (FIG. 3C-D), and cycloheximide blockade (FIG. 3 E-F), showed a marked decrease of TAp73 and ΔNp73 half lives in the presence of Itch. Under similar experimental conditions no change in p53 half-life was observed (FIG. 3G). To further confirm the importance of Itch in controlling p73 steady state levels we reduced endogenous Itch levels by siRNA. To this end we used Tet-On inducible Saos-2 cells expressing p73 (Melino et al., 2004). FIG. 4A shows that, in this inducible cell line, reduction in Itch expression by siRNA resulted in more rapid induction and higher levels of p73 protein. Moreover, after withdrawal of induction, p73 levels decline more slowly when Itch expression is reduced (FIG. 4B).

Figure 4C:
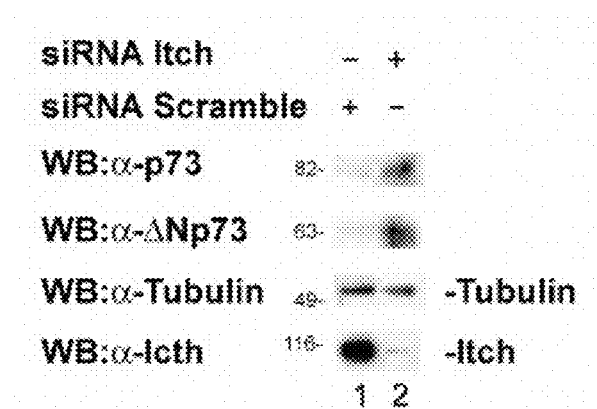
Figure 4D:
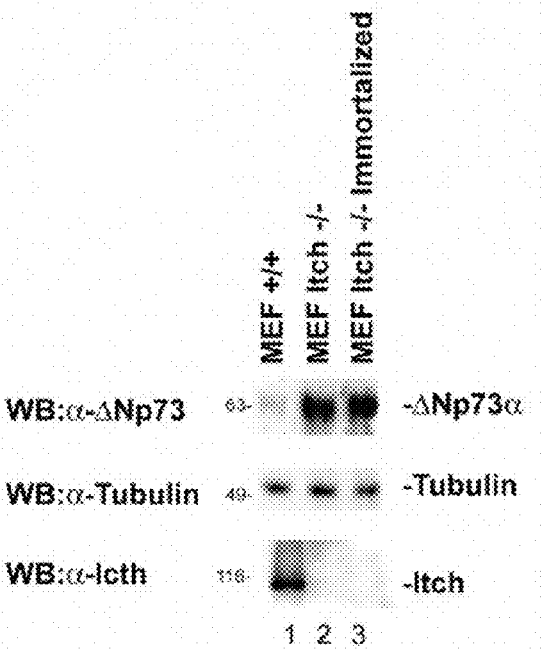
Figure 4E:
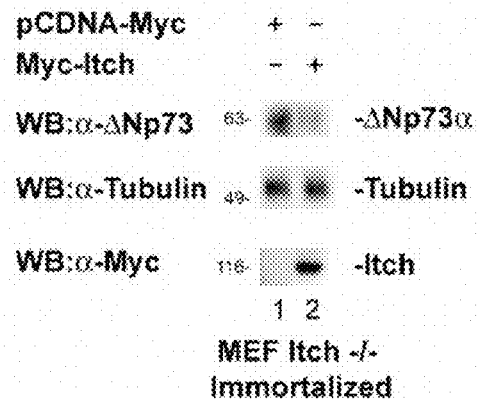

Similarly the steady state levels of endogenous TAp73 and ΔNp73 isoforms increased in Saos-2 cells when Itch was down regulated (FIG. 4C). This confirms that basal Itch levels are important in controlling basal p73 levels. In agreement, endogenous levels of ΔNp73 (which is the only isoform detectable in these cells) were increased in mouse embryo fibroblasts (MEFs) derived from non-agouti-lethal 18H Itch deficient mice (MEF Itch−/−) (FIG. 4D). Re-introduction of wild type Itch into MEFs Itch−/− resulted in reduction of endogenous ΔNp73 levels in these cells (FIG. 4E).

Figure 5B:
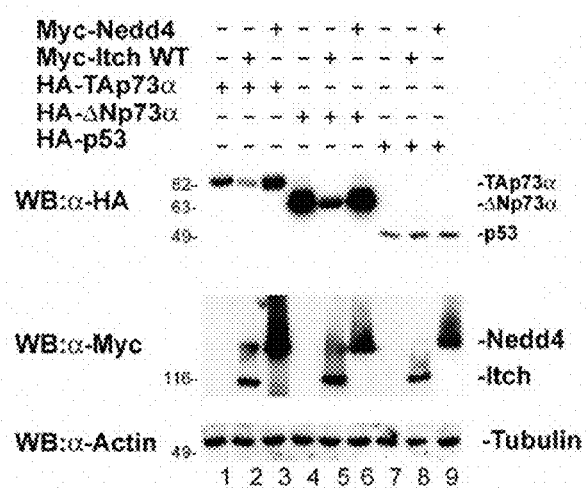
Figure 5C:
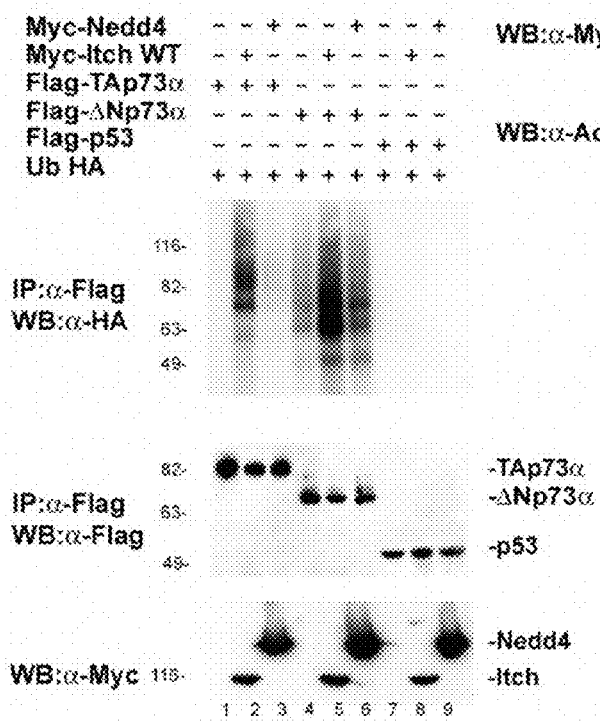

Not all Itch family members had the same effect on p73. Nedd4 bound (FIG. 5A) both TAp73 and ΔNp73 but was not capable of catalyzing the ubiquitination of these proteins (FIG. 5C) and therefore did not affect their degradation (FIG. 5B). Miyazaki and colleagues (Miyazaki et al., 2003) demonstrated that NEDL2, another Nedd4 family member, binds, ubiquitinates and stabilizes p73. Thus, different Nedd4-like E3 ligases, although all capable of binding the p73 PY motifs, exert different effects on these proteins.

Itch Decreases p73-Dependent Transcriptional Activity

Figure 6A:
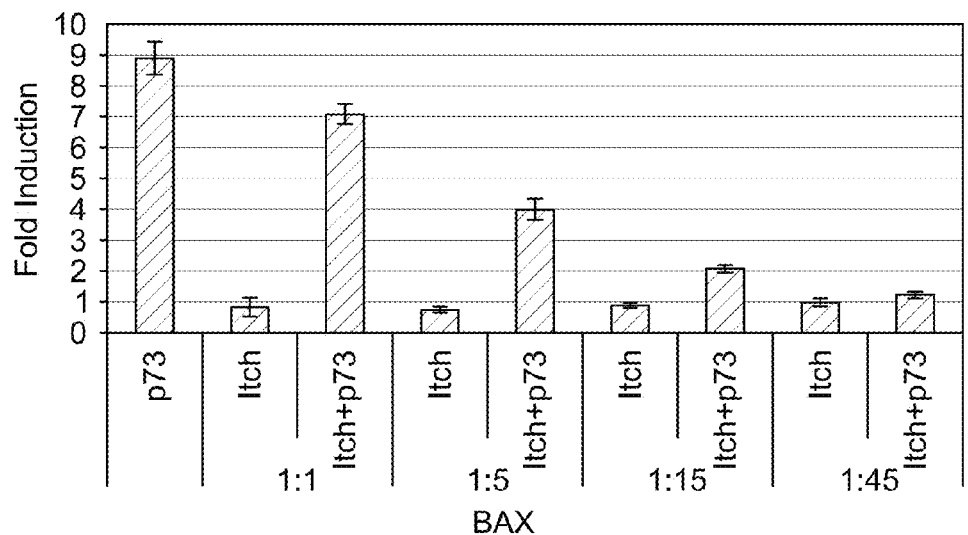
Figure 6B:
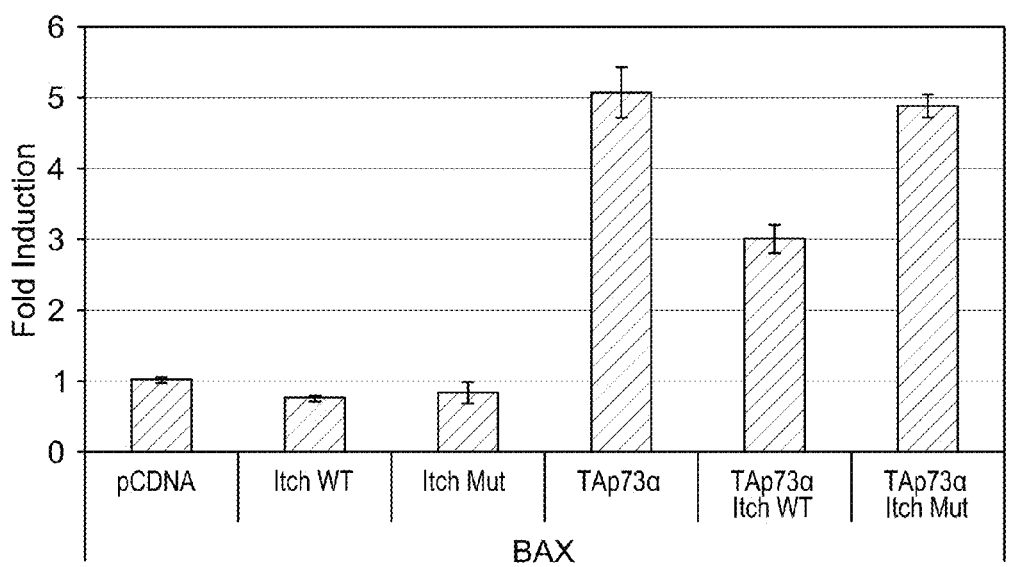
Figure 6C:
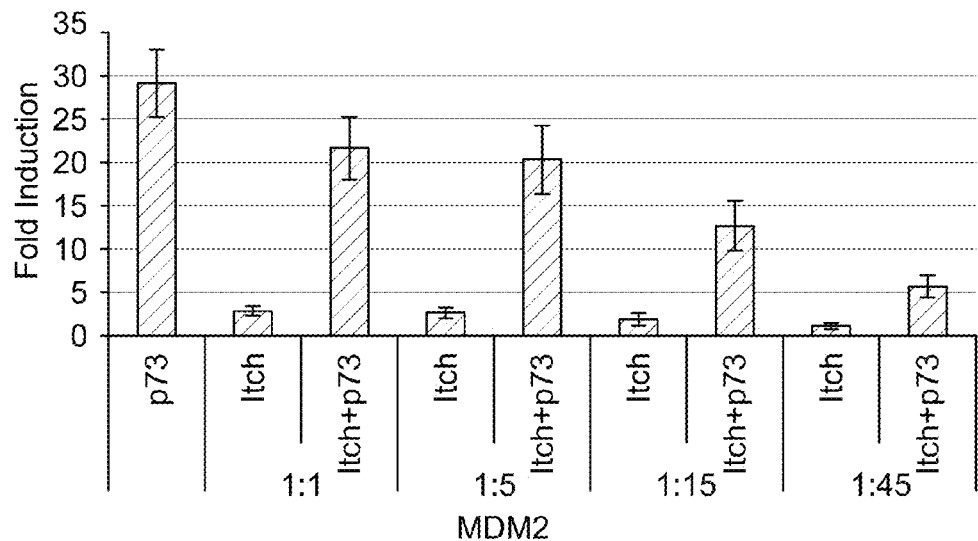
Figure 6D:
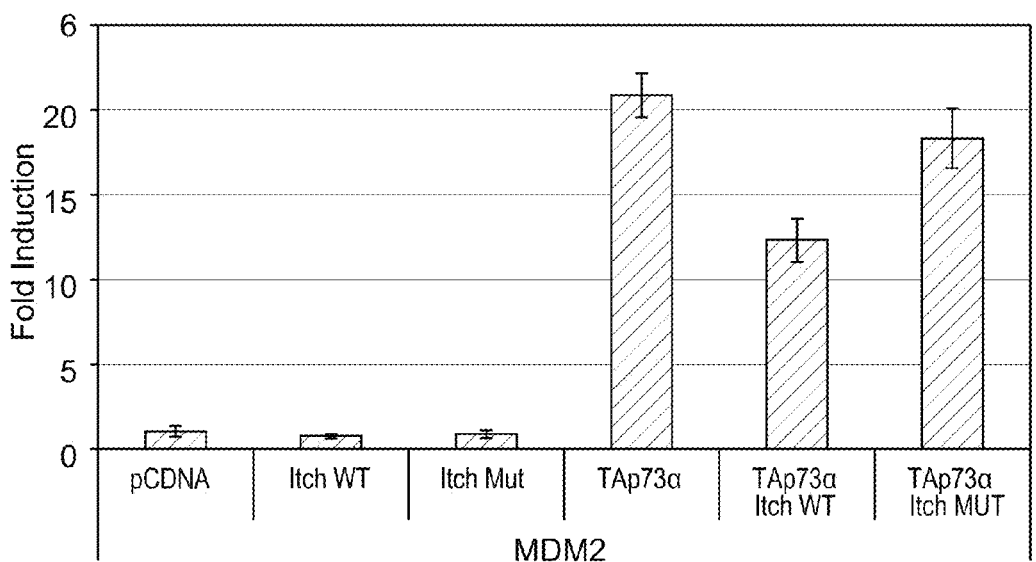
Figure 6E:
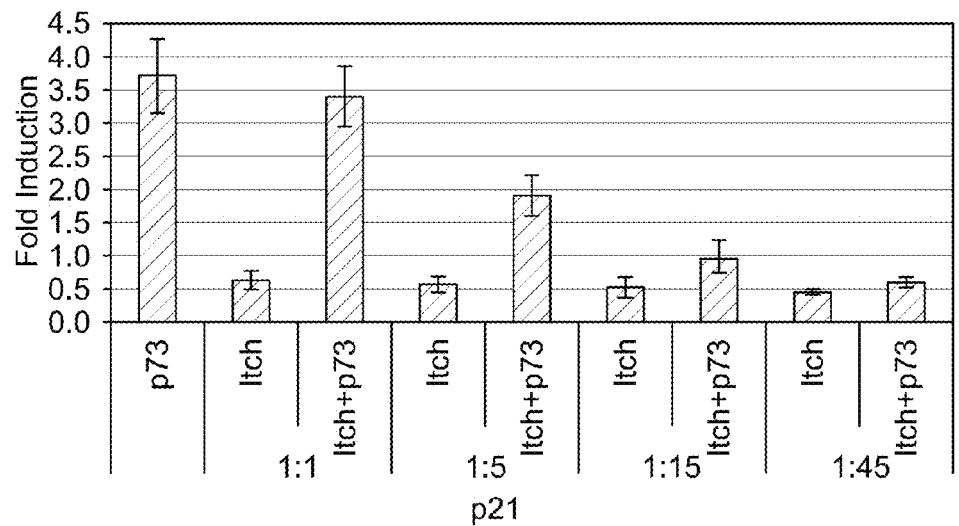
Figure 6F:
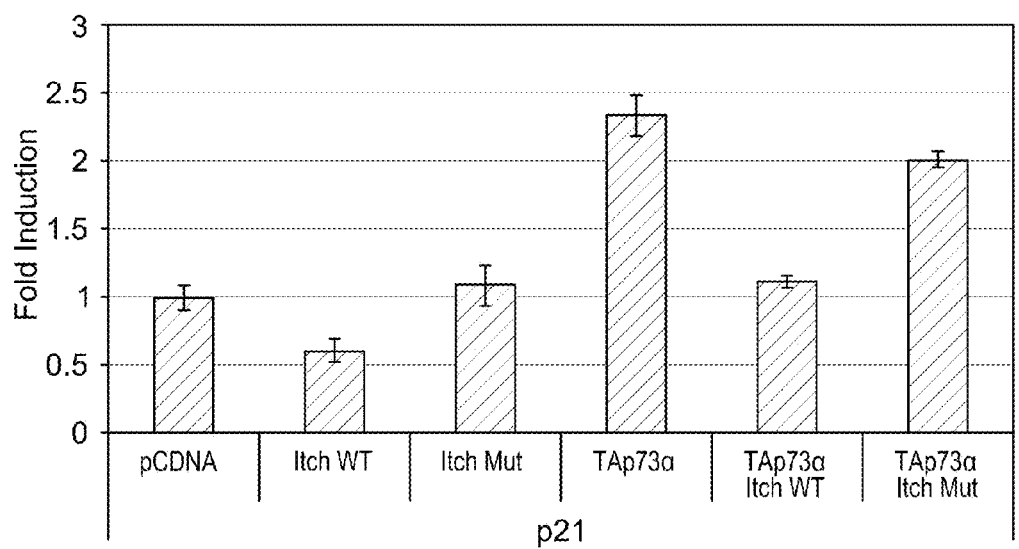
Figure 6G:
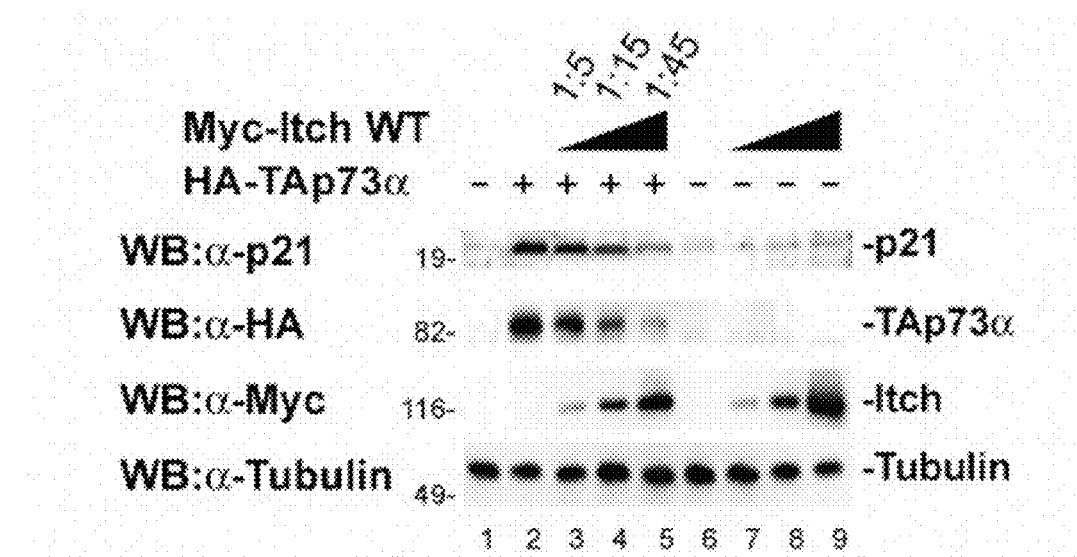

To evaluate if the interaction between p73 and Itch influences its transcriptional activity, we co-transfected H1299 cells with TAp73α and Myc-Itch or Myc-Itch MUT and assessed TAp73α transcription activity by luciferase reporter assay using different p53/p73 responsive promoters (Bax, p21 and MDM2). As shown in FIG. 6 (A-C-E), consistent with a reduction in TAp73 protein levels, co-transfection of Myc-Itch reduced the transcriptional activity of TAp73 α on all the promoters tested in a dose dependent manner. As expected the mutated form of Itch had no effect on the transcriptional activity of p73 (FIG. 6B-D-F). The reduction of the promoter activity was paralleled by a reduction in endogenous levels of p73 target proteins such as p21 (FIG. 6G).

Itch is Down Regulated in Response to DNA Damage

Figure 7A:
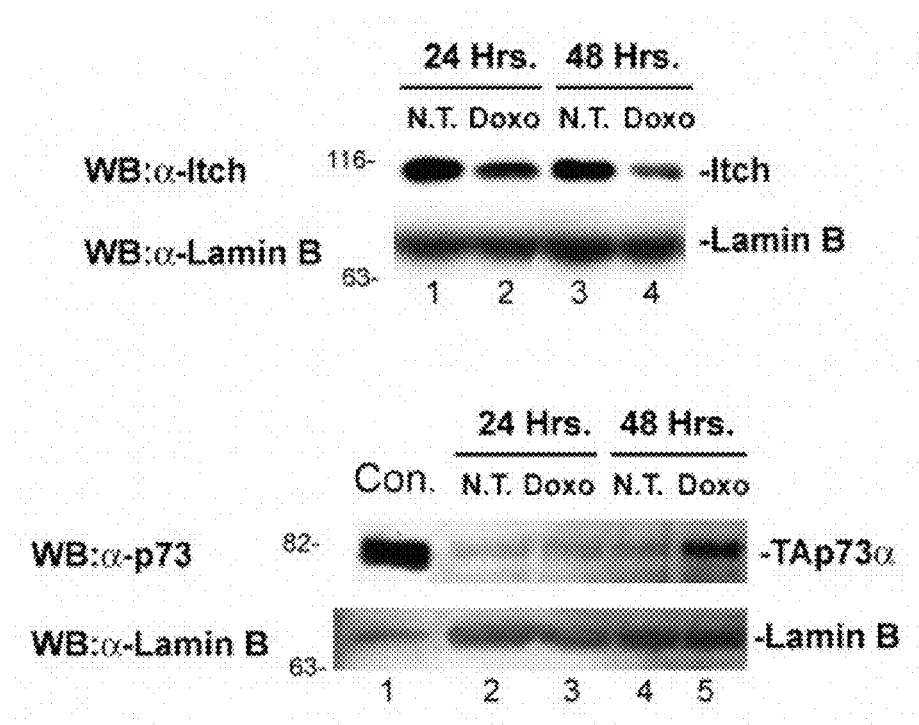
Figure 7B:
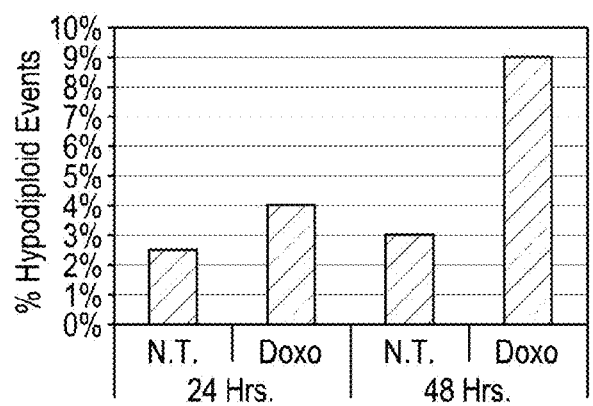
Figure 7C:
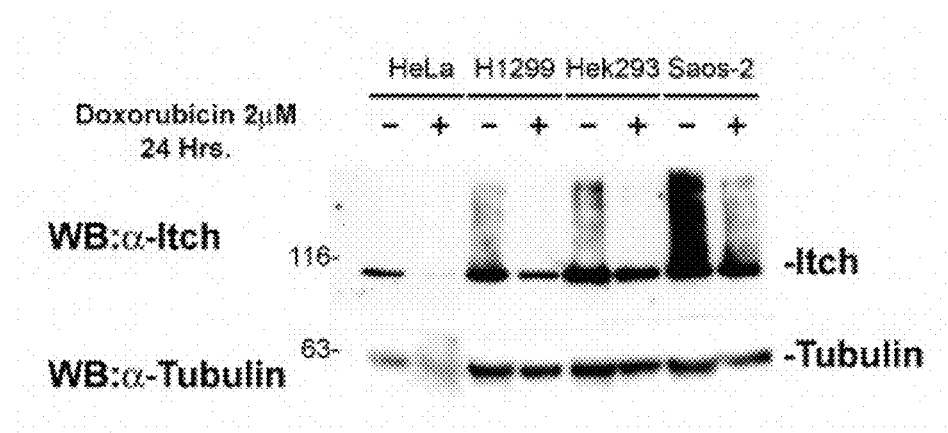

Since TAp73 protein levels increase in response to DNA damage (Agami, 1999; Gong, 1999; Yuan, 1999) we investigated if Itch expression is also modulated after DNA damage. In Saos-2 cells, following treatment with doxorubicin, to induce DNA damage, endogenous Itch protein levels were down-regulated in a time (FIG. 7A) and dose (not shown) dependent manner. The reduction of Itch levels was paralleled by an increase in endogenous TAp73 levels (FIG. 7A). Reduction of Itch also paralleled an increase in apoptosis (FIG. 7B). This response of Itch to doxorubicin treatment is not cell type specific: FIG. 7C shows a similar experiment using HeLa, H1299 and Hek293 cell lines treated with doxorubicin. These results suggest that Itch could be an important regulator of TAp73 levels and that upon DNA damage Itch is down regulated allowing TAp73 levels to rise. FIG. 9 shows that down-regulation of Itch by siRNA sensitizes cells to doxorubicin.

Figure 7D:
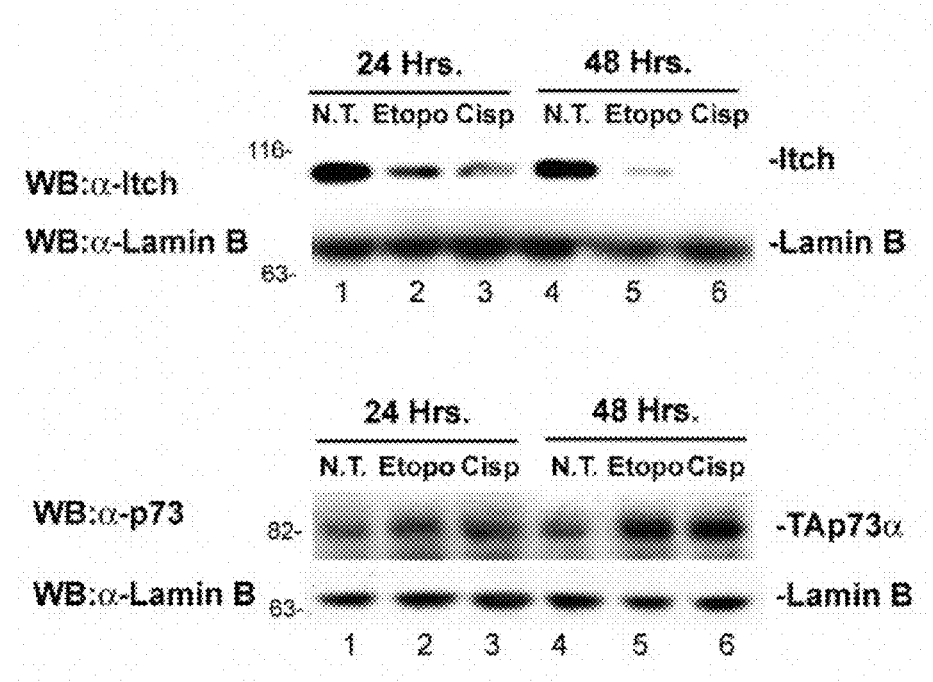
Figure 7E:
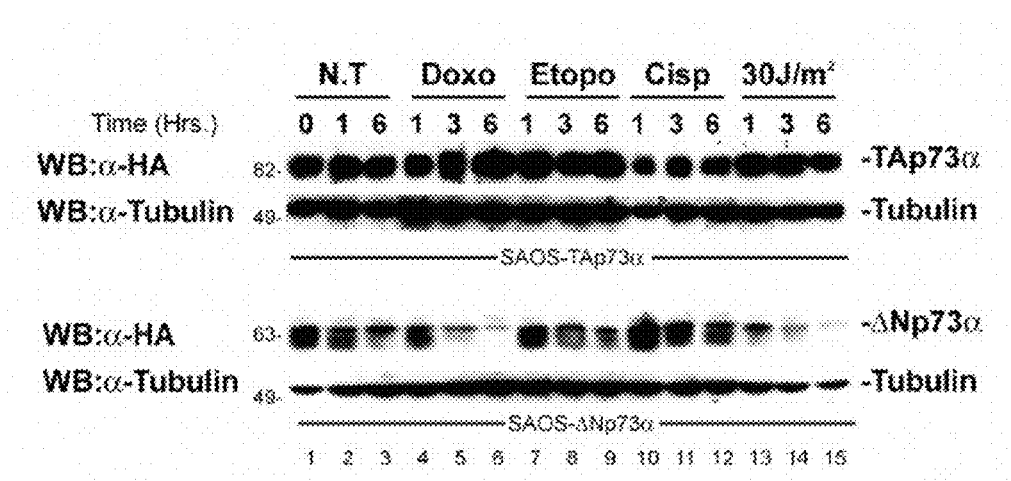
Figure 7F:
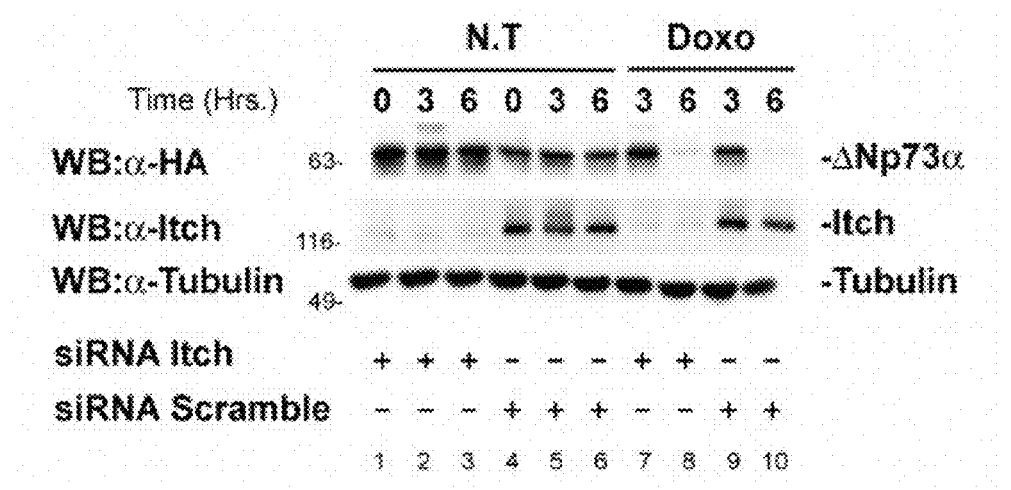

This pathway is p53 independent since the effect on cell cycle and apoptosis was also observed in cell lines lacking p53 such as Saos-2. The DNA damage-dependent decrease in Itch levels is not specific for doxorubicin treatment but also occurs when cells are treated with other DNA damaging agents. As shown in FIG. 7D treatment with cisplatin and etoposide also resulted in a dramatic reduction in Itch protein levels. Since Itch also affects ΔNp73 levels an increase of this isoform would also be expected in response to DNA damage. FIG. 7E, however, shows that as we have previously published (Maisse et al., 2004), ΔNp73 α unlike TA is rapidly degraded upon DNA damage regardless of the down-regulation of Itch. In order to confirm that ΔNp73 degradation is independent of Itch we reduced Itch levels in the Saos-2-ΔNp73 cc inducible cell line, and then induced ΔNp73 expression by the addition of doxycycline. The inducer was removed and DNA damage was then induced with doxorubicin. As shown in FIG. 7F reduction of Itch levels results in increased stabilization of ΔNp73 cc but does not prevent its degradation in response to doxorubicin treatment.

Discussion p73 activity depends on its steady state protein levels and a variety of evidence suggests that post-transcriptional regulation rather than transcriptional control plays a major role in p73 response to DNA damage. Upon DNA damage, p73 becomes activated and stabilized (Catani, 2002), and this results in cell cycle arrest and apoptosis (Agami, 1999; Gong, 1999; Yuan, 1999). p73 is rarely mutated in cancers, although altered levels of one or more isoforms of p73 have been found in tumors (Casciano, 2002; Ikawa, 1999; Melino, 2002; Putzer, 2003; Romani, 2003; Tschan, 2000). Little is known about the pathways leading to p73 degradation, despite the likely importance of its consequences in cancer development and therapy.

Endogenous p73 steady state levels increase in the presence of proteasome inhibitors, suggesting a role for this pathway in p73 degradation (Balint, 1999; Ongkeko, 1999; Zeng, 1999). While the homology with p53 suggests that Ub-protein ligase MDM2 could be the required E3 ligase, MDM2 binding to p73 does not lead to p73 ubiquitination and degradation but instead leads to p73 stabilization (Balint, 1999; Dobbelstein, 1999; Lohrum, 1999; Ongkeko, 1999; Zeng, 1999).

We have recently reported that, upon activation of p38 MAP kinase, p73 is recruited into the PML-NB and acetylated by p300. Acetylation protects TAp73 from ubiquitination resulting in its stabilization (Bernassola et al., 2004). NEDL2 a HECT-type E3 ligase has also been reported to bind and ubiquitinate p73 resulting in its stabilization rather than degradation (Miyazaki et al., 2003). Regulation of p73 stability, and particularly that of its different isoforms, is therefore complex and far from fully understood.

Here, we demonstrate that Itch selectively binds and ubiquitinates p73 C: In contrast, it has no such effect on p53. Our results also show a different regulation among the various C-terminal isoforms of p73 since only the α and β isoforms that contain the PY motif are regulated by Itch while the δ and γ isoforms that lack this domain escape this regulation. We found that Itch is rapidly down-regulated in response to DNA damage allowing p73 levels to increase. Therefore, this response to DNA damage, selective for p73 and independent of p53, may be important in p53 negative tumors. This is supported by descriptions, for example, in Cell, 2004, 119(6): 861-72 and Cell, 119(6):847-60.

We have recently shown that unlike TAp73, the ΔNp73 isoforms are rapidly degraded in response to DNA damage (Maisse et al., 2004). Our results show that ΔNp73 isoforms are also Itch substrates and Itch down-regulation results in increased ΔNp73 levels. The down-regulation of Itch in response to DNA damage should therefore result in a parallel increase of TAp73 and ΔNp73 forms. This however is not the case and while TAp73 levels actually rise, ΔNp73 is rapidly degraded (Maisse et al., 2004). In our model, Itch seems to be responsible for keeping both TAp73 and ΔNp73 levels low under normal condition (FIG. 8). Upon DNA damage, Itch reduction allows stabilization of both TAp73 and ΔNp73. Therefore, a second pathway should specifically target ΔNp73 for degradation. Recently Toh et al. describe the ability of c-Jun to regulate the stability of p73 (Toh et al., 2004). Even though the underlying molecular mechanism was not elucidated, here c-Jun affects stability of TAp73 and not ΔNp73, indicating a differential effect on the two major p73 isoforms. In conclusion we provide a mechanism by which p73 levels are normally kept low in cells, in accordance with the low basal levels found in many tissues and cell lines, and are increased in response to DNA damage (FIG. 8).

Example 2

An Interaction Between p63 and ITCH

Methods

Plasmids

Myc-Itch and Myc-Itch MUT plasmids (C830A) were provided by Dr. T. Pawson. Flag-TAp63α and Flag-ΔNp63α were obtained by subcloning the cDNA TAp63α and ΔNp63α into NheI and NotI sites of the pCDNA3.1. The HA-ubiquitin construct (HA-Ub) was kindly provided by Dr. D. Bohmann.

Cell Culture and Transfection

Human embryonal kidney cells (Hek293), HeLa cells and MEFs were grown in Dulbecco's modified Eagle medium (DMEM) (GibcoBRL); the human lung carcinoma cells H1299 and the human osteosarcoma cells Saos-2 were cultured in RPMI (GibcoBRL). Itch−/− MEF cells were prepared from Itch$^{-/-}$ mice (Y-C-Liu) or they were generous gift from Neil Copeland, Lynda Matesic, Nancy Jenkins. All media were supplemented with 10% (v/v) fetal bovine serum (FBS) (GibcoBRL). All cell lines were grown at 37° C. in a humidified atmosphere of 5% (v/v) $CO_2$ in air. Transient transfection was performed with lipofectamine 2000 reagent according to the manufacturer's instructions. Apoptosis was analysed by flow cytometric evaluation of DNA fragmentation.

Western Blot and Antibodies

Proteins were separated on SDS-PAGE and blotted onto nitrocellulose membranes. Filters were blocked with TBST 5% non-fat dry milk and incubated with primary antibodies for 2 hrs at room temperature (RT). Filters were incubated for 1 hour at RT using the appropriate horseradish peroxidase-conjugated secondary antibody (rabbit and mouse BioRad; goat Santa Cruz). Detection was performed with the enhanced chemiluminescence Supersignal West Pico (Pierce). Endogenous Itch was detected with a mouse monoclonal antibody (BD Bioscience), Actin (sc-1615) polyclonal goat antibody (Santa Cruz), β-Tubulin (sc-9104) polyclonal rabbit antibody (Santa Cruz), c-Myc-tagged constructs were detected or immuno-precipitated with the sc-40 monoclonal mouse antibody (Santa Cruz) and the Flag-tagged constructs with the M2 monoclonal mouse antibody (Sigma).

Immunoprecipitation

Following a previously published procedure (Gottifredi, 1999) Hek293 cells were transiently transfected with 8 µg of total DNA of the indicated mammalian expression plasmids and harvested 48 hours after transfection. Cells were then lysed as described above. Following preclearing for 1 h at 4° C., we performed immunoprecipitation by incubating 1.5 mg of whole-cell extracts with the indicated antibodies, rocking at 4° C. for 1 hour. The immuno-complexes were collected by incubating with protein G Agarose (KPL), washed with Net-gel buffer (50 mM Tris pH 7.5, 150 mM NaCl, 1 mM EDTA, 0.25% gelatin, 0.1% NP40). The beads were then resuspended in 5× Laemmli buffer, and subjected to western blot with the indicated primary antibodies.

Ubiquitination Assays

Hek293 cells were transiently transfected with mammalian expression plasmids for HA-tagged ubiquitin (HA-Ub), with the indicated combination of plasmids. 48 hrs after transfection, cells were harvested, the insoluble fraction was removed by a high-speed spin, and 1 mg of total cellular proteins of the clarified supernatant was subjected to immunoprecipitation using anti Flag antibodies (Sigma). Ubiquitin-conjugates were detected by Western immunoblot analysis using anti-HA-antibodies (Santa Cruz).

Measurement of p63 Half Life

Decay of p63 protein levels in the presence of cycloheximide. Cycloheximide (20 µg/ml) was added to Hek293 cells 24 hours after transfection with a total of 3 µg of the indicated plasmids in a 1:5 ratio TAp63/Itch and ΔNp63/Itch. Protein levels were determined by collecting cells at the indicated time points and performing immunobloffing as described above. The relative amount of p63 protein was evaluated by densitometry and normalized on β-Tubulin.

Steady State Protein Levels Analysis

Levels of TAp63α αν α ΔNp63α were determined 48 hrs after co-transfection with HA-TAp63 and HA-ΔNp63α, in the presence or absence of Myc-Itch or Myc-Itch MUT. 25 µg of cell lysates were subjected to Western blotting. p63 proteins were detected using an anti-HA antibody. The same blots were re-probed with anti-Myc antibody to detect Itch and with anti-Tubulin antibody as loading control.

Results and Discussion

ITCH Interacts with p63α.

p63α, as well as p73α, has a proline-rich region at its C-terminus, which is present in both the TA and ΔN isoforms and is known to interact with WW domains, such as those present in ITCH. We tested if ITCH interacts with Tap63α and ΔNp63α proteins by performing co-immunoprecipitation (co-IP) experiments in 293T cells. We found that ICTH predominantly interacts with the ΔNp63α isoform (FIG. 10). We are currently testing whether mutation of the proline-rich domain results in the loss of binding to ITCH. Previous studies showed that the TA transactivation domain of p63α is likely to be involved in intramolecular interactions that can mask C-terminal sequences. Thus, it is conceivable that the proline-rich region of p63α is more accessible in ΔN isoforms, thus allowing the interaction with proteins containing a WW domain, such as ITCH.

ICTH Ubiquitinates p63α.

As ITCH interacts with p63α, we next assessed whether p63α can serve as a substrate of the ubiquitin ligase activity of ITCH. To this end, we overexpressed ITCH together with TAp63α and ΔNp63α and HA-tagged ubiquitin and analyzed the ubiquitination levels of p63 (FIG. 11). As expected based on the results of the coIP experiments, only ΔNp63α ubiquitination was markedly induced by ITCH (FIG. 11), thus demonstrating the functional consequences of ITCH/p63 interaction.

p63α Steady State Levels and Half-Life are Affected by ITCH.

In order to determine whether ITCH-dependent ubiquitination of p63α promotes its downregulation, we measured steady state levels of p63 isoforms in the presence or absence of ITCH. While TAp63α levels were not significantly affected by ITCH, ΔNp63α protein levels were markedly reduced in cells expressing ITCH (FIG. 12). To prove that the reduced levels were due to increased degradation, we analyzed the half-life of both TAp63α and ΔNp63α in cells expressing ITCH (FIG. 13). In agreement with the observed decrease in steady state levels of ΔNp63α by ITCH, the half-life of ΔNp63α was significantly reduced in the presence of ITCH (FIG. 13A), while the half-life of TAp63α was only marginally affected (FIG. 13B).

In conclusion, our findings clearly show that p63, like p73, is a target of ITCH-dependent ubiquitination and subsequent degradation. While both TAp63α and ΔNp63α isoforms are regulated by ITCH, mainly the ΔNp63α isoform serves as a substrate of ITCH. p63 is expressed in the stem cell compartment of many different epithelia. This suggests that ITCH could play a fundamental role in the differential regulation of p63 isoforms during epithelial differentiation, therefore implying that it could be instrumental in the restriction of p63 expression to the stem cell compartment.

Moreover, the observation that Itch selectively targets ΔNp63 for ubiquitination and degradation is relevant to epithelial cancers. As discussed above, ΔNp63 expression is increased in the common prostate and breast carcinomas, suggesting that its selective degradation is compromised. Under these circumstances, therefore, we may be looking for compounds which either activate Itch, or induce alternative selective ubiquitination pathways for ΔNp63.

Recent data have implied that disruptions in the balance between TAp63 and ΔNp63 isoforms in epithelial tissues may be of greater importance in tumorigenesis than direct gene mutation (Park et al., 2000). ΔNp63 isoforms may indeed confer a proliferative advantage on cancer cells by counteracting the transactivation activities of p53 and TAp63 proteins and, hence, their ability to induce cell cycle arrest and apoptosis (Crook et al., 2000). Interestingly, ΔNp63 is the most highly expressed isoform in squamous cell, prostate and breast carcinomas (Nylander et al., 2002). In addition, loss or impaired expression of TAp63, possibly caused by altered proteasome-dependent degradation, has been associated with tumour progression and poor prognosis in most invasive bladder cancers, which, conversely, display concomitantly up-regulation of ΔNp63 (Urist et al., 2002). Hence, the relative up-regulation of ΔNp63 vs TAp63 isoforms in cancers may contribute to promote tumour growth and chemotherapy resistance. Interestingly, loss or reduction of PML protein expression has been found in human cancers of various histologic origins including epithelial tumours such as prostate and breast carcinomas, in which it was associated with tumour grade and progression (Gurrieri et al., 2004). The ability of PML to increase the stability and transcriptional activity of p63 as well as of the other family members provides an explanation for how loss of PML protein would favour tumour initiation and enforces the notion that p63 may contribute to tumorigenesis.

Example 3

Effects of Down-Regulation of Itch in Cancer Cell Lines

Materials and Methods
Cell Culture and Transfections

H1299 and Saos-2 were grown in RPMI medium (Gibco-BRL 31870), and HeLa, MCF7, HEK293, HEK293T, A549, A431, Cos-1, cells were grown in Dulbecco's modified Eagle's medium (GibcoBRL 61965), U2OS and HCT116 were grown in McCoy's 5A media (GibcoBRL), SH-SY5Y were grown in 50% F12/50% DMEM (Gibco 31330). All media were supplemented with 10% (vol/vol) fetal bovine serum (GibcoBRL), and cells were cultured at 37° C. in a humidified atmosphere of 5% (vol/vol) CO2 in air. Transient transfections were performed with Lipofectamine 2000 or Calcium Phosphate reagents according to the protocol of the manufacturer (Invitrogen).

Plasmids

The pSUPER-ITCH2, pSUPER-ITCH18 and pSUPER-scrambled vectors were generated by insertion in pSUPER vector (OligoEngine) of oligos targeting the following sequences:

```
ITCH 2,     AAACATTAAAGTCAAACAATATG,

ITCH 18     AAGGAGCAACATCTGGATTAATA,
```

(These sequences are 100% identical both in human and mouse ITCH); and a scrambled shRNA control.

Western Blot

Samples were separated by sodium dodecyl sulfate-polyacrylamide gel electrophoresis (SDS-PAGE) and transferred onto polyvinylidene difluoride (PVDF) membranes by means of a semidry blotter. The membranes were blocked with 5% nonfat dry milk powder in Tris-buffered saline-0.05% Tween 20 for 1 h. Immunodetection was performed by incubating the membranes with the different primary antibodies diluted in blocking buffer for 2 h at room temperature or overnight at 4° C. After four washes with Tris-buffered saline-0.05% Tween 20, the membranes were incubated with secondary antibody conjugated with horseradish peroxidase for 1 h. After four washes, blots were developed with ECL Plus detection kit (Amersham), and membranes were exposed to Hyperfilm chemiluminescene film (Amersham). The following antibodies were used: Itch (611199 BD), p73 SAM domain and DN specific antibodies (Sayan et al; 2005), anti-actin (C-11; Santa Cruz), anti-β-tubulin (H-235; Santa Cruz), anti-lamin B (M-20; Santa Cruz)

Effects of shRNA Against Itch on Response to DNA Damage and Effect on p73 Levels Cells were transfected with plasmid, 24 hours later cells were replated in 100 mm dishes after a further 24 hours cells were treated with chemotherapeutic agents and samples were collected 0, 24 and 48 hours after drug treatment. Samples were collected for protein and FACS analysis Cell Cycle Determination Cells were transfected with a 5:1 ratio of pSUPER-ITCH-2, pSUPER-ITCH-18 or pSUPER scrambled together with a plasmid expressing GFP-spectrin. Cell cycle was analysed by flow cytometric evaluation of DNA stained with propidium iodide. Cells were fixed in ice cold 70% ethanol and stored at −20° C. Fixed cells were pelletted and resuspended in 50 ul RNAse and incubated at room temperature for 20 minutes. 200 ul of propidium iodide (50 ug/ml) was added and cells were incubated further at room temperature for 20 minutes. Cell cycle was measured on a FACScan (BD) cytometer using the Cell Quest Program (BD). Cells were gated for GFP expression to allow analysis only of transfected cells and twenty thousand events were evaluated using the Cell Quest Program (BD) and ModFit LT software (Verity Software).

Results and Discussion

Itch Expression Levels in Human Cell Lines and shRNA Against ITCH

To identify cell lines expressing Itch, lysates from an initial panel of 12 cell lines were separated by SDS-PAGE and itch expression was measured by western blot (FIG. 14A). As can be seen in FIG. 14A all cell lines tested expressed Itch. Itch was also found to be expressed in primary mouse embryonic fibroblasts (MEFs—data not shown).

In order to assess the effects of Itch knockdown on the response of cells to DNA damage, we undertook an RNAi approach to silence Itch expression. 10 shRNA-expressing vectors were tested for silencing efficiency. Two shRNA expressing vectors (2 and 18) were selected as the most efficient and used for subsequent studies. The effect of these shRNA vectors on endogenous expression of Itch was determined by western blot in the cells lines tested in FIG. 14A, and the greatest knockdown was found to be in Cos1, H1299, HeLa and HEK293T (FIG. 14B). The knockdown in these cell lines may have be greatest due to higher transfection efficiency in these cell lines with the methods used.

Effect of Itch shRNA on Cell Cycle

To investigate the effects of Itch knockdown on the cell cycle, of the four different cell lines were transfected with the shRNA vectors for Itch and a scrambled sequence, and 48 hours after transfection samples were collected and analysed with propidium iodide using a FACScan cytometer (FIG. 15). The distribution of the cells in the three stages of the cell cycle, G1, S-phase and G2, was further analysed using Mod-Fit software (Verity Software) (Table 1). Although a minor increase in percentage of cells in the G2 phase of cell cycle was observed in H1299 cells, overall Itch silencing has little or no effect on the cell cycle of these four cell lines.

TABLE 1

Distribution of cells in G1, G2 and S-phase proportion of cells after transfection of scrambled or shRNA ITCH transfection

| Cell line | shRNA transfected | % G1 | % S | % G2 |
|---|---|---|---|---|
| Cos1 | scrambled | 36.6 | 38.6 | 24.8 |
| Cos1 | shRNA Itch 2 | 37.5 | 36.9 | 25.6 |
| Cos1 | shRNA Itch 18 | 37.8 | 34.6 | 27.6 |
| H1299 | scrambled | 50.7 | 41.1 | 8.2 |
| H1299 | shRNA Itch 2 | 45.4 | 40.1 | 14.5 |
| H1299 | shRNA Itch 18 | 48.12 | 36.1 | 15.8 |
| HeLa | scrambled | 57.6 | 33.4 | 8.9 |
| HeLa | shRNA Itch 2 | 60.3 | 30.0 | 9.7 |
| HeLa | shRNA Itch 18 | 57.2 | 27.5 | 15.3 |
| HEK293T | scrambled | 37.1 | 57.2 | 5.7 |
| HEK293T | shRNA Itch 2 | 44.2 | 49.2 | 6.5 |
| HEK293T | shRNA Itch 18 | 45.7 | 48.8 | 5.5 |

Effect of Itch shRNA on p73 Levels in Cell Lines

Itch and p73 levels were assessed by western blot in Itch-depleted cell lines (FIG. 16). As can be seen in FIG. 16, in Itch-depleted Cos1 cells p73 protein levels are increased over control levels, a finding which is consistent with our previous published findings (Rossi et al; 2005). In H1299 cells there is also a possible increase in p73 levels although not as marked as in Cos1.

Effect of Itch shRNA on p73 Levels in Response to DNA Damage

The effect of Itch downregulation upon treatment with cisplatin, etoposide and doxorubicin (DNA-damaging chemotherapeutic agents) has been tested. Remarkably, in H1299 cells, Itch downregulation correlates with increased p73 levels, thus suggesting that Itch inactivation can potentiate the effects of chemotherapy by inducing p73 levels (FIG. 17).

Example 4

This Example Demonstrates an Automated High Throughput Enzyme-Linked Immunosorbent Assay (ELISA) for Use in Screening for Inhibitors of Itch Materials and Methods
Purified GST-Itch and Itch Mutant Glutathione-S-transferase (GST)-tagged Itch protein and inactivated Itch mutant (C830A) were expressed in bacteria. E. coli BL21 CodonPlus®(DE3)-RIL cells (Stratagene) were transformed with either wild type or mutant constructs prepared in the expression vector pGEX-6PI (Amersham Biosciences). Both GST fusion constructs are comprised of Itch Thr 277 to Glu 903, which lack the N-terminal C2 domain. Saturated cultures were prepared by inoculation of LB medium containing ampicillin (LB/amp) with growth overnight at 37° C. For expression, overnight cultures were diluted 1/100 in LB/amp at 37° C. until they reached an OD of 0.40. At this point the temperature was reduced to 15° C. and IPTG (50 µM final concentration) added to induce expression for 3-4 hours with shaking at 250 rpm. Cell lystates were prepared and the GST fusion proteins were purified on glutathione-sepharose beads (Amersham Biosciences) using standard procedures.

E1 and E2

EB ubiquitin activating enzyme was expressed in the Baculovirus system and purified by Ni-NTA chromatography (Qiagen) according to the manufacturer's instructions. The pET23aUbch7 bacterial construct directing the synthesis of the E2 ubiquitin conjugating enzyme Ubch7 was a gift of Dr P M Howley (Kumar S, Kao W H, Howley P M. (1997). Physical interaction between specific E2 and Hect E3 enzymes determines functional cooperativity. *J Biol. Chem.* 272:13548-54). Following expression in *E. coli* BL21 Codon-Plus®(DE3)-RIL cells (Stratagene), purified E2 was obtained by Ni-NTA affinity chromatography (Qiagen) according to the manufacturer's instructions.

FLAG-Tagged Ubiquitin

Purified recombinant ubiquitin containing an amino terminal FLAG sequence (DYKDDDDK) was purchased from Sigma Aldrich (cat. No. U5382).

Anti-FLAG M2 Peroxidase Conjugate

The anti-FLAG M2 antibody conjugated to hydrogen peroxidase was purchased from Sigma Aldrich (cat. No. A8592).

TMB ELISA Substrate

The peroxidase substrate 3,3',5,5'-tetramethylbenzidine (TMB), was prepared by making a 1% w/v TMB stock (Sigma Aldrich T-2885) in DMSO and diluting 1/10 into 0.1M sodium acetate buffer pH 4.5 containing 0.01% v/v hydrogen peroxide just prior to use.

High Throughput Screening Assay for Inhibitors of Itch

The assay was performed using automated liquid handling procedures in order to test it against the LOPAC$^{1280}$™ compound library (Sigma Aldrich), which consists of 1280 pharmacologically active compounds.

GST-tagged Itch (350 ng/ml in phosphate buffered saline containing 0.1% Tween 20 (PBST), 20 µl per well) was bound to glutathione-coated, clear-bottomed 384-well ELISA plates (Pierce, custom batch) at 22° C. for 1 hour. Negative control wells assigned to columns 23 and 24 were coated with an equivalent amount of Itch mutant (C830A). During this incubation, E2 (UbCH7) was pre-charged with ubiquitin in a 2× concentrated bulk mixture consisting of 468 ng/ml E1, 51 µg/ml E2 and 2 µM FLAG-ubiquitin in 1× ubiquitination buffer (25 mM TRIS pH8.0, 100 mM NaCl, 4 mM MgCl$_2$ 1.25 mM adenosine triphosphate (ATP), 50 µM dithiothreitol (DTT)) for 45 minutes at 22° C. Using this procedure E2 was pre-charged with FLAG-ubiquitin before mixing with the test compounds. At the end of the incubation, the plates were washed 3× with PBST.

The LOPAC$^{1280}$™ library compounds were pre-diluted from 10 mM stock plates in dimethylsulfoxide (DMSO) into ubiquitination buffer to give a final concentration of 10 µM in the assay. Following addition of 10 µl of diluted compound (or equivalent dilution of DMSO to control wells), 10 µl of the 2× pre-charge mixture was added to all wells and mixed to initiate the reaction. The plates were then sealed and the ubiquitination reactions allowed to proceed for 2 hours at 22° C. To stop the reactions and to remove unbound assay components, the plates were washed 3× with PBST prior to the addition of 20 µl/well anti-FLAG M2 peroxidase conjugate diluted 1/10,000 in PBST. After a further incubation of 1 hour at 22° C., the plates were washed 5× and 20 µl TMB substrate solution was added to all wells. The substrate development was allowed to proceed for 15 min at 22° C. before the reactions were stopped with 5 µl per well 1M HCl. The optical density at 450 nm (OD$_{450}$) was determined using a Tecan Safire II automated plate reader. The $OD_{450}$ signal is proportional to the amount of FLAG-ubiquitin ligated to the immobilised GST-Itch protein.

Results and Discussion

To demonstrate that the ELISA assay is specific for ubiquitinated Itch and is dependent on the presence of all the ubiquitination reaction components, the assay was performed with additional controls (FIG. 18). In the presence of E1, E2, FLAG Ub and immobilised wild type Itch, an assay $OD_{450}$ signal of 1.972 was obtained. Under the same conditions but with substitution of wild type Itch for the mutant Itch (C830A), a background signal of 0.093 was obtained, indicating a signal:background ratio of 21:1 for this assay. The additional controls showed that the signal was dependent on the presence of wild type Itch together with E1, E2 and FLAG Ub. The omission of any of these components resulted in background ELISA signals.

In order to test the performance of a high throughput screening assay for inhibitors of Itch, a screen of 1280 drug-like small molecules was performed using an automated ELISA assay. As an indication of assay performance and robustness we have applied the Z' and Z statistics, which are widely quoted for high throughput screening data by the industry (Zhang J H, Chung T D, Oldenburg K R. (1999). A Simple Statistical Parameter for Use in Evaluation and Validation of High Throughput Screening Assays. *J Biomol Screen.* 4:67-73). For this screen we obtained average values of 0.76 (range 0.71 to 0.83) and 0.73 (range 0.71 to 0.75) for Z' and for Z respectively. Z' and Z values in excess of 0.5 are indicative of an excellent assay capable of identifying outliers ("hits") for further investigation and optimisation.

The data obtained across the full screening run is shown in FIG. 19. The percentage activity values were calculated using the formula ($OD_{450}$ test−mean $OD_{450}$ negative controls)/(mean $OD_{450}$ positive controls−mean $OD_{450}$ negative controls)×100. Wells recording 70% or lower activity (>30% inhibition) were identified as hits. In this screen of 1280 compounds, 3 hits were obtained corresponding to an overall rate of 0.23%. Therefore a screen of a larger compound library of comparable chemical diversity would be expected to generate a sufficient number of hits to initiate a study of structure activity relationship (SAR). The identification of a SAR is important for the initiation of a medicinal chemistry program at the start of the drug discovery process. In this screen the compounds were tested at a fixed concentration of 10 μM, however it will be understood by those skilled in the art that this concentration may be increased in order to identify less potent compounds or reduced in order to identify only those hits with the greatest inhibitory activity.

REFERENCES

Agami, R., Blandino, G., Oren, M. and Shaul, Y. (1999) Interaction of c-Abl and p73alpha and their collaboration to induce apoptosis. *Nature*, 399, 809-813. Balint, E., Bates, S., and Vousden, K. H. (1999) Mdm2 binds p73 alpha without targeting degradation. *Oncogene*, 18, 3923-3929.

Bai Y, Yang C, Hu K, Elly C, Liu Y C. Itch E3 ligase-mediated regulation of TGF-beta signaling by modulating smad2 phosphorylation. Mol. Cell. 2004 Sep. 10; 15(5):825-31.

Bernardi R, Scaglioni P P, Bergmann S, Horn H F, Vousden K H and Pandolfi P P. PML regulates p53 stability by sequestering Mdm2 to the nucleolus. *Nat Cell Biol.* 6, 665-672, 2004

Bernassola, F., Salomoni, P., Oberst, A., Di Como, C. J., Pagano, M., Melino, G. and Pandolfi, P. P. (2004) Ubiquitin-dependent Degradation of p73 Is Inhibited by PML. *J Exp Med*, 199, 1545-1557.

Casciano, I., Mazzocco, K., Boni, L., Pagnan, G., Banelli, B., Allemanni, G., Ponzoni, M., Tonini, G. P., and Romani, M. (2002) Expression of DeltaNp73 is a molecular marker for adverse outcome in neuroblastoma patients. *Cell Death Differ*, 9, 246-251.

Castagnoli, L., Zucconi, A., Quondam, M., Rossi, M., Vaccaro, P., Panni, S., Paoluzi, S., Santonico, E., Dente, L., and Cesareni, G. (2001) Alternative bacteriophage display systems. *Comb Chem High Throughput Screen*, 4, 121-133.

Catani, M. V., Costanzo, A., Savini, I., Levrero, M., de Laurenzi, V., Wang, J. Y., Melino, G., and Avigliano, L. (2002) Ascorbate up-regulates MLH1 (Mut L homologue-1) and p73: implications for the cellular response to DNA damage. *Biochem J*, 364, 441-447.

Cesareni, G., Castagnoli, L., and Cestra, G. (1999) Phage displayed peptide libraries. *Comb Chem High Throughput Screen*, 2, 1-17.

Chen X, Zheng Y, Zhu J, Jiang J, and Wang J. p73 is transcriptionnally regulated by DNA damage, p53 and p73. Oncogene. 2001 Dec. 5; 20, 769-774.

Crook T, Nicholls J M, Brooks L, O'Nions J and Allday M J. High level expression of deltaN-p63: a mechanism for the inactivation of p53 in undifferentiated nasopharyngeal carcinoma (NPC)? *Oncogene*, 19, 3439-3444, 2000.

De Laurenzi, V., Catani, M. V., Terrinoni, A., Corazzari, M., Melino, G., Costanzo, A., Levrero, M. and Knight, R. A. (1999) Additional complexity in p73: induction by mitogens in lymphoid cells and identification of two new splicing variants epsilon and zeta. *Cell Death Differ*, 6, 389-390.

De Laurenzi, V., Costanzo, A., Barcaroli, D., Terrinoni, A., Falco, M., Annicchiarico-Petruzzelli, M., Levrero, M. and Melino, G. (1998) Two new p73 splice variants, gamma and delta, with different transcriptional activity. *J. Exp. Med*, 188, 1763-1768.

De Laurenzi, V., Raschella', G., Barcaroli, D., Annicchiarico-Petruzzelli, M., Ranalli, M., Catani, M. V., Tanno, B., Costanzo, A., Levrero, M., and Melino G. (2000) Induction of neuronal differentiation by p73, in a neuroblastoma cell line. *Journal Biological Chemistry*, 275, 15226-15231.

Dobbelstein, M., Wienzek, S., Konig, C., and Roth, J. (1999) Inactivation of the p53-homologue p73 by the mdm2-oncoprotein. *Oncogene*, 18, 2101-2106.

Fang, D., Elly, C., Gao, B., Fang, N., Altman, Y., Joazeiro, C., Hunter, T., Copeland, N., Jenkins, N., and Liu, Y. C. (2002) Dysregulation of T lymphocyte function in Itchy mice: a role for Itch in TH2 differentiation. *Nat Immunol*, 3, 281-287.

Flores E R, Sengupta S, Miller J B, Newman J J, Bronson R, Crowley D, Yang A, McKeon F, Jacks T. Tumor predisposition in mice mutant for p63 and p73: evidence for broader tumor suppressor functions for the p53 family. Cancer Cell. 2005 April; 7(4):363-73.

Gao M, Labuda T, Xia Y, Gallagher E, Fang D, Liu Y C, Karin M. Jun turnover is controlled through JNK-dependent phosphorylation of the E3 ligase Itch. Science. 2004 Oct. 8; 306(5694):271-5.

Gong, J. C., Costanzo, A., Yang, H. Q., Melino, G., Kaelin, Jr. W. G., Levrero, M. and Wang, J. Y. (1999) The tyrosine kinase c-Abl regulates p73 in apoptotic response to cisplatininduced DNA damage. *Nature*, 399, 806-809.

Gottifredi, V., Pelicci, G., Munarriz, E., Maione, R., Pelicci, P. G., and Amati, P. (1999) Polyomavirus large T antigen induces alterations in cytoplasmic signalling pathways involving Shc activation. *J Virol*, 73, 1427-1437.

Grob, T. J., Novak, U., Maisse, C., Barcaroli, D., Luthi, A. U., Pimia, F., Hugli, B., Graber, H. U., De Laurenzi, V., Fey, M. F., Melino, G., and Tobler, A. (2001) Human delta Np73 regulates a dominant negative feedback loop for TAp73 and p53. *Cell Death Differ*, 8, 1213-1223.

Hamilton, M. H., Tcherepanova, I., Huibregtse, J. M., and McDonnell, D. P. (2001) Nuclear import/export of hRPF1/Nedd4 regulates the ubiquitin-dependent degradation of its nuclear substrates. *J Biol Chem*, 276, 26324-26331.

Harvey, K. F., and Kumar, S. (1999) Nedd4-like proteins: an emerging family of ubiquitinprotein ligases implicated in diverse cellular functions. *Trends Cell Biol*, 9, 166-169.

Hicke, L. (2001) Protein regulation by monoubiquitin. *Nat Rev Mol Cell Biol*, 2, 195-201.

Ikawa, S., Nakagawara, A., and Ikawa Y. (1999) p53 family genes: structural comparison, expression and mutation. *Cell Death Differ*, 6, 1154-1161.

Irwin, M. S., Kondo, K., Marin, M. C., Cheng, L. S., Hahn, W. C. and Kaelin, W. G., Jr. (2003) Chemosensitivity linked to p73 function. Cancer Cell, 3, 403-410.

Kaghad, M., Bonnet, H., Yang, A., Creancier, L., Biscan, J. C., Valent, A., Minty, A., Chalon, P., Lelias, J. M., Dumont, X., Ferrara, P., McKeon, F. and Caput, D. (1997) Monoallelically expressed gene related to p53 at 1p36, a region frequently deleted in neuroblastoma and other human cancers. *Cell*, 90, 809-819.

Kloetzel, P. M. (2001) Antigen processing by the proteasome. *Nat Rev Mol Cell Biol*, 2, 179-187.

Kumar, S., Kao, W. H., and Howley, P. M. (1997) Physical interaction between specific E2 and Hect E3 enzymes determines functional cooperativity. *J Biol Chem*, 272, 13548-13554.

Lohrum, M. A., and Vousden, K. H. (1999) Regulation and activation of p53 and its family members. *Cell Death Differ*, 6, 1162-1168.

Lang G A, Iwakuma T, Suh Y A, Liu G, Rao V A, Parant J M, Valentin-Vega Y A, Terzian T, Caldwell L C, Strong L C, El-Naggar A K, Lozano G. (2004). Gain of function of a p53 hot spot mutation in a mouse model of Li Fraumeni syndrome. Cell, 119, 861-72.

Maisse, C., Munarriz, E., Barcaroli, D., Melino, G. and De Laurenzi, V. (2004) DNA damage induces the rapid and selective degradation of the DeltaNp73 isoform, allowing apoptosis to occur. *Cell Death Differ*, 11, 685-687.

Melino, G., Bernassola, F., Ranalli, M., Yee, K., Zong, W. X., Corazzari, M., Knight, R. A., Green, D. R., Thompson, C. and Vousden, K. H. (2004) p73 Induces apoptosis via PUMA transactivation and Bax mitochondrial translocation. *J Biol Chem*, 279, 8076-8083.

Melino, G., De Laurenzi, V., and Vousden, K. H. (2002) p73: Friend or foe in tumorigenesis. *Nat Rev Cancer*, 2, 605-615.

Melino, G., Lu, X., Gasco, M., Crook, T. and Knight, R. A. (2003) Functional regulation of p73 and p63: development and cancer. *Trends Biochem Sci*, 28, 663-670.

Miyazaki, K., Ozaki, T., Kato, C., Hanamoto, T., Fujita, T., Irino, S., Watanabe, K., Nakagawa, T. and Nakagawara, A. (2003) A novel HECT-type E3 ubiquitin ligase, NEDL2, stabilizes p73 and enhances its transcriptional activity. *Biochem Biophys Res Commun*, 308, 106-113.

Mills, A. A., Zheng, B., Wang, X. J., Vogel, H., Roop, D. R. and Bradley, A. (1999) p63 is a p53 homologue required for limb and epidermal morphogenesis. Nature, 398, 708-713.

Nakano, K., Balint, E., Ashcroft, M., and Vousden, K. H. (2000) A ribonucleotide reductase gene is a transcriptional target of p53 and p73. *Oncogene*, 19, 4283-4289.

Ongkeko, W. M., Wang, X. Q., Siu, W. Y., Lau, A. W., Yamashita, K., Harris, A. L., Cox, L. S., Poon, R. Y. (1999) MDM2 and MDMX bind and stabilize the p53-related protein p73. *Curr Biol*, 9, 829-832.

Nylander K, Vojtesek B, Nenutil R, Lindgren B, Roos G, Zhanxiang W, Sjostrom B, Dahlqvist A and Coates P J. Differential expression of p63 isoforms in normal tissues and neoplastic cells. *J Pathol*, 198, 417-427, 2002.

Park, B. J., Lee, S. J., Kim, J. I., Lee, C. H., Chang, S. G., Park, J. H. and Chi, S. G. (2000) Frequent alteration of p63 expression in human primary bladder carcinomas. Cancer Res, 60, 3370-3374.

Olive K P, Tuveson D A, Ruhe Z C, Yin B, Willis N A, Bronson R T, Crowley D, Jacks T. (2004) Mutant p53 gain of function in two mouse models of Li Fraumeni syndrome. Cell, 119, 841-60.

Perry, W. L., Hustad, C. M., Swing, D. A., O'Sullivan, T. N., Jenkins, N. A., and Copeland, N. G. (1998) The Itchy locus encodes a novel ubiquitin protein ligase that is disrupted in a18H mice. *Nat Genet*, 18, 143-146.

Putzer, B. M., Tuve, S., Tannapfel, and Stiewe, T. (2003) Increased DeltaN-p73 expression in tumors by upregulation of the E2F1-regulated, TA-promoter-derived DeltaN'-p73 transcript. *Cell Death Differ*, 10, 612-614.

Qiu, L., Joazeiro, C., Fang, N., Wang, H. Y., Elly, C., Altman, Y., Fang, D., Hunter, T., and Liu, Y. C. (2000) Recognition and ubiquitination of Notch by Itch, a hect-type E3 ubiquitin ligase. *J Biol Chem*, 275, 35734-35737.

Romani, M., Tonini, G. P., Banelli, B., Allemanni, G., Mazzocco, K., Scaruffi, P., Boni, L., Ponzoni, M., Pagnan, G., Raffaghello, L., Ferrini, S., Croce, M., and Casciano, I. (2003) Biological and clinical role of p73 in neuroblastoma. *Cancer Lett*, 197, 111-117.

Rossi M, De Laurenzi V, Munarriz E, Green D R, Liu Y C, Vousden K H, Cesareni G, Melino G. The ubiquitin-protein ligase Itch regulates p73 stability. EMBO J. 2005 Feb. 23; 24(4):836-48.

Sayan, A. E., Rossi, M., Melino, G. and Knight, R. A. (2004) p73: in silico evidence for a putative third promoter region. *Biochem Biophys Res Commun*, 313, 765-770.

Stiewe, T., and Putzer, B. M. (2002) Role of p73 in malignancy: tumor suppressor or oncogene? *Cell Death Differ*, 9, 237-245.

Strano, S., Munarriz, E., Rossi, M., Castagnoli, L., Shaul, Y., Sacchi, A., Oren, M., Sudol, M., Cesareni, G., and Blandino, G. (2001) Physical interaction with Yes-associated protein enhances p73 transcriptional activity. *J Biol Chem*, 276, 15164-15173.

Sudol, M. (1996) Structure and function of the WW domain. *Prog Biophys Mol Biol*, 65, 113-132.

Toh, W. H., Siddique, M. M., Boominathan, L., Lin, K. W. and Sabapathy, K. (2004) c-Jun regulates the stability and activity of the p53 homologue, p73. *J Biol Chem*.

Treier, M., Staszewski, L. M., and Bohmann, D. (1994) Ubiquitin-dependent c-Jun degradation in vivo is mediated by the delta domain. *Cell*, 78, 787-798.

Tschan, M. P., Grob, T. J., Peters, U. R., De Laurenzi V., Huegli, B., Kreuzer, K. A., Schmidt, C. A., Melino, G., Fey, M. F., Tobler, A. and Cajot, J-F. (2000) Enhanced p73 expression during differentiation and complex p73 isoforms in myeloid leukemia. *Biochemical Biophysical Research Communications*, 277, 62-65.

Ueda, Y., Hijikata, M., Takagi, S., Chiba, T. and Shimotohno, K. (1999) New p73 variants with altered C-terminal structures have varied transcriptional activities. *Oncogene*, 18, 4993-4998.

Urist M J, Di Como C J, Lu M L, Charytonowicz E, Verbel D, Crum C P, Ince T A, McKeon F D and Cordon-Cardo C. Loss of p63 expression is associated with tumor progression in bladder cancer. *Am J Pathol*, 161, 1199-1206, 2002.

Vossio, S., Palescandolo, E., Pediconi, N., Moretti, F., Balsano, C., Levrero, M., and Costanzo, A. (2002) DN-p73 is activated after DNA damage in a p53-dependent manner to regulate p53-induced cell cycle arrest. *Oncogene*, 21, 3796-3803.

Weissman, A. M. (2001) Themes and variations on ubiquitylation. *Nat Rev Mol Cell Biol*, 2, 169-178.

Winberg, G., Matskova, L., Chen, F., Plant, P., Rotin, D., Gish, G., Ingham, R., Ernberg, I., and Pawson, T. (2000) Latent membrane protein 2A of Epstein-Barr virus binds WW domain E3 protein ubiquitin ligases that ubiquitinate B-cell tyrosine kinases. *Mol Cell Biol*, 20, 8526-8535.

Yang, A., Walker, N., Bronson, R., Kaghad, M., Oosterwegel, M., Bonnin, J., Vagner, C., Bonnet, H., Dikkes, P., Sharpe, A., McKeon, F., and Caput, D. (2000) p73-deficient mice have neurological, pheromonal and inflammatory defects but lack spontaneous tumours. *Nature*, 404, 99-103.

Yang, A., Schweitzer, R., Sun, D., Kaghad, M., Walker, N., Bronson, R. T., Tabin, C., Sharpe, A., Caput, D., Crum, C. and McKeon, F. (1999) p63 is essential for regenerative proliferation in limb, craniofacial and epithelial development. Nature, 398, 714-718.

Yuan, Z. M., Shioya, H., Ishiko, T., Sun, X., Gu, J., Huang, Y. Y., Lu, H., Kharbanda, S., Weichselbaum, R. and Kufe, D. (1999) p73 is regulated by tyrosine kinase c-Abl in the apoptotic response to DNA damage. *Nature*, 399, 814-817.

Zaika, A. I., Slade, N., Erster, S. H., Sansome, C., Joseph, T. W., Pearl, M., Chalas, E., and Moll, U. M. (2002) DeltaNp73, a dominant-negative inhibitor of wild-type p53 and TAp73, is up-regulated in human tumors. *J Exp Med*, 196, 765-780.

Zeng, X., Chen, L., Jost, C. A., Maya, R., Keller, D., Wang, X., Kaelin, W. G. Jr, Oren, M., Chen, J., and Lu, H. (1999) MDM2 suppresses p73 function without promoting p73 degradation. *Mol Cell Biol*, 19, 3257-3266.

Zucconi, A., Dente, L., Santonico, E., Castagnoli, L., and Cesareni, G. (2001) Selection of ligands by panning of domain libraries displayed on phage lambda reveals new potential partners of synaptojanin 1. *J Mol Biol*, 307, 1329-1339.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method of inducing apoptosis in a cell comprising the step of decreasing the functional activity of Itch polypeptide or the nucleic acid encoding it, wherein said step comprises contacting said cell with a composition comprising siRNA or shRNA to Itch in an amount effective to induce apoptosis.

2. A method as claimed in claim 1 wherein altered the functional activity of Itch polypeptide or the nucleic acid encoding it, is inhibition of Itch.

3. A method for sensitising cells to DNA damaging agents through inhibition of Itch activity, wherein said inhibition of Itch activity comprises contacting said cell with a composition comprising siRNA or shRNA to Itch in an amount effective to sensitize cells to DNA damaging agents.

4. A method of decreasing the p73 or p63 ubiquitination activity of Itch in cells of a subject comprising administering to said subject an agent in an amount effective to inhibit p73 or p63 ubiquitination activity of Itch simultaneously or sequentially with a DNA damaging agent, wherein said agent that inhibits Itch activity is an siRNA or shRNA to Itch, and further wherein said subject is a subject that has cancer.

5. A method of modulating p63 or p73 stability in a cell comprising modulating Itch activity or expression, wherein said modulating comprises contacting said cell with a composition comprising siRNA or shRNA to Itch in an amount effective to modulate p73 or p63 stability.

6. A method for decreasing the activity of Itch in a cell, comprising administering to the cell an agent in an amount effective to decrease activity of Itch wherein said agent is an siRNA or shRNA to Itch.

7. A method of decreasing the p73 or p63 ubiquitination activity of Itch in the cells of a subject comprising administering to said subject, in a therapeutically effective amount to decrease the p73 or p63 ubiquitination activity of Itch, an siRNA or shRNA to Itch, and further wherein said subject is a subject that has cancer.

8. A method of decreasing the p73 or p63 ubiquitination activity of Itch in the cells of a subject comprising administering to said subject, in a therapeutically effective amount to decrease the p73 or p63 ubiquitination activity of Itch, an siRNA or shRNA to Itch, and further wherein said subject is a subject that has an epidermal development disorders or immune system dysfunction.

9. A method of increasing sensitivity of a tumour cell to a chemotherapeutic agent, comprising reducing Itch activity, expression levels, or function, by contacting said cell with a composition comprising siRNA or shRNA to Itch in an amount effective to increase sensitivity of the tumour cell to the chemotherapeutic agent.

10. The method of claim 1, 4, 6, 7 or 8 wherein said agent is an siRNA against Itch.

11. The method of claim 10, wherein said siRNA is further combined with a cytotoxic agent.

12. The method of claim 11, wherein said cytotoxic agent is a DNA damaging agent.

13. The method of any of claim 1, 4, 6, 7 or 8, wherein said siRNA comprises the sequence AAGTGCTTCTCAGAATGATGA (SEQ ID NO:1).

14. The method of any of claim 1, 4, 6, 7 or 8, wherein aid siRNA comprises the sequence AACCACAACACACGAATTACA (SEQ ID NO:2).

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: Consensus sequence motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Pro Pro Xaa Tyr
1

<210> SEQ ID NO 2
<211> LENGTH: 21
<212> TYPE: DNA
<213> ORGANISM: Artificial
<220> FEATURE:
<223> OTHER INFORMATION: Oligonucleotide

<400> SEQUENCE: 2
aagtgcttct cagaatgatg a                                             21

<210> SEQ ID NO 3
<211> LENGTH: 21
<212> TYPE: DNA
<213> ORGANISM: Artificial
<220> FEATURE:
```

-continued

<223> OTHER INFORMATION: Oligonucleotide

<400> SEQUENCE: 3
aaccacaaca cacgaattac a                                              21

<210> SEQ ID NO 4
<211> LENGTH: 21
<212> TYPE: DNA
<213> ORGANISM: Artificial
<220> FEATURE:
<223> OTHER INFORMATION: Oligonucleotide

<400> SEQUENCE: 4
aattctccga acgtgtcacg t                                              21

<210> SEQ ID NO 5
<211> LENGTH: 23
<212> TYPE: DNA
<213> ORGANISM: Artificial
<220> FEATURE:
<223> OTHER INFORMATION: Oligonucleotide

<400> SEQUENCE: 5
aaacattaaa gtcaaacaat atg                                            23

<210> SEQ ID NO 6
<211> LENGTH: 23
<212> TYPE: DNA
<213> ORGANISM: Artificial
<220> FEATURE:
<223> OTHER INFORMATION: Oligonucleotide

<400> SEQUENCE: 6
aaggagcaac atctggatta ata                                            23

<210> SEQ ID NO 7
<211> LENGTH: 8
<212> TYPE: PRT
<213> ORGANISM: Artificial
<220> FEATURE:
<223> OTHER INFORMATION: Amino terminal FLAG sequence

<400> SEQUENCE: 7

Asp Tyr Lys Asp Asp Asp Asp Lys
1               5

<210> SEQ ID NO 8
<211> LENGTH: 38
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<223> OTHER INFORMATION: Region of polypeptide

<400> SEQUENCE: 8

Met Leu Asn Asn His Gly His Ala Val Pro Ala Asn Ser Glu Met Thr
1               5                   10                  15

Ser Ser His Gly Thr Gln Ser Met Val Ser Gly Ser Cys Thr Pro
            20                  25                  30

Pro Pro Pro Tyr His Ala
        35